(12) United States Patent
Kao et al.

(10) Patent No.: US 8,241,630 B2
(45) Date of Patent: Aug. 14, 2012

(54) HER2 ANTIBODY COMPOSITION

(75) Inventors: Yung-Hsiang Kao, San Mateo, CA (US); Martin Vanderlaan, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 35 days.

(21) Appl. No.: 12/986,470

(22) Filed: Jan. 7, 2011

(65) Prior Publication Data

US 2011/0117097 A1 May 19, 2011

Related U.S. Application Data

(62) Division of application No. 12/480,013, filed on Jun. 8, 2009, now Pat. No. 7,879,325, which is a division of application No. 11/182,908, filed on Jul. 15, 2005, now Pat. No. 7,560,111.

(60) Provisional application No. 60/590,202, filed on Jul. 22, 2004.

(51) Int. Cl.
*A61K 39/395* (2006.01)

(52) U.S. Cl. .................................. 424/138.1; 424/143.1

(58) Field of Classification Search ........................ None
See application file for complete search history.

(56) References Cited

U.S. PATENT DOCUMENTS

| | | | |
|---|---|---|---|
| 4,968,603 A | 11/1990 | Slamon et al. |
| 5,183,884 A | 2/1993 | Kraus et al. |
| 5,480,968 A | 1/1996 | Kraus et al. |
| 5,641,869 A | 6/1997 | Vandlen et al. |
| 5,677,171 A | 10/1997 | Hudziak et al. |
| 5,720,937 A | 2/1998 | Hudziak et al. |
| 5,720,954 A | 2/1998 | Hudziak et al. |
| 5,725,856 A | 3/1998 | Hudziak et al. |
| 5,770,195 A | 6/1998 | Hudziak et al. |
| 5,772,997 A | 6/1998 | Hudziak et al. |
| 5,783,186 A | 7/1998 | Arakawa et al. |
| 5,821,337 A | 10/1998 | Carter et al. |
| 5,824,311 A | 10/1998 | Greene et al. |
| 6,054,297 A | 4/2000 | Carter et al. |
| 6,165,464 A | 12/2000 | Hudziak et al. |
| 6,267,958 B1 | 7/2001 | Andya et al. |
| 6,339,142 B1 | 1/2002 | Basey et al. |
| 6,387,371 B1 | 5/2002 | Hudziak et al. |
| 6,399,063 B1 | 6/2002 | Hudziak et al. |
| 6,407,213 B1 | 6/2002 | Carter et al. |
| 6,627,196 B1 | 9/2003 | Baughman et al. |
| 6,639,055 B1 | 10/2003 | Carter et al. |
| 6,685,940 B2 | 2/2004 | Andya et al. |
| 6,719,971 B1 | 4/2004 | Carter et al. |
| 6,800,738 B1 | 10/2004 | Carter et al. |
| 6,821,515 B1 | 11/2004 | Cleland et al. |
| 6,949,245 B1 | 9/2005 | Sliwkowski |
| 7,041,292 B1 | 5/2006 | Sliwkowski |
| 7,074,404 B2 | 7/2006 | Basey et al. |
| 7,097,840 B2 | 8/2006 | Erickson et al. |
| 7,371,376 B1 | 5/2008 | Fendly |
| 7,371,379 B2 | 5/2008 | Baughman et al. |
| 7,449,184 B2 | 11/2008 | Allison et al. |
| 7,485,302 B2 | 2/2009 | Adams et al. |
| 7,498,030 B2 | 3/2009 | Adams et al. |
| 7,501,122 B2 | 3/2009 | Adams et al. |
| 7,537,931 B2 | 5/2009 | Adams et al. |
| 7,560,111 B2 | 7/2009 | Kao et al. |
| 7,575,748 B1 | 8/2009 | Erickson et al. |
| 7,618,631 B2 | 11/2009 | Sliwkowski |
| 7,682,609 B2 | 3/2010 | Andya et al. |
| 7,700,299 B2 | 4/2010 | Moecks et al. |
| 7,846,441 B1 | 12/2010 | Hellmann |
| 7,862,817 B2 | 1/2011 | Adams et al. |
| 7,879,325 B2 | 2/2011 | Kao et al. |
| 7,892,549 B2 | 2/2011 | Paton et al. |
| 7,981,418 B2 | 7/2011 | Amler et al. |
| 7,993,834 B2 | 8/2011 | Mass |
| 8,075,890 B2 | 12/2011 | Carter et al. |
| 8,075,892 B2 | 12/2011 | Hellmann |
| 8,076,066 B2 | 12/2011 | Mass |
| 2001/0014326 A1 | 8/2001 | Andya et al. |
| 2002/0001587 A1 | 1/2002 | Erickson et al. |
| 2003/0147884 A1 | 8/2003 | Paton et al. |
| 2003/0170234 A1 | 9/2003 | Hellmann |
| 2003/0171278 A1 | 9/2003 | Dennis |
| 2003/0202972 A1 | 10/2003 | Andya et al. |
| 2004/0037823 A9 | 2/2004 | Paton et al. |
| 2004/0037824 A1 | 2/2004 | Baughman et al. |
| 2004/0106161 A1 | 6/2004 | Bossenmaier et al. |
| 2004/0258685 A1 | 12/2004 | Brunetta et al. |
| 2005/0002928 A1 | 1/2005 | Hellmann |
| 2005/0208043 A1 | 9/2005 | Adams et al. |
| 2005/0238640 A1 | 10/2005 | Sliwkowski |

(Continued)

FOREIGN PATENT DOCUMENTS

EP 1308455 A2 5/2003

(Continued)

OTHER PUBLICATIONS

Baselga et al., "Mechanism of action of anti-HER2 monoclonal antibodies" Annals of Oncology 12( SUPPL 1):S35-S41 ( 2001).

Aasland et al., "Expression of Oncogenes in Thyroid Tumours: Coexpression of c-erbB2/neu and c-erbB" *British Journal of Cancer* 57(4):358-363 (Apr. 1988).

Agus et al., "Clinical Activity in a Phase I Trial of HER-2-Targeted rhuMAb 2C4 (pertuzumab) in Patients with Advanced Solid Malignancies (AST)" *Proceedings of the American Association for Cancer Research* (Abstract No. 771) 22:192 (2003).

(Continued)

*Primary Examiner* — Laura B Goddard
(74) *Attorney, Agent, or Firm* — Wendy M. Lee

(57) ABSTRACT

A composition comprising a main species HER2 antibody that binds to domain II of HER2, and an amino acid sequence variant thereof comprising an amino-terminal leader extension is disclosed. Pharmaceutical formulations comprising the composition, and therapeutic uses for the composition are also disclosed.

2 Claims, 23 Drawing Sheets

U.S. PATENT DOCUMENTS

| | | | |
|---|---|---|---|
| 2005/0244417 A1 | 11/2005 | Ashkenazi et al. |
| 2006/0013819 A1 | 1/2006 | Kelsey |
| 2006/0018899 A1 | 1/2006 | Kao et al. |
| 2006/0034840 A1 | 2/2006 | Agus |
| 2006/0034842 A1 | 2/2006 | Adams et al. |
| 2006/0073143 A1 | 4/2006 | Adams et al. |
| 2006/0083739 A1 | 4/2006 | Sliwkowski |
| 2006/0088523 A1 | 4/2006 | Andya et al. |
| 2006/0121044 A1 | 6/2006 | Amler et al. |
| 2006/0165702 A1 | 7/2006 | Allison et al. |
| 2006/0188509 A1 | 8/2006 | Derynck et al. |
| 2006/0193854 A1 | 8/2006 | Adams et al. |
| 2006/0198843 A1 | 9/2006 | Adams et al. |
| 2006/0204505 A1 | 9/2006 | Sliwkowski et al. |
| 2006/0210561 A1 | 9/2006 | Baughman et al. |
| 2006/0216285 A1 | 9/2006 | Adams et al. |
| 2006/0228745 A1 | 10/2006 | Mass |
| 2006/0275305 A1 | 12/2006 | Bryant |
| 2006/0275306 A1 | 12/2006 | Andya et al. |
| 2007/0009976 A1 | 1/2007 | Lenz et al. |
| 2007/0020261 A1 | 1/2007 | Sliwkowski et al. |
| 2007/0026001 A1 | 2/2007 | Ashkenazi et al. |
| 2007/0037228 A1 | 2/2007 | Moecks et al. |
| 2007/0077243 A1 | 4/2007 | Carter et al. |
| 2007/0166753 A1 | 7/2007 | Mass |
| 2007/0184055 A1 | 8/2007 | Sliwkowski |
| 2007/0202516 A1 | 8/2007 | Mass |
| 2007/0224203 A1 | 9/2007 | Friess et al. |
| 2007/0269429 A1 | 11/2007 | Kelsey et al. |
| 2007/0292419 A1 | 12/2007 | Hellmann |
| 2008/0038271 A1 | 2/2008 | Amler et al. |
| 2008/0050373 A1 | 2/2008 | Cohen |
| 2008/0050385 A1 | 2/2008 | Friess et al. |
| 2008/0102069 A1 | 5/2008 | Friess et al. |
| 2008/0112957 A1 | 5/2008 | Fendly et al. |
| 2008/0112958 A1 | 5/2008 | Mass |
| 2008/0160026 A1 | 7/2008 | Ashkenazi et al. |
| 2008/0187533 A1 | 8/2008 | Hellmann |
| 2008/0226659 A1 | 9/2008 | Erickson et al. |
| 2008/0241146 A1 | 10/2008 | Ashkenazi et al. |
| 2008/0286280 A1 | 11/2008 | Kallmeyer et al. |
| 2008/0317753 A1 | 12/2008 | Amler et al. |
| 2009/0081223 A1 | 3/2009 | Allison et al. |
| 2009/0087432 A1 | 4/2009 | Sliwkowski |
| 2009/0148402 A1 | 6/2009 | Brunetta et al. |
| 2009/0155259 A1 | 6/2009 | Derynck et al. |
| 2009/0202546 A1 | 8/2009 | Harris et al. |
| 2009/0239236 A1 | 9/2009 | Mass |
| 2009/0285837 A1 | 11/2009 | Kao et al. |
| 2009/0317387 A1 | 12/2009 | Paton et al. |
| 2010/0008975 A1 | 1/2010 | Amler et al. |
| 2010/0015157 A1 | 1/2010 | Andya et al. |
| 2010/0016556 A1 | 1/2010 | Carter et al. |
| 2010/0112603 A1 | 5/2010 | Moecks et al. |
| 2010/0158899 A1 | 6/2010 | Andya et al. |
| 2010/0285010 A1 | 11/2010 | Friess et al. |
| 2011/0033460 A1 | 2/2011 | Fendly et al. |
| 2011/0064737 A1 | 3/2011 | Agus |
| 2011/0117096 A1 | 5/2011 | Bossenmaier et al. |
| 2011/0117097 A1 | 5/2011 | Kao et al. |
| 2011/0129464 A1 | 6/2011 | Adams et al. |
| 2011/0165157 A1 | 7/2011 | Derynck et al. |
| 2011/0223159 A1 | 9/2011 | Friess et al. |
| 2011/0236383 A1 | 9/2011 | Andya et al. |
| 2011/0245103 A1 | 10/2011 | Amler et al. |
| 2011/0246399 A1 | 10/2011 | Amler et al. |
| 2011/0250194 A1 | 10/2011 | Hellmann |
| 2012/0003217 A1 | 1/2012 | Bryant |
| 2012/0034213 A1 | 2/2012 | Hellmann |
| 2012/0034609 A1 | 2/2012 | Mass |

FOREIGN PATENT DOCUMENTS

| | | |
|---|---|---|
| WO | 94/00136 | 1/1994 |
| WO | 94/22478 | 10/1994 |
| WO | 97/20858 | 6/1997 |
| WO | WO 98/17797 A1 | 4/1998 |
| WO | WO 00/69460 A1 | 11/2000 |
| WO | 01/00245 | 1/2001 |
| WO | WO 01/00238 A1 | 1/2001 |
| WO | WO 03/087131 A2 | 10/2003 |

OTHER PUBLICATIONS

Agus et al., "Clinical Activity in a Phase I Trial of HER2-Targeted rhuMAb 2C4 (pertuzumab) in Patients with Advanced Solid Malignancies" (Slides presented at the 2003 ASCO Annual Meeting) pp. 1-32 (2003).

Agus et al., "Efficacy and safety of single agent pertuzumab (rhuMAb 2C4), a HER dimerization inhibitor, in hormone refractory prostate cancer after failure of taxane-based therapy" *Journal of Clinical Oncology* (Abstract 4624 from the 41st Annual Meeting of ASCO) 23(16S):408s (Jun. 1, 2005).

Agus et al., "Targeting ligand-activated ErbB2 signaling inhibits breast and prostate tumor growth" *Cancer Cell* 2(2):127-137 (Aug. 2002).

Agus, D. et al., "Efficacy and safety of single agent pertuzumab (rhuMAb 2C4), a HER dimerization inhibitor, in hormone refractory prostate cancer after failure of taxane-based therapy" (Poster 4624 from the 41st Annual Meeting of the American Society of Clinical Oncology) (May 15, 2005).

Amler et al., "Identification of a predictive expression pattern for phosphorylated HER2 as a potential diagnostic marker for pertuzumab (OMNITARG) activity in ovarian cancer" (Poster 4497 presented at the Apr. 2006 American Association for Cancer Research Meeting) (Apr. 2006).

Arteaga et al., "p185$^{c-erbB-2}$ Signaling Enhances Cisplatin-induced Cytotoxicity in Human Breast Carcinoma Cells: Association Between an Oncogenic Receptor Tyrosine Kinase and Drug-induced DNA Repair" *Cancer Research* 54(14):3758-3765 (Jul. 15, 1994).

Bacus et al., "Differentiation of Cultured Human Breast Cancer Cells (AU-565 and MCF-7) Associated With Loss of Cell Surface HER-2/neu Antigen" *Molecular Carcinogenesis* 3(6):350-362 (1990).

Bacus et al., "Tumor-inhibitory Monoclonal Antibodies to the HER-2/Neu Receptor Induce Differentiation of Human Breast Cancer Cells" *Cancer Research* 52(9):2580-2589 (May 1, 1992).

Baselga and Mendelsohn, "Receptor Blockade With Monoclonal Antibodies as Anti-Cancer Therapy" *Pharmac. Ther.* 64:127-154 (1994).

Baselga et al., "Phase II Study of Weekly Intravenous Recombinant Humanized Anti-p185$^{HER2}$ Monoclonal Antibody in Patients With HER2/neu-Overexpressing Metastatic Breast Cancer" *J. Clin. Oncol.* 14(3):737-744 (Mar. 1996).

Borst et al., "Oncogene Alterations in Endometrial Carcinoma" *Gynecologic Oncology* 38(3):364-366 (Sep. 1990).

Bossenmaier et al., "Presence of HER2/HER3 heterodimers predicts antitumor effects of pertuzumab (OMNITARG) in different human xenograft models" *Proc Am Assoc Cancer Res* (Abstract 5342) 45:1232 (Mar. 2004).

Carraway and Cantley, "A Neu Acquaintance for ErbB3 and ErbB4: A Role for Receptor Heterodimerization in Growth Signaling" *Cell* 78:5-8 (Jul. 15, 1994).

Carraway et al., "Neuregullin-2, A New Ligand of ErbB3/ErbB4-Receptor Tyrosine Kinases" *Nature* 387:512-516 (May 1997).

Chang et al., "Ligands for ErbB-Family Receptors Encoded by a Neuregulin-Like Gene" *Nature* 387:509-512 (May 29, 1997).

Cohen et al., "Expression Pattern of the neu (NGL) Gene-Encoded Growth Factor Receptor Protein (p185$^{neu}$) in Normal and Transformed Epithelial Tissues of the Digestive Tract" *Oncogene* 4(1):81-88 (Jan. 1989).

Cortes et al., "Open label, randomized, phase II study of pertuzumab (OMNITARG) in patients with metastatic breast cancer (MBC) with low expression of HER2" (Poster 3068 from the 41st Annual Meeting of the American Society of Clinical Oncology (ASCO)) (May 15, 2005).

Cortes et al., "Open label, randomized, phase II study of pertuzumab (P) in patients (pts) with metastatic breast cancer (MBC) with low expression of HER2" *Journal of Clinical Oncology* (Abstract 3068 from the 41st Annual Meeting of ASCO) 23(16s):208s (Jun. 1, 2005).

D'Souza and Taylor-Papadimitriou., "Overexpression of ERBB2 in Human Mammary Epithelial Cells Signals Inhibition of Transcription of the E-Cadherin Gene" *Proc. Natl. Acad. Sci. USA* 91(15):7202-7206 (Jul. 19, 1994).

de Bono et al., "An open label, phase II, multicenter study to evaluate the efficacy and safety of pertuzumab in chemotherapy-naive patients with Hormone-Refractory Prostate Cancer (HRPC)" (Poster 4609 from the 41st Annual Meeting of the American Society of Clinical Oncology (ASCO)) (May 15, 2005).

de Bono et al., "An open label, phase II, multicenter, study to evaluate the efficacy and safety of pertuzumab (P) in chemotherapy naive patients (pts) with Hormone Refractory Prostate Cancer (HRPC)" *Journal of Clinical Oncology* (Abstract 4609; 41st Annual Meeting of ASCO) 23(16S):405s (Jun. 1, 2005).

Drebin et al., "Down-Modulation of an Oncogene Protein Product and Reversion of the Trasnformed Phenotype by Monoclonal Antibodies" *Cell* 41(3):695-706 (Jul. 1985).

Drebin et al., "Monoclonal Antibodies Reactive With Distinct Domains of the neu Oncogene-Encoded p185 Molecule Exert Synergistic Anti-Tumor Effects In Vivo" *Oncogene* 2:273-277 (1988).

Earp et al., "Heterodimerization and Functional Interaction Between EGF Receptor Family Members: A New Signaling Paradigm With Implications for Breast Cancer Research" *Breast Cancer Res and Treatment* 35:115-132 (1995).

Fendly, B.M. et al., "Characterization of Murine Monoclonal Antibodies Reactive to Either the Human Epidermal Growth Factor Receptor or HER2/neu Gene Product" *Cancer Research* 50:1550-1558 the Human (Mar. 1, 1990).

Franklin et al., "Insights into ErbB signaling from the structure of the ErbB2-pertuzumab complex" *Cancer Cell* 5(4):317-328 (Apr. 2004).

Friess et al., "Combination treatment with erlotinib and pertuzumab against human tumor xenografts is superior to monotherapy" *Clinical Cancer Research* 11(14):5300-5309 (Jul. 15, 2005).

Friess et al., "In vivo activity of recombinant humanized monoclonal antibody 2C4 in xenografts is independent of tumor type and degree of HER2 overexpression" *European Journal of Cancer* (Abstract 496 from the EORTC-NCI-AACR conference in Frankfurt, Germany Nov. 19-22, 2002.) 38 (Suppl. 7):S149 (2002).

Fukushige at al., "Localization of a Novel v-erbB-Related Gene, c-erbB-2, on Human Chromosome 17 and its Amplification in a Gastric Cancer Cell Line" *Molecular & Cellular Biology* 6(3):955-958 (Mar. 1986).

Gordon et al., "Clinical activity of pertuzumab (rhuMab 2C4) in advanced, refractory or recurrent ovarian cancer (OC), and the role of HER2 activation status" *Journal of Clinical Oncology* (Abstract #5051 from the 41st Annual Meeting of ASCO) 23(16S):467s (Jun. 1, 2005).

Gordon et al., "Clinical activity of pertuzumab (rhuMab 2C4) in advanced, refractory or recurrent ovarian cancer and the role of HER2 activation status" (Poster #5051 from the 41st Annual Meeting of the American Society of Clinical Oncology (ASCO)) (May 15, 2005).

Groenen et al., "Structure-Function Relationships for the EGF/TGF-α Family of Mitogens" *Growth Factors* 11:235-257 (1994).

Gu et al., "Overexpression of her-2/neu in Human Prostate Cancer and Benign Hyperplasia" *Cancer Letters* 99:185-189 (1996).

Guerin et al., "Overexpression of Either c-myc or c-erbB-2/neu Proto-Oncogenes in Human Breast Carcinomas: Correlation with Poor Prognosis" *Oncogene Res.* 3:21-31 (1988).

Hancock et al., "A Monoclonal Antibody Against the c-erbB-2 Protein Enhances the Cytotoxicity of cis-Diamminedichloroplatinum Against Human Breast and Ovarian Tumor Cell Lines" *Cancer Research* 51:4575-4580 (Sep. 1, 1991).

Harari et al., "Neuregulin-4: A Novel Growth Factor That Acts Through the ErbB-4 Receptor Tyrosine Kinase" *Oncogene* 18:2681-2689 (1999).

Harris, Reed, "The Ideal Chromatographic Antibody Characterization Method" (Slides 1-36, IBC Antibody Production Conference, Feb. 13, 2002).

Harwerth et al., "Monoclonal Antibodies Against the Extracellular Domain of the erbB-2 Receptor Function as Partial Ligan Agonists" *Journal of Biological Chemistry* 267(21):15160-15167 (Jul. 25, 1992).

Hasmann et al., "Pertuzumab (Omnitarg) Potentiates Antitumor Effects on NSCLS Xenografts without Increasing Toxicity when Combined with Cytotoxic Chemotherapeutic Agents" *American Association for Cancer Research* (Abstract #B213; supplement to Clinical Cancer Research) 9(16) (Dec. 1, 2003).

Holmes et al., "Identification of Heregulin, A Specific Activator of p185$^{erbB2}$" *Science* 256:1205-1210 (May 22, 1992).

Hudziak et al., "p185$^{HER2}$ Monoclonal Antibody Has Antiproliferative Effects In Vitro and Sensitizes Human Breast Tumor Cells to Tumor Necrosis Factor" *Molecular & Cellular Biology* 9(3):1165-1172 (Mar. 1989).

Kasprzyk et al., "Therapy of an Animal Model of Human Gastric Cancer Using a Combination of Anti-erbB-2 Monoclonal Antibodies" *Cancer Research* 52(10):2771-2776 (May 15, 1992).

Kern et al., "p185$^{neu}$ Expression in Human Lung Adenocarcinomas Predicts Shortened Survival" *Cancer Research* 50(16):5184-5191 (Aug. 15, 1990).

King et al., "Amplification of a Novel v-erbB-Related Gene in a Human Mammary Carcinoma" *Science* 229:974-976 (Sep. 1985).

Klapper et al., "A Subclass of Tumor-Inhibitory Monoclonal Antibodies to ErbB-2/HER2 Blocks Crosstalk With Growth Factor Receptors" *Oncogene* 14:2099-2109 (1997).

Kotts et al., "Differential Growth Inhibition of Human Carcinoma Cells Exposed to Monoclonal Antibodies Directed against the Extracellular Domain of the HER2/ERBB2 Protooncogene" *In Vitro* (Abstract #176) 26(3):59A (1990).

Kraus et al., "Isolation and Characterization of ERBB3, A Third Member of the ERBB/Epidermal Factor Receptor Family: Evidence for Overexpression in a Subset of Human Mammary Tumors" *Proc. Natl. Acad. Sci. USA* 86:9193-9197 (Dec. 1989).

Kumar et al., "Regulation of Phosphorylation of the c-erbB-2/HER2 Gene Product by a Monoclonal Antibody and Serum Growth Factor(s) in Human Mammary Carcinoma Cells" *Molecular & Cellular Biology* 11(2):979-986 (Feb. 1991).

Lee, "Transforming growth factor alpha: expression, regulation, and biological activities" *Pharm. Rev.* 47(1):51-85 (Mar. 1995).

Lemke,G., "Neuregulins in Development" *Molecular and Cellular Neurosciences* 7:247-262 (1996).

Levi et al., "The Influence of Heregulins on Human Schwann Cell Proliferation" *J. Neuroscience* 15(2):1329-1340 (Feb. 1995).

Lewis et al., "Differential Responses of Human Tumor Cell Lines to Anti-p185$^{HER2}$ Monoclonal Antibodies" *Cancer Immunol. Immunother.* 37:255-263 (1993).

Lewis et al., "Growth Regulation of Human Breast and Ovarian Tumor Cells by Heregulin: Evidence for the Requirement of ErbB2 as a Critical Component in Mediating Heregulin Responsiveness" *Cancer Research* 56:1457-1465 (Mar. 15, 1996).

MacCallum, et al., "Antibody-antigen interactions: contact analysis and binding site topography" *J. Mol. Biol.*262:732-745 (1996).

Maier at al., "Requirements for the Internalization of a Murine Monoclonal Antibody Directed against the HER-2/neu Gene Product c-erbB-2" *Cancer Research* 51(19):5361-5369 (Oct. 1, 1991).

Masui at al., "Growth Inhibition of Human Tumor Cells in Athymic Mice by Anti-Epidermal Growth Factor Receptor Monoclonal Antibodies" *Cancer Research* 44(3):1002-1007 (Mar. 1984).

McCann et al., "c-erbB-2 Oncoprotein Expression in Primary Human Tumors" *Cancer* 65(1):88-92 (Jan. 1, 1990).

McKenzie et al., "Generation and Characterization of Monoclonal Antibodies Specific for the Human neu Oncogene Product, p185" *Oncogene* 4:543-548 (1989).

Morrissey et al., "Axon-Induced Mitogenesis of Human Schwann Cells Involves Heregulin and p185$^{erbB2}$" *Proc. Natl. Acad. Sci. USA* 92:1431-1435 (Feb. 1995).

Myers et al., "Biological Effects of Monoclonal Antireceptor Antibodies Reactive with neu Oncogene Product, p185neu" *Methods in Enzymology* 198:277-290 (1991).

Nahta et al., "The HER-2-targeting antibodies trastuzumab and pertuzumab synergistically inhibit the survival of breast cancer cells" *Cancer Research* 64(7):2343-2346 (Apr. 1, 2004).

NCBI Database, "BC009722" (Accession 1S78_E; www.ncbi.nlm.nih.gov/protein/48425587?sat=prot&satkey=1876225) (Jan. 29, 2004).

Panka et al., "Variable region framework differences result in decreased or increased affinity of variant anti-digoxin antibodies" *Proc. Natl. Acad. Sci. USA* 85:3080-3084 (May 1988).

Park et al., "Amplification, Overexpression, and Rearrangement of the erbB-2 Protooncogene in Primary Human Stomach Carcinomas" *Cancer Research* 49(23):6605-6609 (Dec. 1, 1989).

Pietras et al., "Antibody to HER-2/neu Receptor Blocks DNA Repair After Cisplatin in Human Breast and Ovarian Cancer Cells" *Oncogene* 9:1829-1838 (1994).

Plowman et al., "Heregulin Induces Tyrosine Phosphorylation of HER4/p180$^{erbB4}$" *Nature* (Letters to Nature) 366:473-475 (Dec. 2, 1993).

Plowman et al., "Ligand-Specific Activation of HER4/p180$^{erbB4}$, A Fourth Member of the Epidermal Growth Factor Receptor Family" *Proc. Natl. Acad. Sci. USA* 90:1746-1750 (Mar. 1993).

Porter, Jill, "The role of Analytical Comparability in the Global Approval of Zenapax" *Case Studies—Biotech Manufacturing Changes* (Slides 1-18, The 3rd International Conference: Strategic Use of Comparability Studies and Assays for Well Characterized Biologicals), Washington D.C., Sep. 18-21, 2000.

Reid et al., "Effects of Cell Culture Process Change on Humanized Characteristics" (Poster presented at WCBP 2003 conference in San Francisco, Jan. 7-10, 2003, p. 1).

Ross et al., "HER-2/neu Gene Amplification Status in Prostate Cancer by Fluorescencee in Situ Hybridization" *Hum. Pathol.* 28(7):827-833 (Jul. 1997).

Ross et al., "Prognostic Significance of HER-2/neu Gene Amplification Status by Fluorescence In Situ Hybridization of Prostate Carcinoma" *Cancer* 79(11):2162-2170 (Jun. 1, 1997).

Rouse et al., "Top Down Glycoprotein Characterization by High Resolution Mass Spectrometry and Its Application to Biopharmaceutical Develpoment" (Slides 1-27, WCBP 2004 meeting,Washington DC, Jan. 6-9, 2004).

Rudikoff et al., "Single amino acid substitution altering antigen-binding specificity" *Proc. Natl. Acad. Sci. USA* 79:1979-1983 (Mar. 1982).

Sadasivan et al., "Overexpression of Her-2/Neu May Be an Indicator of Poor Prognosis in Prostate Cancer" *J. Urol.* 150:126-131 (Jul. 1993).

Sarup et al., "Characterization of an Anti-P185$^{HER2}$ Monoclonal Antibody that Stimulates Receptor Function and Inhibits Tumor Cell Growth" *Growth Regulation* 1:72-82 (1991).

Schaefer et al., "γ-Heregulin: A Novel Heregulin Isoform That is an Autocrine Growth Factor for the Human Breast Cancer Cell Line, MDA-MB-175" *Oncogene* 15:1385-1394 (1997).

Scott et al., "p185$^{HER2}$ Signal Transduction in Breast Cancer Cells" *Journal of Biological Chemistry* 266(22):14300-14305 (Aug. 5, 1991).

Shawver et al., "Ligand-Like Effects Induced by Anti-c-erbB-2 Antibodies Do Not Correlate with and Are Not Required for Growth Inhibition of Human Carcinoma Cells" *Cancer Research* 54(5):1367-1373 (Mar. 1, 1994).

Shepard et al., "Monoclonal Antibody Therapy of Human Cancer: Taking the HER2 Protooncogene to the Clinic" *J. Clin. Immunol.* 11(3):117-127 (1991).

Shields et al., "High Resolution Mapping of the Binding Site on Human IgG1 for FcγRI, FcγRII, FcγRIII, and FcRn and Design of IgG1 Variants with Improved Binding to the FcγR" *Journal of Biological Chemistry* 276(9):6591-6604 (2001).

Slamon et al., "Human Breast Cancer: Correlation of Relapse and Survival with Amplification of the HER-2/neu Oncogene" *Science* 235:177-182 (Jan. 9, 1987).

Slamon et al., "Studies of the HER-2/neu Proto-Oncogene in Human Breast and Ovarian Cancer" *Science* 244:707-712 (May 12, 1989).

Sliwkowski et al., "Coexpression of erbB2 and erbB3 Proteins Reconstitutes a High Affinity Receptor for Heregulin" *Journal of Biological Chemistry* 269(20):14661-14665 (May 20, 1994).

Spiridon et al., "Targeting multiple Her-2 epitopes with monoclonal antibodies results in improved antigrowth activity of a human breast cancer cell line in vitro and in vivo" *Clinical Cancer Research* 8(6):1720-1730 (Jun. 2002).

Stancovski et al., "Mechanistic Aspects of the Opposing Effects of Monoclonal Antibodies to the ERBB2 Receptor on Tumor Growth" *Proc. Natl. Acad. Sci. USA* 88(19):8691-8695 (Oct. 1, 1991).

Tagliabue et al., "Selection of Monoclonal Antibodies Which Induce Internalization and Phosphorylation of p185$^{HER2}$ and Growth Inhibition of Cells With HER2/NEU Gene Amplification" *International Journal of Cancer* 47(6):933-937 (Apr. 1, 1991).

Vajdos et al., "Comprehensive functional maps of the antigen-binding site of an anti-ErbB2 antibody obtained with shotgun scanning mutagenesis" *Journal of Molecular Biology* 320(2):415-428 (Jul. 5, 2002).

Vitetta and Uhr, "Monoclonal Antibodies as Agonists: An Expanded Role for Their Use in Cancer Therapy" *Cancer Research* 54(20):5301-5309 (Oct. 15, 1994).

Weiner et al., "Expression of the neu Gene-encoded Protein (P185$^{neu}$) in Human Non-Small Cell Carcinomas of the Lung" *Cancer Research* 50(2):421-425 (Jan. 15, 1990).

Williams et al., "Expression of c-erbB-2 in Human Pancreatic Adenocarcinomas" *Pathobiology* 59(1):46-52 (1991).

Wu et al., "Apoptosis Induced by an Anti-Epidermal Growth Factor Receptor Monoclonal Antibody in a Human Colorectal Carcinoma Cell Line and its Delay by Insulin" *Journal of Clinical Investigation* 95(4):1897-1905 (Apr. 1995).

Xu et al., "Antibody-Induced Growth Inhibition is Mediated Through Immunochemically and Functionally Distinct Epitopes on the Extracellular Domain of the c-erbB-2 (HER-2/neu) Gene Product p185" *International Journal of Cancer* 53(3):401-408 (Feb. 1, 1993).

Yokota et al., "Amplification of c-erbB-2 Oncogene in Human Adenocarcinomas in Vivo" *Lancet* 1(8484):765-767 (Apr. 5, 1986).

Yonemura et al., "Evaluation of Immunoreactivity for erbB-2 Protein as a Marker of Poor Short Term Prognosis in Gastric Cancer" *Cancer Research* 51(3):1034-1038 (Feb. 1, 1991).

Zhang et al., "Neuregulin-3 (NRG3): A novel neural tissue-enriched protein that binds and activates ErbB4" *Proc. Natl. Acad. Sci. USA* 94:9562-9567 (Sep. 22, 1997).

Zhau et al., "Amplification and Expression of the c-erb B-2/neu Proto-Oncogene in Human Bladder Cancer" *Molecular Carcinogenesis* 3(5):254-257 (1990).

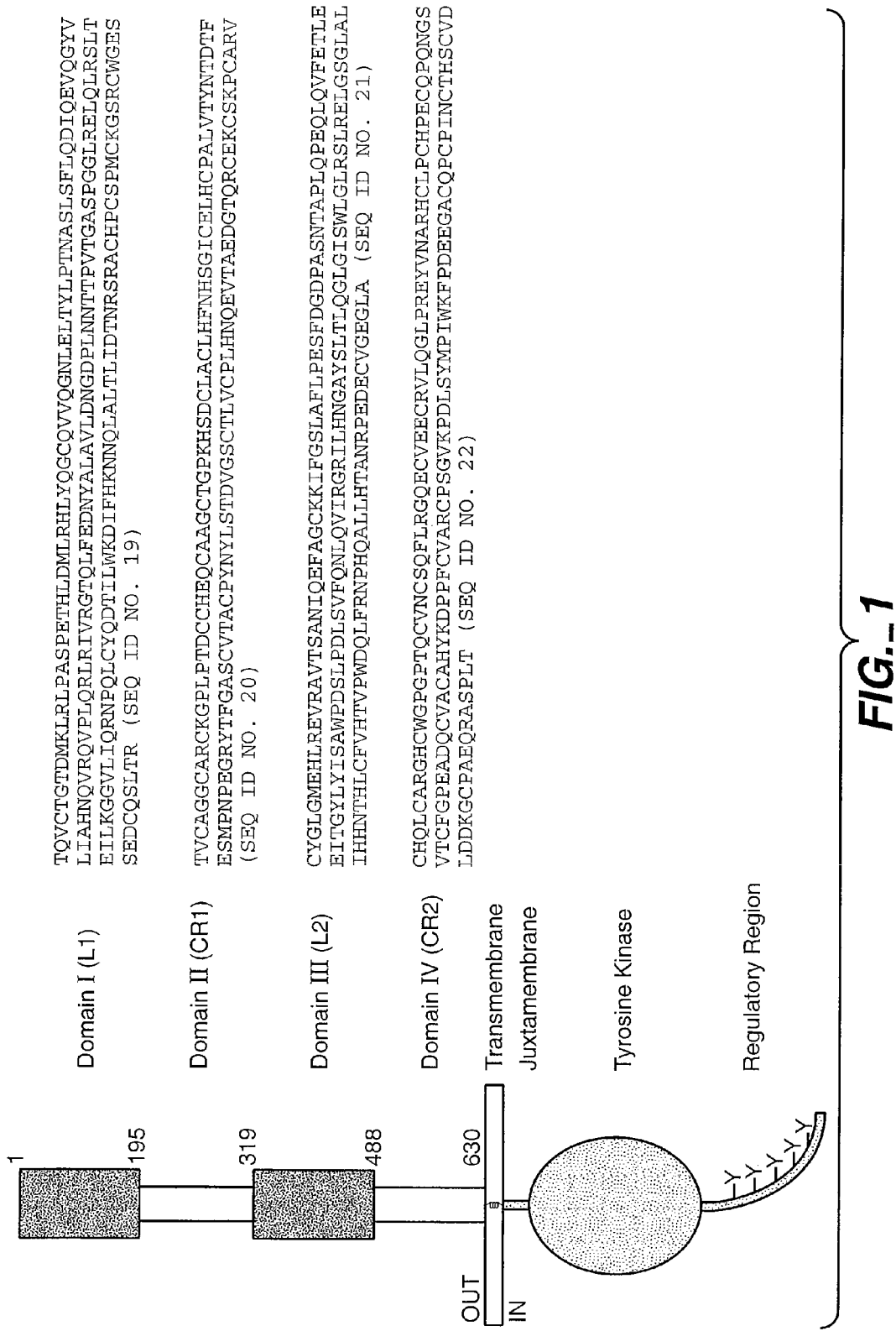
FIG._1

VARIABLE LIGHT

```
                    10          20              30              40
2C4     DTVMTQSHKIMSTSVGDRVSITC [KASQDVSIGVA]   WYQQRP
        **        ****  *        *                   *
574     DIQMTQSPSSLSASVGDRVTITC [KASQDVSIGVA]   WYQQKP
                                  *   * hum κI  DIQMTQSPSSLSASVGDRVTITC [RASQSISNYLA]   WYQQKP 50              60          70          80
2C4     GQSPKLLIY [SASYRYT]     GVPDRFTGSGSGTDFTFTISSVQA
        **                        *   *            *    * *
574     GKAPKLLIY [SASYRYT]     GVPSRFSGSGSGTDFTLTISSLQP
                   * ***** hum κI  GKAPKLLIY [AASSLES]     GVPSRFSGSGSGTDFTLTISSLQP 90         100
2C4     EDLAVYYC [QQYYIYPYT]   FGGGTKLEIK  (SEQ ID NO:1)
         * *                     *   *
574     EDFATYYC [QQYYIYPYT]   FGQGTKVEIK  (SEQ ID NO:3)
                   *** * hum κI  EDFATYYC [QQYNSLPWT]   FGQGTKVEIK  (SEQ ID NO:5)
```

FIG._2A

VARIABLE HEAVY

```
                    10              20              30                  40
2C4     EVQLQQSGPELVKPGTSVKISCKAS [GFTFTDYTMD]     WVKQS
           **   **  *  *  *** *                      * *
574     EVQLVESGGGLVQPGGSLRLSCAAS [GFTFTDYTMD]     WVRQA
                                    ** * * hum III EVQLVESGGGLVQPGGSLRLSCAAS [GFTFSSYAMS]     WVRQA 50       a      60              70              80
2C4     HGKSLEWIG [DVNPNSGGSIYNQRFKG]     KASLTVDRSSRIVYM
         *   *  **                        *** *    **** *
574     PGKGLEWVA [DVNPNSGGSIYNQRFKG]     RFTLSVDRSKNTLYL
                   **** * ****         *  * hum III PGKGLEWVA [VISGDGGSTYYADSVKG]     RFTISRDNSKNTLYL abc        90          100ab                110
2C4     ELRSLTFEDTAVYYCAR [NLGPSFYFDY]    WGQGTTLTVSS  (SEQ ID NO:2)
         ***   **                                **
574     QMNSLRAEDTAVYYCAR [NLGPSFYFDY]    WGQGTLVTVSS  (SEQ ID NO:4)
                                ******** hum III QMNSLRAEDTAVYYCAR [GRVGYSLYDY]    WGQGTLVTVSS  (SEQ ID NO:6)
```

FIG._2B

Amino Acid Sequence for Pertuzumab Light Chain

```
1          10         20         30         40         50         60
|          |          |          |          |          |          |
DIQMTQSPSSLSASVGDRVTITC KASQDVSIGVA WYQQKPGKAPKLLIY SASYRYT GVPS 70         80         90         100        110        120
           |          |          |          |          |          |
RFSGSGSGTDFTLTISSLQPEDFATYYC QQYYIYPYT FGQGTKVEIKRTVAAPSVFIFPP 130        140        150        160        170        180
           |          |          |          |          |          |
SDEQLKSGTASVVCLLNNFYPREAKVQWKVDNALQSGNSQESVTEQDSKDSTYSLSSTLT 190        200        210
           |          |          |
LSKADYEKHKVYACEVTHQGLSSPVTKSFNRGEC
```

FIG._3A

Amino Acid Sequence for Pertuzumab Heavy Chain

```
1          10         20         30         40         50         60
|          |          |          |          |          |          |
EVQLVESGGGLVQPGGSLRLSCAAS GFTFTDYTMD WVRQAPGKGLEWVA DVNPNSGGSIY 70         80         90         100        110        120
           |          |          |          |          |          |
NQRFK GRFTLSVDRSKNTLYLQMNSLRAEDTAVYYCARN LGPSFYFDY WGQGTLVTVSSA 130        140        150        160        170        180
           |          |          |          |          |          |
STKGPSVFPLAPSSKSTSGGTAALGCLVKDYFPEPVTVSWNSGALTSGVHTFPAVLQSSG 190        200        210        220        230        240
           |          |          |          |          |          |
LYSLSSVVTVPSSSLGTQTYICNVNHKPSNTKVDKKVEPKSCDKTHTCPPCPAPELLGGP 250        260        270        280        290        300
           |          |          |          |          |         *|
SVFLFPPKPKDTLMISRTPEVTCVVVDVSHEDPEVKFNWYVDGVEVHNAKTKPREEQYNS 310        320        330        340        350        360
           |          |          |          |          |          |
TYRVVSVLTVLHQDWLNGKEYKCKVSNKALPAPIEKTISKAKGQPREPQVYTLPPSREEM 370        380        390        400        410        420
           |          |          |          |          |          |
TKNQVSLTCLVKGFYPSDIAVEWESNGQPENNYKTTPPVLDSDGSFFLYSKLTVDKSRWQ 430        440        448
           |          |          |
QGNVFSCSVMHEALHNHYTQKSLSLSPG
```

FIG._3B

```
1                                            15                            30                             45
M G W S C I I F L F L V A T A T G V H S D I Q M T Q S P S S L S A S V G D R V T I T C K A S
46                                           60                            75                             90
Q D V S I G V A W Y Q Q K P G K A P K L L I Y S A S Y R Y T G V P S R F S G S G T D F
91                                           105                           120                            135
T L T I S S L Q P E D F A T Y Y C Q Q Y Y I Y P Y T F G Q G T K V E I K R T V A A P S V F
136                                          150                           165                            180
I F P P S D E Q L K S G T A S V V C L L N N F Y P R E A K V Q W K V D N A L Q S G N S Q E
181                                          195                           210                            225
S V T E Q D S K D S T Y S L S S T L T L S K A D Y E K H K V Y A C E V T H Q G L S S P V T
226      233
K S F N R G E C    (SEQ ID NO. 17)
```

FIG._4A

```
1   M G W S C I I F L V A T A T G V H S E V Q L V E S G G G L V Q P G G S L R L S C A A S G
46  F T F T D Y T M D W V R Q A P G K G L E W V A D V N P N S G G S I Y N Q R F K G R F T L S
91  V D R S K N T L Y L Q M N S L R A E D T A V Y Y C A R N L G P S F Y F D Y W G Q G T L V T
136 V S S A S T K G P S V F P L A P S S K S T S G G T A A L G C L V K D Y F P E P V T V S W N
181 S G A L T S G V H T F P A V L Q S S G L Y S L S S V V T V P S S S L G T Q T Y I C N V N H
226 K P S N T K V D K K V E P K S C D K T H T C P P C P A P E L L G G P S V F L F P P K P K D
271 T L M I S R T P E V T C V V V D V S H E D P E V K F N W Y V D G V E V H N A K T K P R E E
316 Q Y N S T Y R V V S V L T V L H Q D W L N G K E Y K C K V S N K A L P A P I E K T I S K A
361 K G Q P R E P Q V Y T L P P S R E E M T K N Q V S L T C L V K G F Y P S D I A V E W E S N
406 G Q P E N N Y K T T P P V L D S D G S F F L Y S K L T V D K S R W Q Q G N V F S C S V M H
451 E A L H N H Y T Q K S L S L S P G     (SEQ ID NO. 18)
```

*FIG._4B*

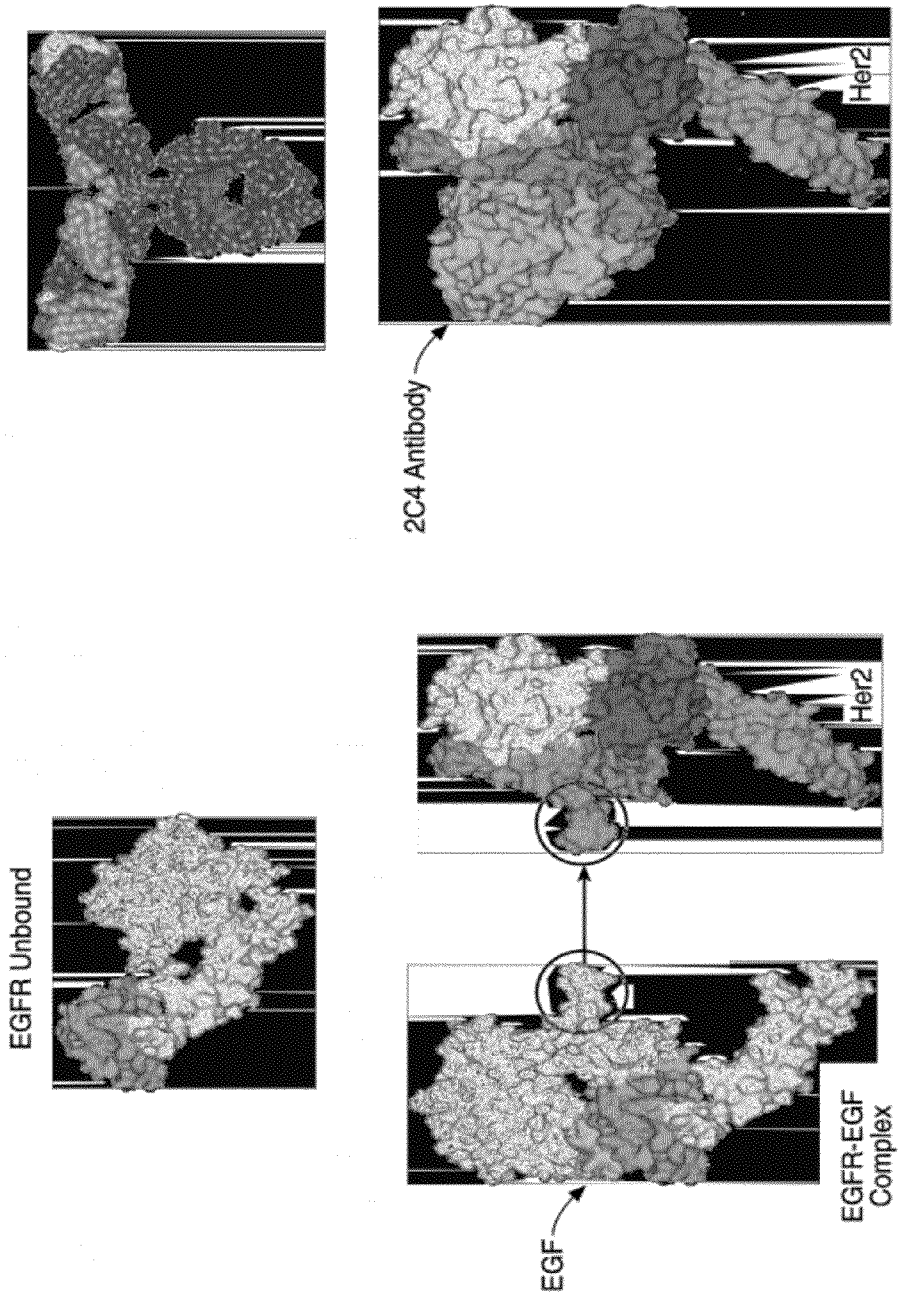
FIG._5

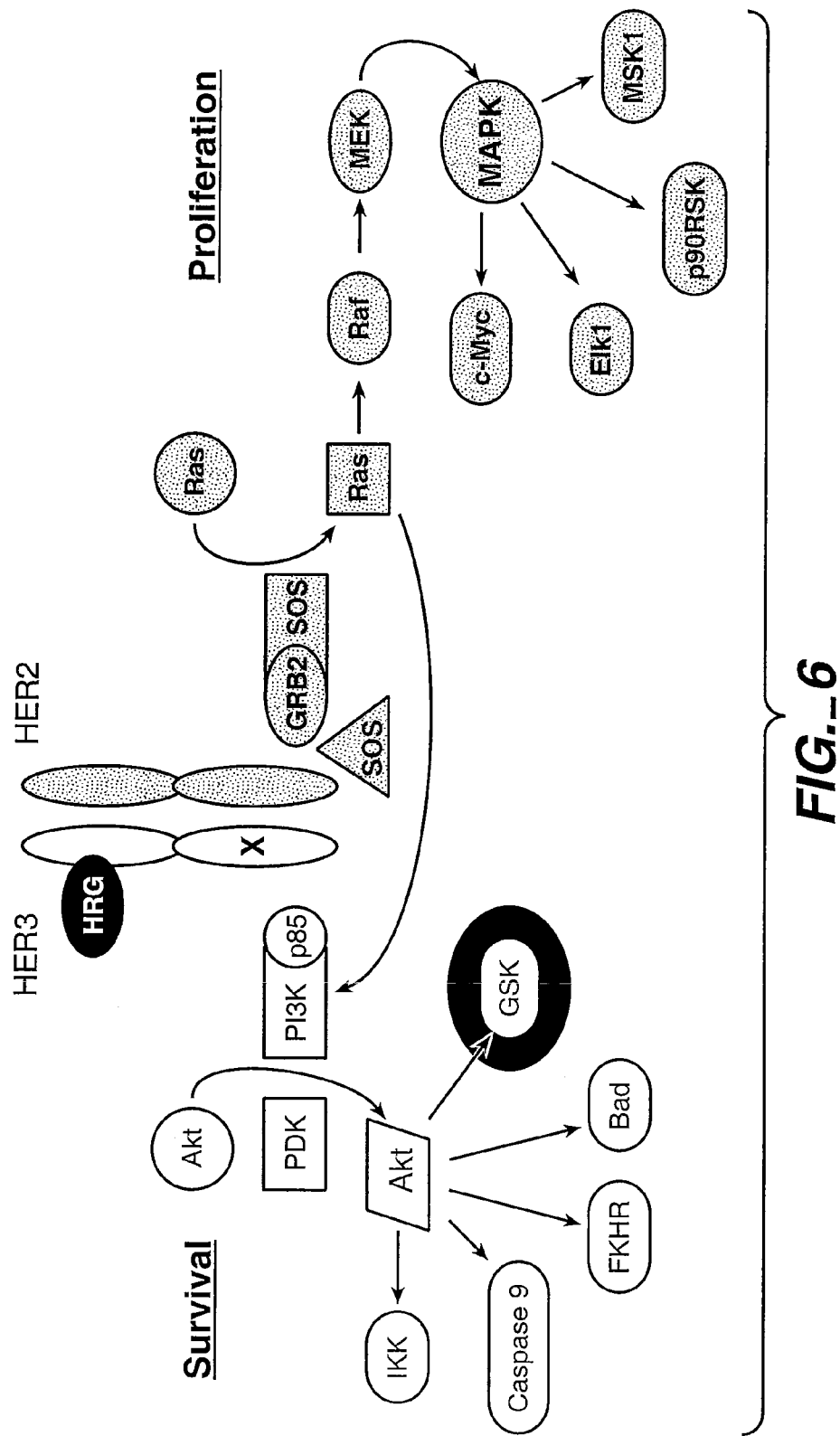
FIG._6

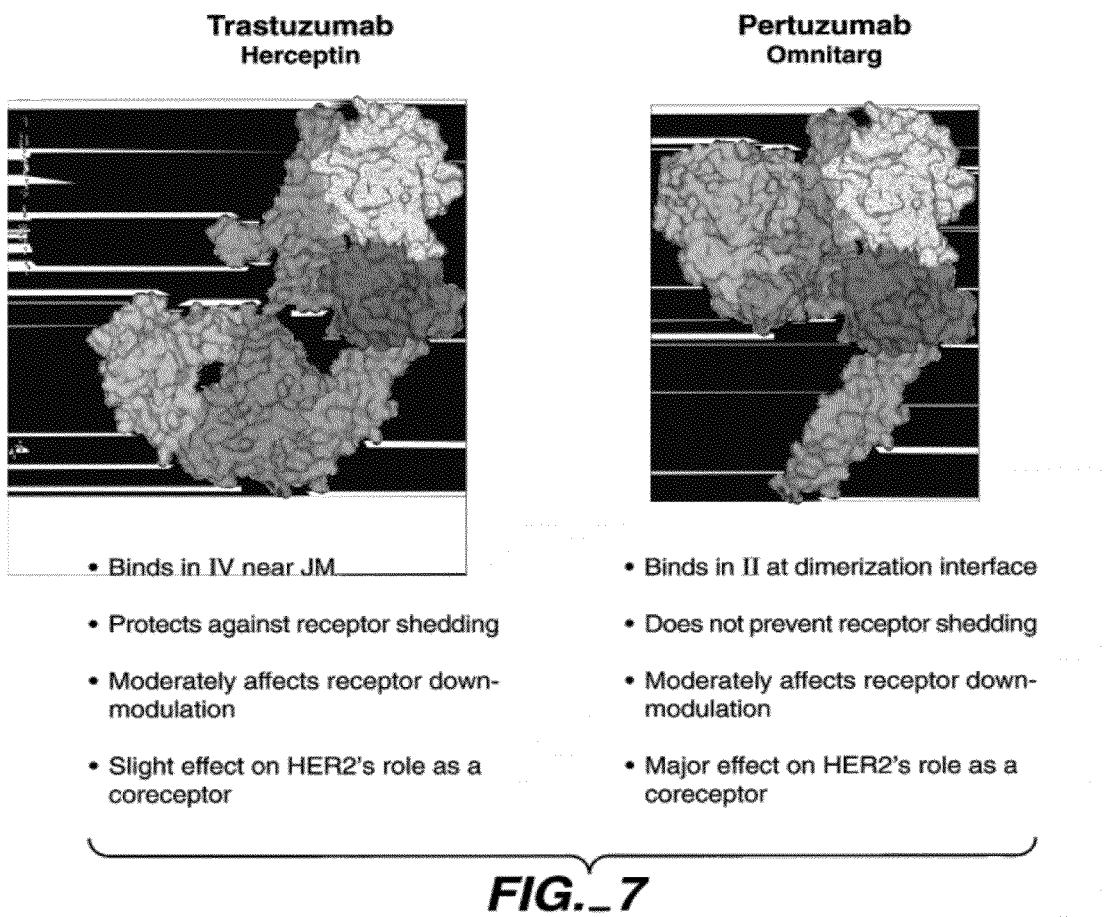
FIG._7

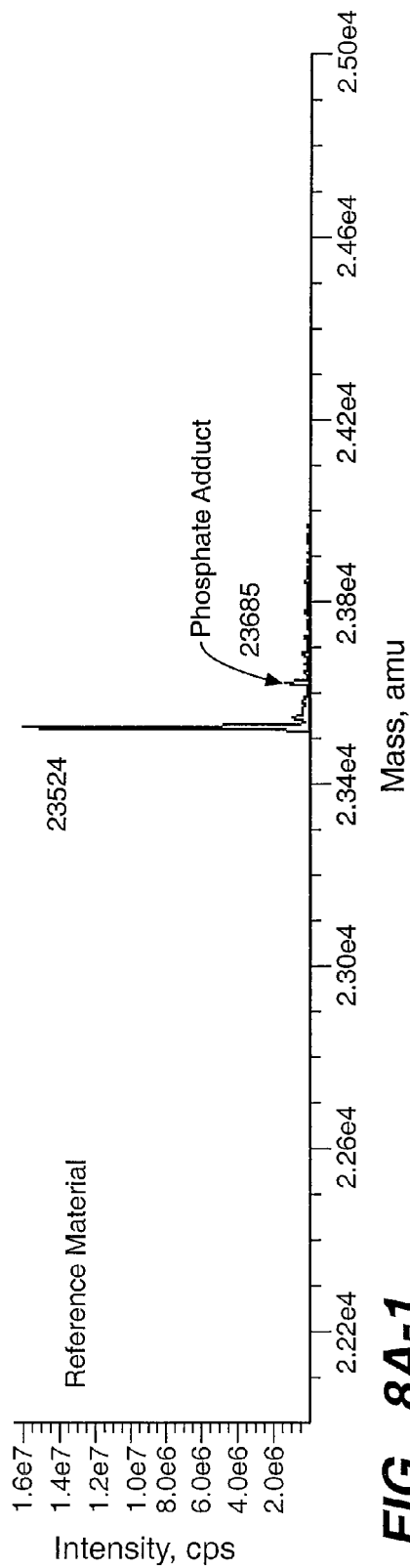
FIG._8A-1
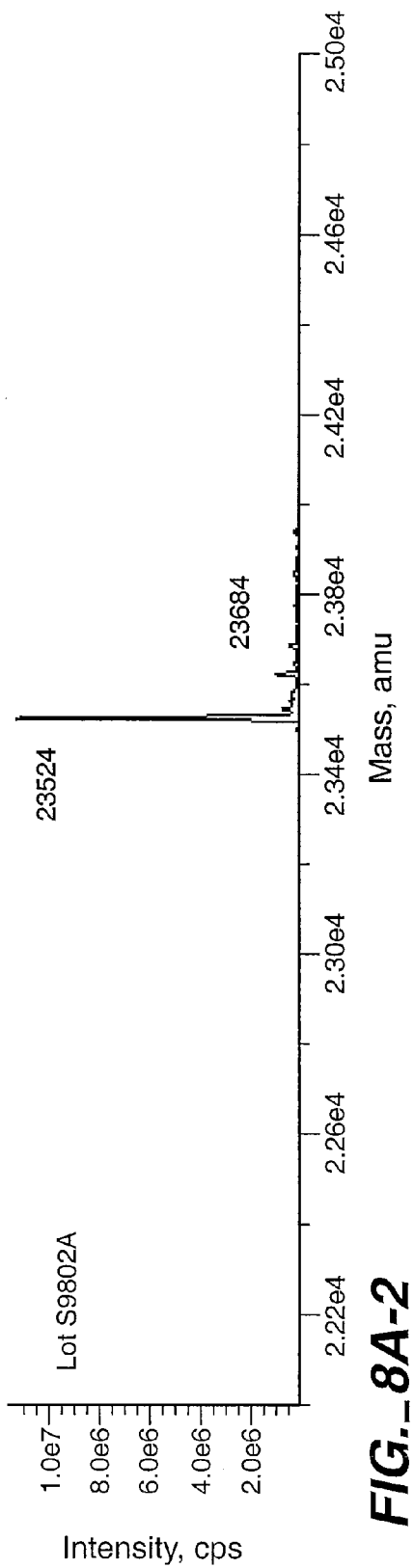
FIG._8A-2

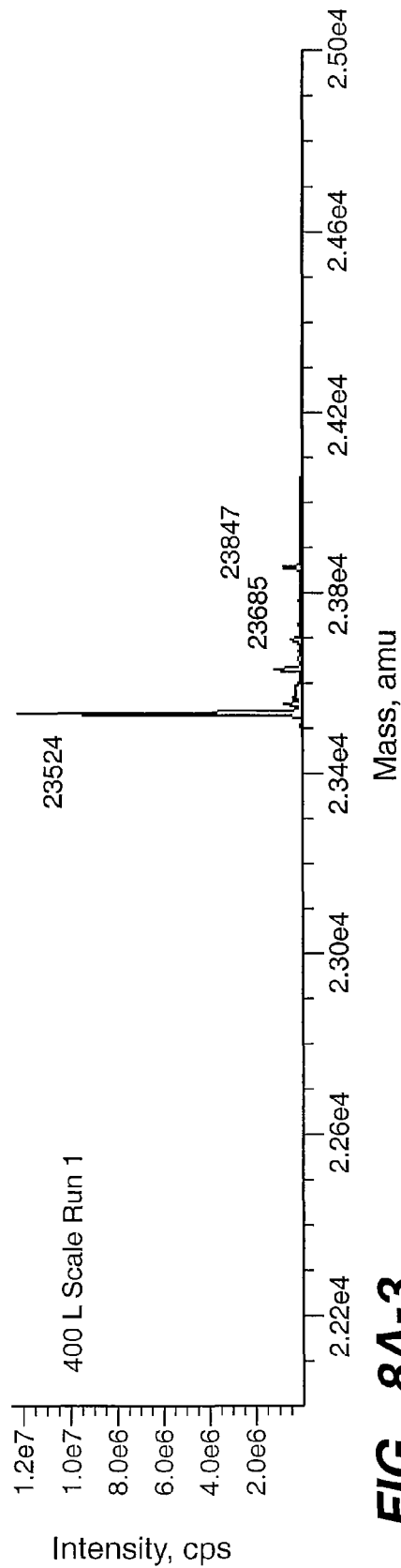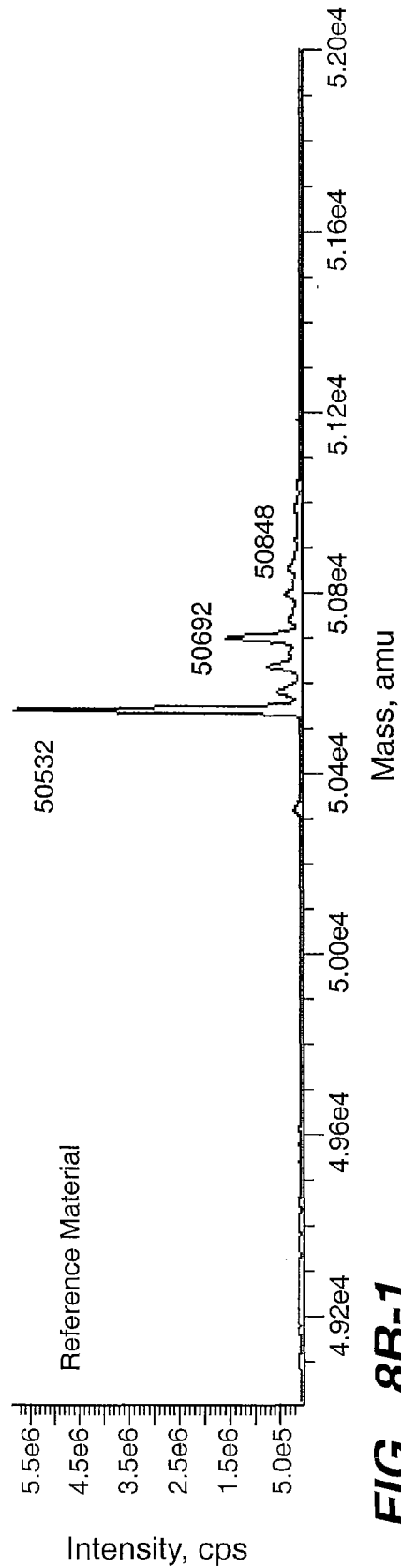
FIG._8A-3
FIG._8B-1

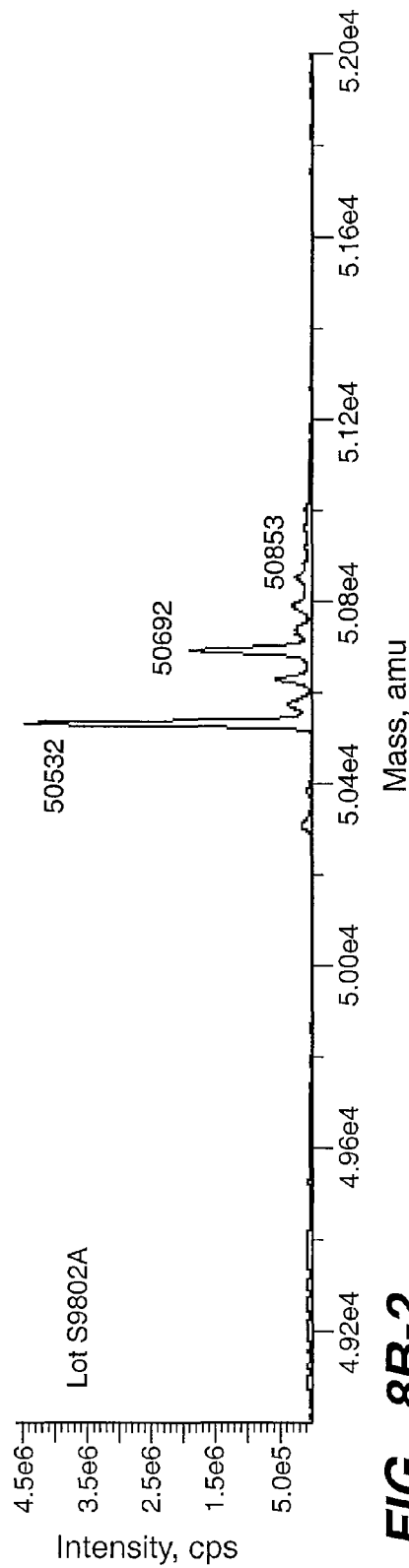
FIG._8B-2
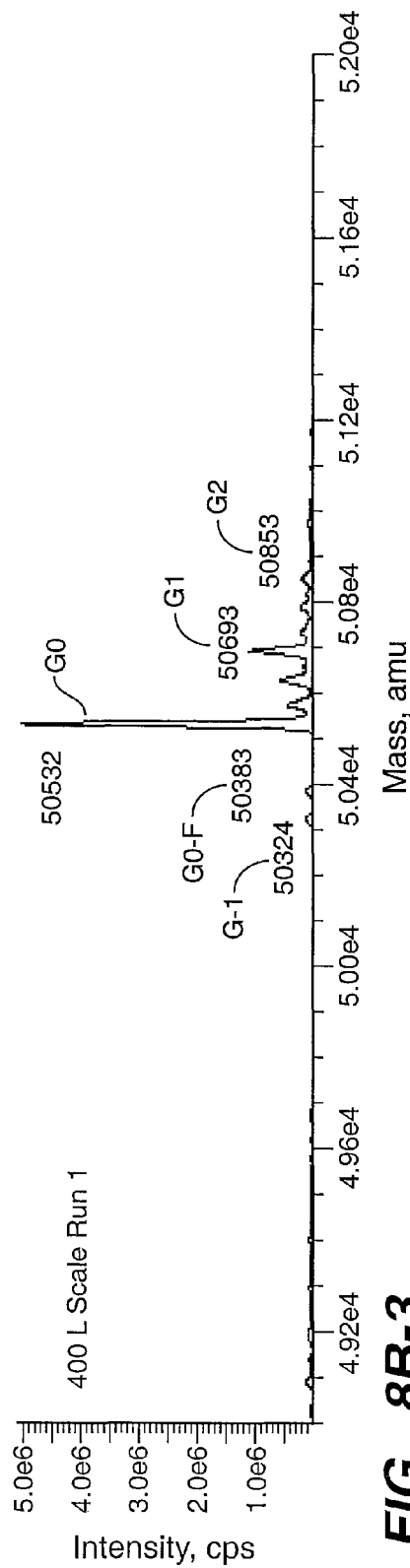
FIG._8B-3

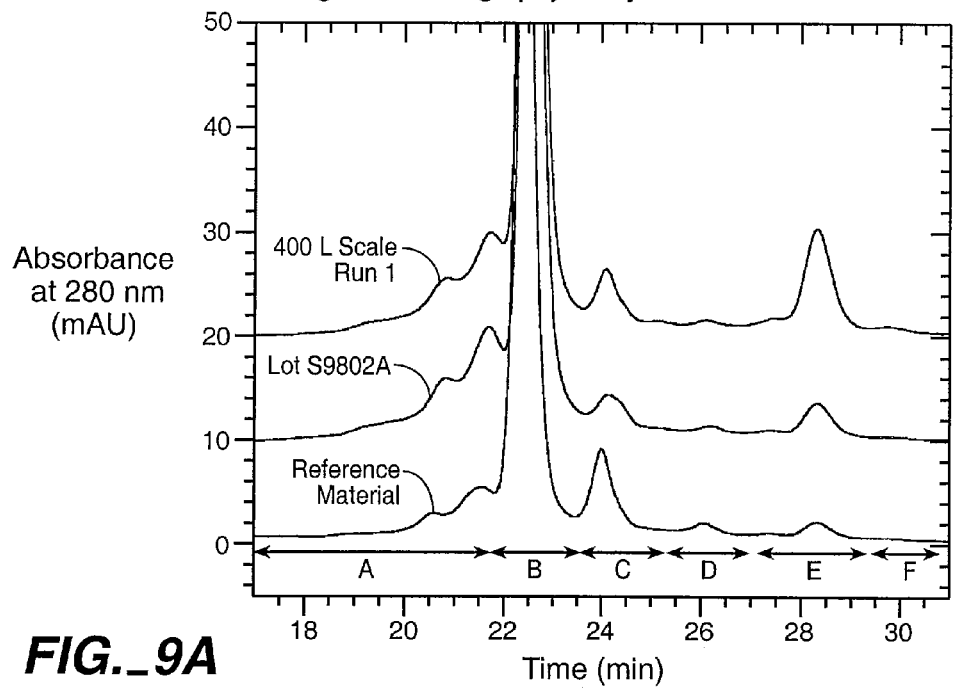
FIG._9A
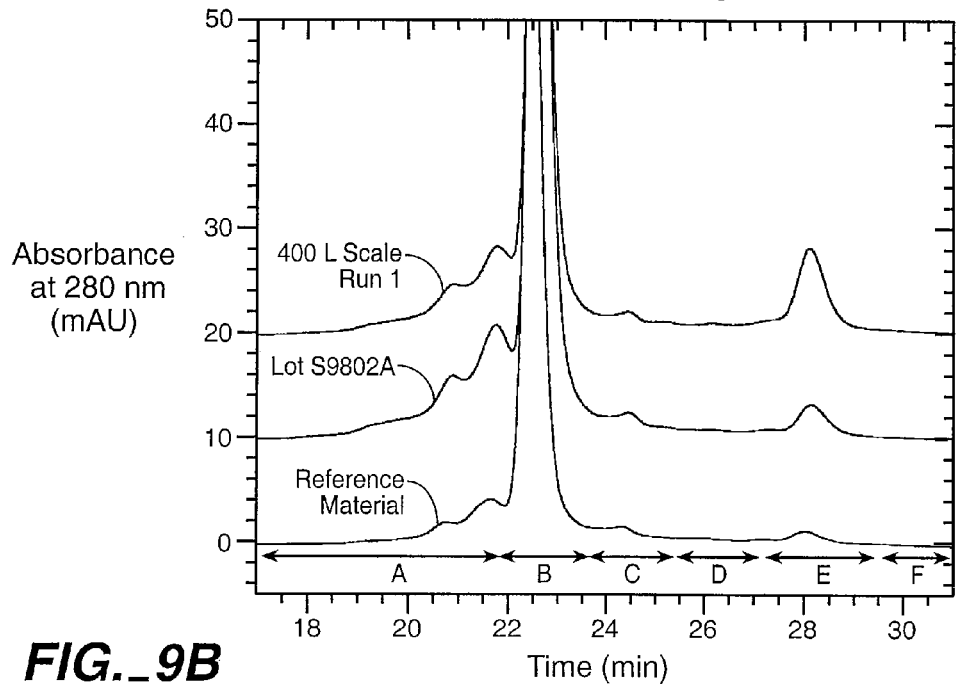
FIG._9B

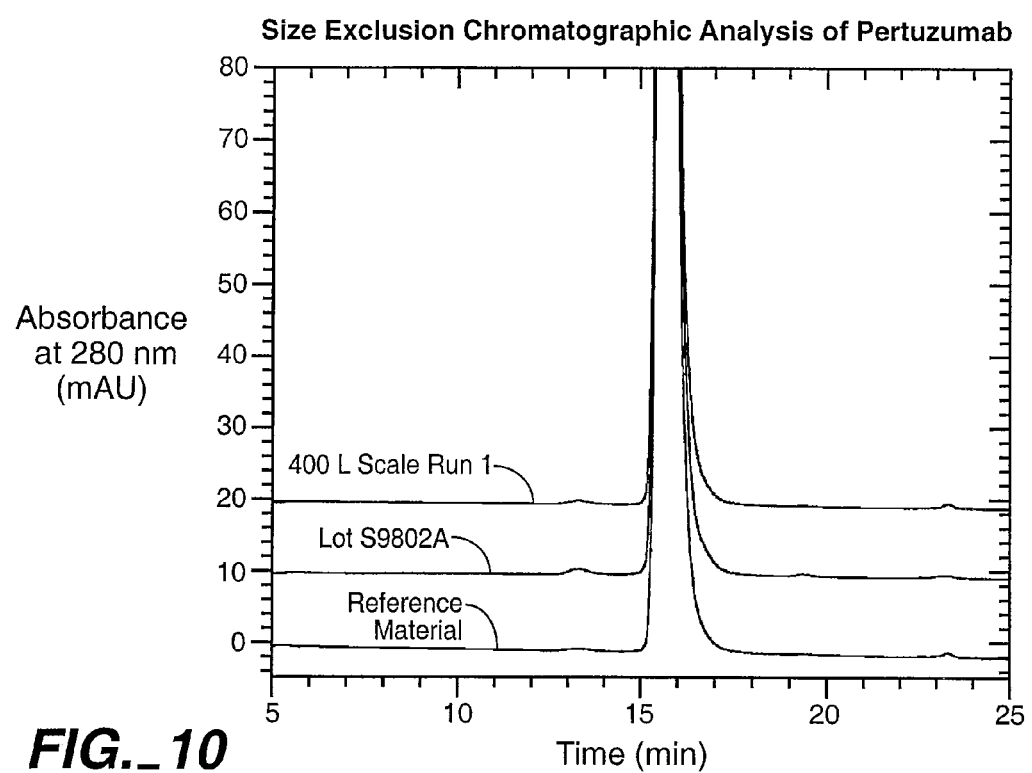
FIG._10

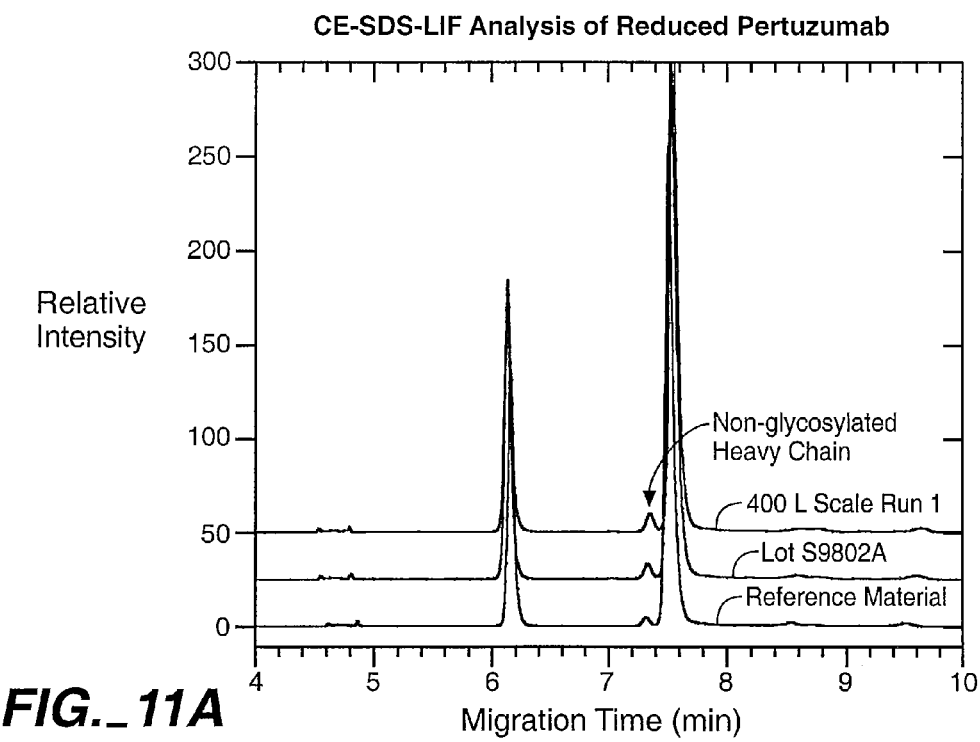
FIG._11A
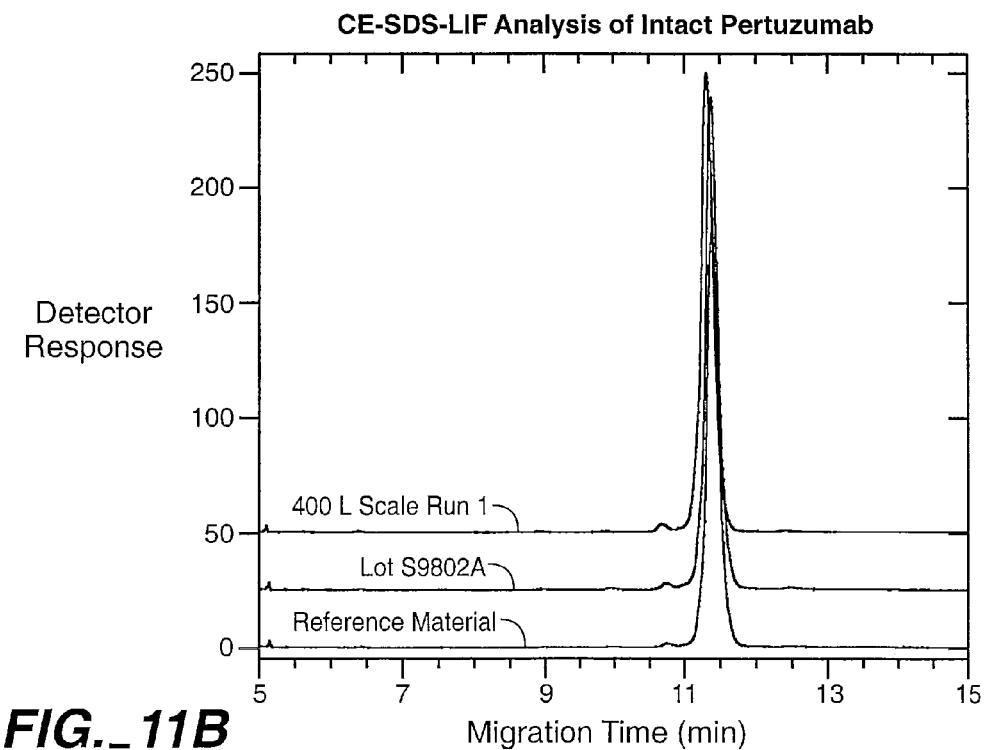
FIG._11B

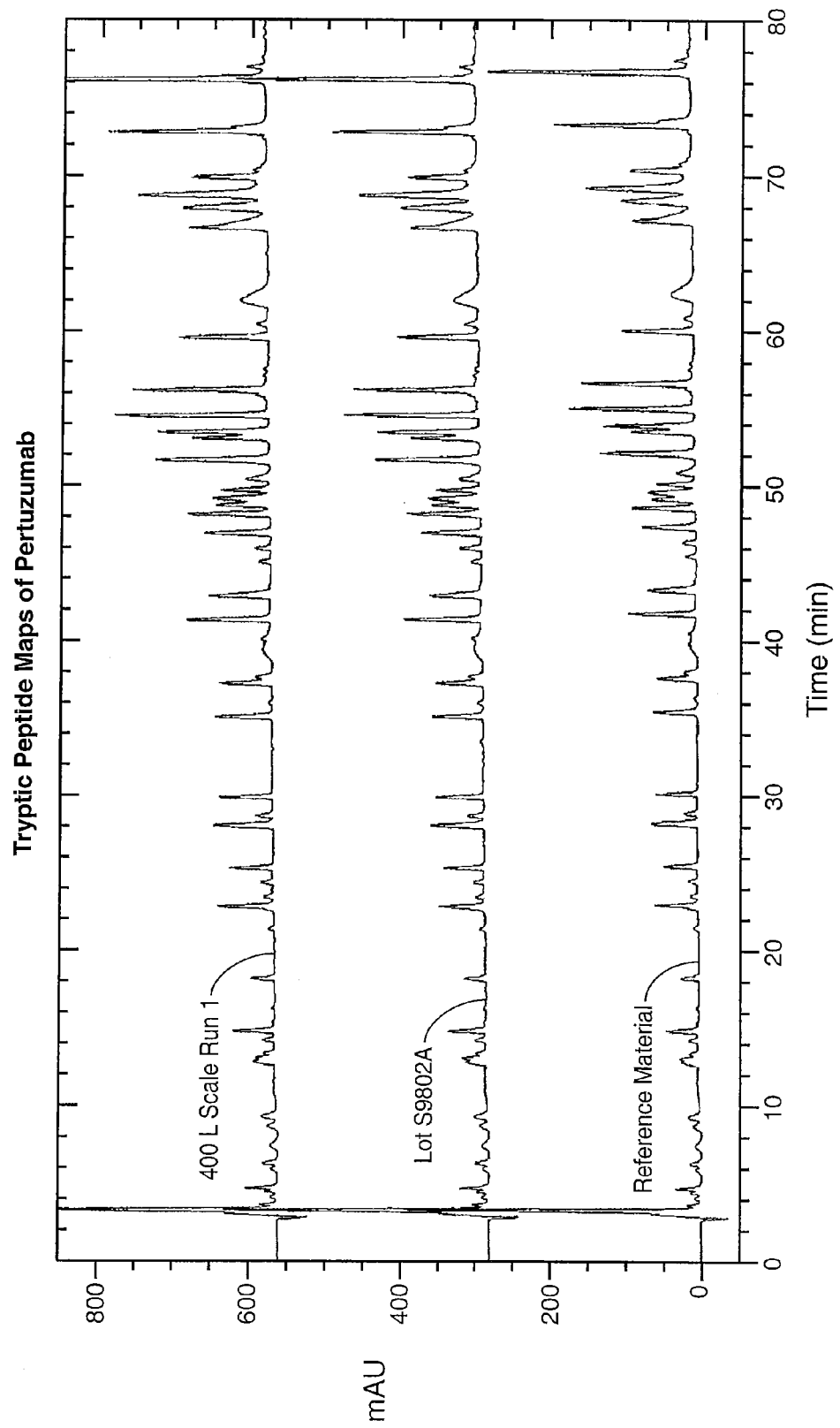
FIG._12A

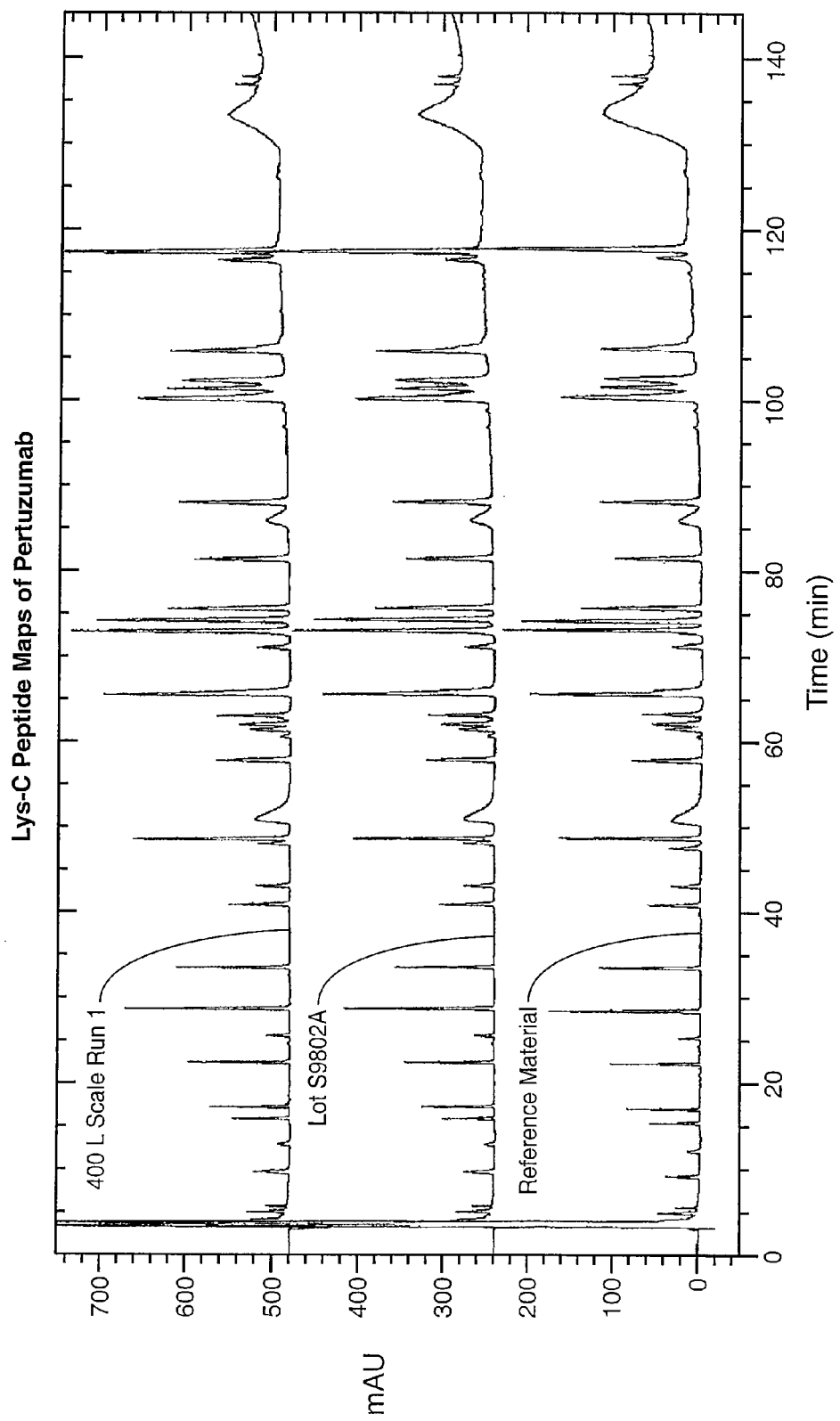
FIG._12B

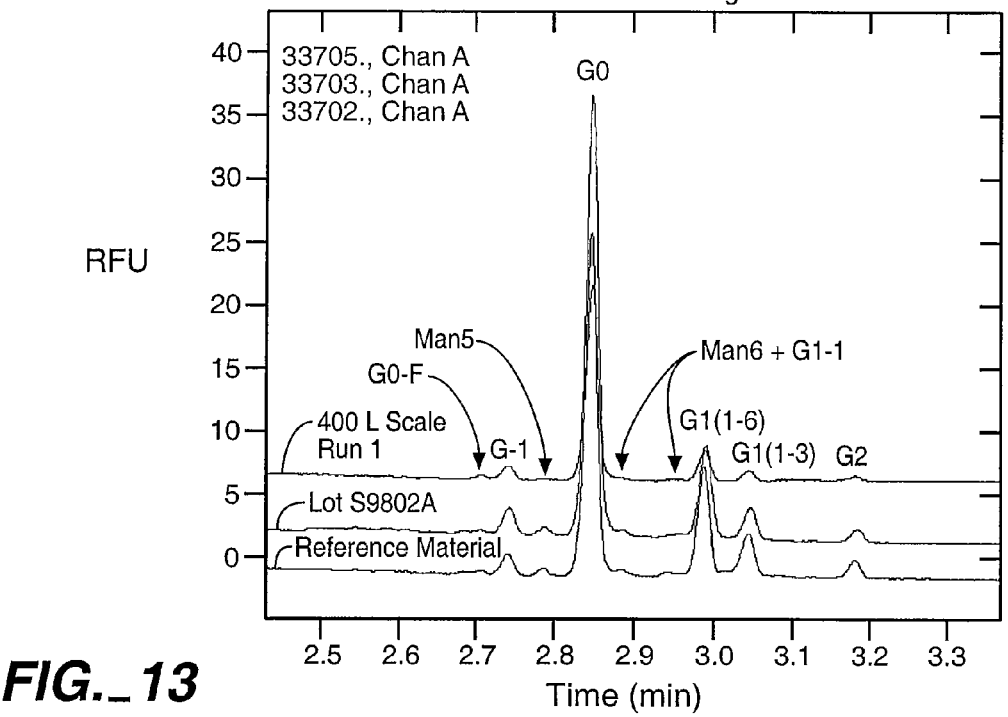
FIG._13
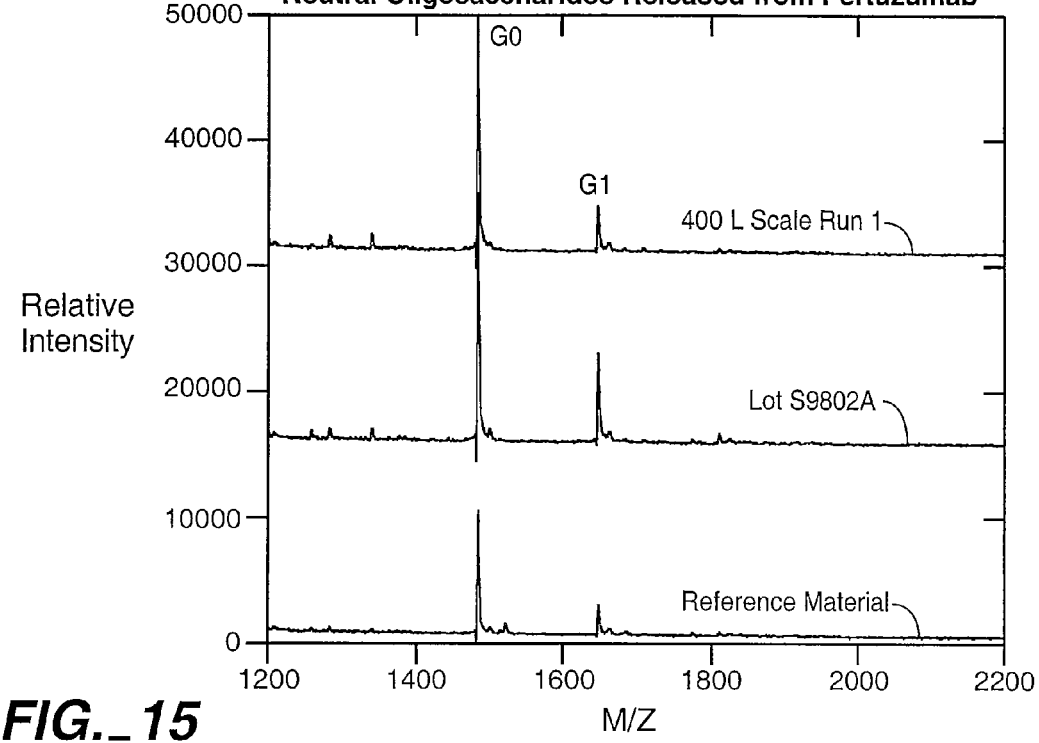
FIG._15

FIG. 14A

Oligosaccharide Structures Commonly Observed in IgG Antibodies

| Structures | Abbreviation | Mass |
|---|---|---|
| Manα(1→6)\Manα(1→6)\Manβ(1→4)GlcNAc-<br>Manα(1→3)/ Manα(1→3)/ | Man5 | 1235 |
| GlcNAcβ(1→2){Manα(1→6)\Manβ(1→4)GlcNAc-<br>   Manα(1→3)/  with Fucα(1→6) | G-1 | 1260 |
| GlcNAcβ(1→2)Manα(1→6)\Manβ(1→4)GlcNAc-<br>GlcNAcβ(1→2)Manα(1→3)/ | G0-F | 1317 |
| Manα(1→6)\Manα(1→6)\Manβ(1→4)GlcNAc-<br>Manα(1→3)/<br>Manα(1→2)Manα(1→3)/ | Man6 | 1398 |

Oligosaccharide Structures Commonly Observed in IgG Antibodies

| Structures | Abbreviation | Mass |
|---|---|---|
| Galβ(1→4)GlcNAcβ(1→2) { Manα(1→6) / Manα(1→3) } Manβ(1→4)GlcNAcβ(1→4)GlcNAc- with Fucα(1→6) | G1-1 | 1423 |
| GlcNAcβ(1→2)Manα(1→6) / GlcNAcβ(1→2)Manα(1→3) ⟩ Manβ(1→4)GlcNAcβ(1→4)GlcNAc- with Fucα(1→6) | G0 | 1463 |
| Galβ(1→4)GlcNAcβ(1→2)Manα(1→6) / GlcNAcβ(1→2)Manα(1→3) ⟩ Manβ(1→4)GlcNAcβ(1→4)GlcNAc- with Fucα(1→6) | G1 (1-6) | 1626 |
| GlcNAcβ(1→2)Manα(1→6) / Galβ(1→4)GlcNAcβ(1→2)Manα(1→3) ⟩ Manβ(1→4)GlcNAcβ(1→4)GlcNAc- with Fucα(1→6) | G1 (1-3) | 1626 |
| Galβ(1→4)GlcNAcβ(1→2)Manα(1→6) / Galβ(1→4)GlcNAcβ(1→2)Manα(1→3) ⟩ Manβ(1→4)GlcNAcβ(1→4)GlcNAc- with Fucα(1→6) | G2 | 1788 |

Masses shown in this figure correspond to the (M+Na)$^+$ values.

FIG. _14B

LIGHT CHAIN

```
1                           15                          30                          45
DIQMTQSPSSLSASVGDRVTITCRASQDVNTAVAWYQQKPGKAPK
46                          60                          75                          90
LLIYSASFLYSGVPSRFSGSRSGTDFTLTISSLQPEDFATYYCQQ
91                          105                         120                         135
HYTTPPTFGQGTKVEIKRTVAAPSVFIFPPSDEQLKSGTASVVCL
136                         150                         165                         180
LNNFYPREAKVQWKVDNALQSGNSQESVTEQDSKDSTYSLSSTLT
181                         195                         210  214
LSKADYEKHKVYACEVTHQGLSSPVTKSFNRGEC
```

FIG.–16A

HEAVY CHAIN

```
1   EVQLVESGGGLVQPGGSLRLSCAASGFNIKDTYIHWVRQAPGKGL            45
46  EWVARIYPTNGYTRYADSVKGRFTISADTSKNTAYLQMNSLRAED            90
91  TAVYYCSRWGGDGFYAMDYWGQGTLVTVSSASTKGPSVFPLAPSS            135
136 KSTSGGTAALGCLVKDYFPEPVTVSWNSGALTSGVHTFPAVLQSS            180
181 GLYSLSSVVTVPSSSLGTQTYICNVNHKPSNTKVDKKVEPKSCDK            225
226 THTCPPCPAPELLGGPSVFLFPPKPKDTLMISRTPEVTCVVVDVS            270
271 HEDPEVKFNWYVDGVEVHNAKTKPREEQYNSTYRVVSVLTVLHQD            315
316 WLNGKEYKCKVSNKALPAPIEKTISKAKGQPREPQVYTLPPSREE            360
361 MTKNQVSLTCLVKGFYPSDIAVEWESNGQPENNYKTTPPVLDSDG            405
406 SFFLYSKLTVDKSRWQQGNVFSCSVMHEALHNHYTQKSLSLSPG             449
```

FIG._16B

```
  1                                 15                    30                        45
  V  H  S  D  I  Q  M  T  Q  S  P  S  S  L  S  A  S  V  G  D  R  V  T  I  T  C  K  A  S  Q  D  V  S  I  G  V  A  W  Y  Q  Q  K  P  G  K
 46                                 60                    75                        90
  A  P  K  L  L  I  Y  S  A  S  Y  R  Y  T  G  V  P  S  R  F  S  G  S  G  S  G  T  D  F  T  L  T  I  S  S  L  Q  P  E  D  F  A  T  Y  Y
 91                                105                   120                       135
  C  Q  Q  Y  Y  I  Y  P  Y  T  F  G  Q  G  T  K  V  E  I  K  R  T  V  A  A  P  S  V  F  I  F  P  P  S  D  E  Q  L  K  S  G  T  A  S  V
136                                150                   165                       180
  V  C  L  L  N  N  F  Y  P  R  E  A  K  V  Q  W  K  V  D  N  A  L  Q  S  G  N  S  Q  E  S  V  T  E  Q  D  S  K  D  S  T  Y  S  L  S  S
181                                195                   210            217
  T  L  T  L  S  K  A  D  Y  E  K  H  K  V  Y  A  C  E  V  T  H  Q  G  L  S  S  P  V  T  K  S  F  N  R  G  E  C   (SEQ ID NO. 23)
```

FIG._17A

```
  1 EVQLVESGGGLVQPGGSLRLSCAASGFTFTDYTMDWVRQAPGKGL  45
 46 EWVADVNPNSGGSIYNQRFKGRFTLSVDRSKNTLYLQMNSLRAED  90
 91 TAVYYCARNLGPSFYFDYWGQGTLVTVSSASTKGPSVFPLAPSSK 135
136 STSGGTAALGCLVKDYFPEPVTVSWNSGALTSGVHTFPAVLQSSG 180
181 LYSLSSVVTVPSSSLGTQTYICNVNHKPSNTKVDKKVEPKSCDKT 225
226 HTCPPCPAPELLGGPSVFLFPPKPKDTLMISRTPEVTCVVVDVSH 270
271 EDPEVKFNWYVDGVEVHNAKTKPREEQYNSTYRVVSVLTVLHQDW 315
316 LNGKEYKCKVSNKALPAPIEKTISKAKGQPREPQVYTLPPSREEM 360
361 TKNQVSLTCLVKGFYPSDIAVEWESNGQPENNYKTTPPVLDSDGS 405
406 FFLYSKLTVDKSRWQQGNVFSCSVMHEALHNHYTQKSLSLSPGK  449
```

(SEQ ID NO. 24)

*FIG._17B*

HER2 ANTIBODY COMPOSITION

This is a divisional application which claims priority to divisional application Ser. No. 12/480,013, filed Jun. 8, 2009, which claims priority under 35 USC §120 to non-provisional application Ser. No. 11/182,908, filed Jul. 15, 2005 (now U.S. Pat. No. 7,560,111), which claims priority under 35 USC §119 to provisional application 60/590,202, filed Jul. 22, 2004, the contents of which are incorporated herein by reference.

FIELD OF THE INVENTION

The present invention concerns a composition comprising a main species HER2 antibody that binds to domain II of HER2, and an amino acid sequence variant thereof comprising an amino-terminal leader extension. The invention also relates to pharmaceutical formulations comprising the composition, and therapeutic uses for the composition.

BACKGROUND OF THE INVENTION

HER2 Antibodies

The HER family of receptor tyrosine kinases are important mediators of cell growth, differentiation and survival. The receptor family includes four distinct members including epidermal growth factor receptor (EGFR, ErbB1, or HER1), HER2 (ErbB2 or p185$^{neu}$), HER3 (ErbB3) and HER4 (ErbB4 or tyro2).

EGFR, encoded by the erbB 1 gene, has been causally implicated in human malignancy. In particular, increased expression of EGFR has been observed in breast, bladder, lung, head, neck and stomach cancer as well as glioblastomas. Increased EGFR receptor expression is often associated with increased production of the EGFR ligand, transforming growth factor alpha (TGF-α), by the same tumor cells resulting in receptor activation by an autocrine stimulatory pathway. Baselga and Mendelsohn *Pharmac. Ther.* 64:127-154 (1994). Monoclonal antibodies directed against the EGFR or its ligands, TGF-α and EGF, have been evaluated as therapeutic agents in the treatment of such malignancies. See, e.g., Baselga and Mendelsohn., supra; Masui et al. *Cancer Research* 44:1002-1007 (1984); and Wu et al. *J. Clin. Invest.* 95:1897-1905 (1995).

The second member of the HER family, p185$^{neu}$, was originally identified as the product of the transforming gene from neuroblastomas of chemically treated rats. The activated form of the neu proto-oncogene results from a point mutation (valine to glutamic acid) in the transmembrane region of the encoded protein. Amplification of the human homolog of neu is observed in breast and ovarian cancers and correlates with a poor prognosis (Slamon et al., *Science,* 235:177-182 (1987); Slamon et al., *Science,* 244:707-712 (1989); and U.S. Pat. No. 4,968,603). To date, no point mutation analogous to that in the neu proto-oncogene has been reported for human tumors. Overexpression of HER2 (frequently but not uniformly due to gene amplification) has also been observed in other carcinomas including carcinomas of the stomach, endometrium, salivary gland, lung, kidney, colon, thyroid, pancreas and bladder. See, among others, King et al., *Science,* 229:974 (1985); Yokota et al., *Lancet:* 1:765-767 (1986); Fukushige et al., *Mol Cell Biol.,* 6:955-958 (1986); Guerin et al., *Oncogene Res.,* 3:21-31 (1988); Cohen et al., *Oncogene,* 4:81-88 (1989); Yonemura et al., *Cancer Res.,* 51:1034 (1991); Borst et al., *Gynecol. Oncol.,* 38:364 (1990); Weiner et al., *Cancer Res.,* 50:421-425 (1990); Kern et al., *Cancer Res.,* 50:5184 (1990); Park et al., *Cancer Res.,* 49:6605 (1989); Zhau et al., *Mol. Carcinog.,* 3:254-257 (1990); Aasland et al. *Br. J. Cancer* 57:358-363 (1988); Williams et al. *Pathobiology* 59:46-52 (1991); and McCann et al., *Cancer,* 65:88-92 (1990). HER2 may be overexpressed in prostate cancer (Gu et al. *Cancer Lett.* 99:185-9 (1996); Ross et al. *Hum. Pathol.* 28:827-33 (1997); Ross et al. *Cancer* 79:2162-70 (1997); and Sadasivan et al. *J. Urol.* 150:126-31 (1993)).

Antibodies directed against the rat p185$^{neu}$ and human HER2 protein products have been described. Drebin and colleagues have raised antibodies against the rat neu gene product, p185$^{neu}$ See, for example, Drebin et al., *Cell* 41:695-706 (1985); Myers et al., *Meth. Enzym.* 198:277-290 (1991); and WO94/22478. Drebin et al. *Oncogene* 2:273-277 (1988) report that mixtures of antibodies reactive with two distinct regions of p185$^{new}$ result in synergistic anti-tumor effects on neu-transformed NIH-3T3 cells implanted into nude mice. See also U.S. Pat. No. 5,824,311 issued Oct. 20, 1998.

Hudziak et al., *Mol. Cell. Biol.* 9(3):1165-1172 (1989) describe the generation of a panel of HER2 antibodies which were characterized using the human breast tumor cell line SK-BR-3. Relative cell proliferation of the SK-BR-3 cells following exposure to the antibodies was determined by crystal violet staining of the monolayers after 72 hours. Using this assay, maximum inhibition was obtained with the antibody called 4D5 which inhibited cellular proliferation by 56%. Other antibodies in the panel reduced cellular proliferation to a lesser extent in this assay. The antibody 4D5 was further found to sensitize HER2-overexpressing breast tumor cell lines to the cytotoxic effects of TNF-α. See also U.S. Pat. No. 5,677,171 issued Oct. 14, 1997. The HER2 antibodies discussed in Hudziak et al. are further characterized in Fendly et al. *Cancer Research* 50:1550-1558 (1990); Kotts et al. *In Vitro* 26(3):59A (1990); Sarup et al. *Growth Regulation* 1:72-82 (1991); Shepard et al. *J. Clin. Immunol.* 11(3):117-127 (1991); Kumar et al. *Mol. Cell. Biol.* 11(2):979-986 (1991); Lewis et al. *Cancer Immunol. Immunother.* 37:255-263 (1993); Pietras et al. *Oncogene* 9:1829-1838 (1994); Vitetta et al. *Cancer Research* 54:5301-5309 (1994); Sliwkowski et al. *J. Biol. Chem.* 269(20):14661-14665 (1994); Scott et al. *J. Biol. Chem.* 266:14300-5 (1991); D'souza et al. *Proc. Natl. Acad. Sci.* 91:7202-7206 (1994); Lewis et al. *Cancer Research* 56:1457-1465 (1996); and Schaefer et al. *Oncogene* 15:1385-1394 (1997).

A recombinant humanized version of the murine HER2 antibody 4D5 (huMAb4D5-8, rhuMAb HER2, Trastuzumab or HERCEPTIN®; U.S. Pat. No. 5,821,337) is clinically active in patients with HER2-overexpressing metastatic breast cancers that have received extensive prior anti-cancer therapy (Baselga et al., *J. Clin. Oncol.* 14:737-744 (1996)). Trastuzumab received marketing approval from the Food and Drug Administration Sep. 25, 1998 for the treatment of patients with metastatic breast cancer whose tumors overexpress the HER2 protein.

Other HER2 antibodies with various properties have been described in Tagliabue et al. *Int. J. Cancer* 47:933-937 (1991); McKenzie et al. *Oncogene* 4:543-548 (1989); Maier et al. *Cancer Res.* 51:5361-5369 (1991); Bacus et al. *Molecular Carcinogenesis* 3:350-362 (1990); Stancovski et al. *PNAS (USA)* 88:8691-8695 (1991); Bacus et al. *Cancer Research* 52:2580-2589 (1992); Xu et al. *Int. J. Cancer* 53:401-408 (1993); WO94/00136; Kasprzyk et al. *Cancer Research* 52:2771-2776 (1992); Hancock et al. *Cancer Res.* 51:4575-4580 (1991); Shawver et al. *Cancer Res.* 54:1367-1373 (1994); Arteaga et al. *Cancer Res.* 54:3758-3765 (1994);

Harwerth et al. *J. Biol. Chem.* 267:15160-15167 (1992); U.S. Pat. No. 5,783,186; and Klapper et al. *Oncogene* 14:2099-2109 (1997).

Homology screening has resulted in the identification of two other HER receptor family members; HER3 (U.S. Pat. Nos. 5,183,884 and 5,480,968 as well as Kraus et al. *PNAS (USA)* 86:9193-9197 (1989)) and HER4 (EP Pat Appln No 599,274; Plowman et al., *Proc. Natl. Acad. Sci. USA*, 90:1746-1750 (1993); and Plowman et al., *Nature*, 366:473-475 (1993)). Both of these receptors display increased expression on at least some breast cancer cell lines.

The HER receptors are generally found in various combinations in cells and heterodimerization is thought to increase the diversity of cellular responses to a variety of HER ligands (Earp et al. *Breast Cancer Research and Treatment* 35: 115-132 (1995)). EGFR is bound by six different ligands; epidermal growth factor (EGF), transforming growth factor alpha (TGF-α), amphiregulin, heparin binding epidermal growth factor (HB-EGF), betacellulin and epiregulin (Groenen et al. *Growth Factors* 11:235-257 (1994)). A family of heregulin proteins resulting from alternative splicing of a single gene are ligands for HER3 and HER4. The heregulin family includes alpha, beta and gamma heregulins (Holmes et al., *Science*, 256:1205-1210 (1992); U.S. Pat. No. 5,641,869; and Schaefer et al. *Oncogene* 15:1385-1394 (1997)); neu differentiation factors (NDFs), glial growth factors (GGFs); acetylcholine receptor inducing activity (ARIA); and sensory and motor neuron derived factor (SMDF). For a review, see Groenen et al. *Growth Factors* 11:235-257 (1994); Lemke, G. *Molec. & Cell. Neurosci.* 7:247-262 (1996) and Lee et al. *Pharm. Rev.* 47:51-85 (1995). Recently three additional HER ligands were identified; neuregulin-2 (NRG-2) which is reported to bind either HER3 or HER4 (Chang et al. *Nature* 387 509-512 (1997); and Carraway et al *Nature* 387:512-516 (1997)); neuregulin-3 which binds HER4 (Zhang et al. *PNAS (USA)* 94(18):9562-7 (1997)); and neuregulin-4 which binds HER4 (Harari et al. *Oncogene* 18:2681-89 (1999)) HB-EGF, betacellulin and epiregulin also bind to HER4.

While EGF and TGFα do not bind HER2, EGF stimulates EGFR and HER2 to form a heterodimer, which activates EGFR and results in transphosphorylation of HER2 in the heterodimer. Dimerization and/or transphosphorylation appears to activate the HER2 tyrosine kinase. See Earp et al., supra. Likewise, when HER3 is co-expressed with HER2, an active signaling complex is formed and antibodies directed against HER2 are capable of disrupting this complex (Sliwkowski et al., *J. Biol. Chem.*, 269(20):14661-14665 (1994)). Additionally, the affinity of HER3 for heregulin (HRG) is increased to a higher affinity state when co-expressed with HER2. See also, Levi et al., *Journal of Neuroscience* 15: 1329-1340 (1995); Morrissey et al., *Proc. Natl. Acad. Sci. USA* 92: 1431-1435 (1995); and Lewis et al., *Cancer Res.*, 56:1457-1465 (1996) with respect to the HER2-HER3 protein complex. HER4, like HER3, forms an active signaling complex with HER2 (Carraway and Cantley, *Cell* 78:5-8 (1994)).

To target the HER signaling pathway, rhuMAb 2C4 (Pertuzumab, OMNITARG™) was developed as a humanized antibody that inhibits the dimerization of HER2 with other HER receptors, thereby inhibiting ligand-driven phosphorylation and activation, and downstream activation of the RAS and AKT pathways. In a phase I trial of Pertuzumab as a single agent for treating solid tumors, 3 subjects with advanced ovarian cancer were treated with pertuzumab. One had a durable partial response, and an additional subject had stable disease for 15 weeks. Agus et al. *Proc Am Soc Clin. Oncol* 22: 192, Abstract 771 (2003).

Antibody Variant Compositions

U.S. Pat. No. 6,339,142 describes a HER2 antibody composition comprising a mixture of anti-HER2 antibody and one or more acidic variants thereof, wherein the amount of the acidic variant(s) is less than about 25%. Trastuzumab is the exemplified HER2 antibody.

Reid et al. Poster presented at Well Characterized Biotech Pharmaceuticals conference (January, 2003) "Effects of Cell Culture Process Changes on Humanized Antibody Characteristics" describes an unnamed, humanized IgG1 antibody composition with N-terminal heterogeneities due to combinations of VHS signal peptide, N-terminal glutamine, and pyroglutamic acid on the heavy chain thereof.

Reed et al. "The Ideal Chromatographic Antibody Characterization Method" Poster presented at the IBC Antibody Production Conference (February, 2002) reports a VHS extension on the heavy chain of E25, a humanized anti-IgE antibody.

Rouse et al. Poster presented at WCBP "'Top Down' Glycoprotein Characterization by High Resolution Mass Spectrometry and Its Application to Biopharmaceutical Development" (Jan. 6-9, 2004) describes a monoclonal antibody composition with N-terminal heterogeneity resulting from $^{-3}$AHS or $^{-2}$HS signal peptide residues on the light chain thereof.

In a presentation at IBC Meeting (September, 2000) "Strategic Use of Comparability Studies and Assays for Well Characterized Biologicals," Jill Porter discussed a late-eluting form of ZENAPAX™ with three extra amino acid residues on the heavy chain thereof.

SUMMARY OF THE INVENTION

The present invention concerns a composition comprising a main species HER2 antibody that binds to domain II of HER2, and an amino acid sequence variant thereof comprising an amino-terminal leader extension.

In addition, the invention provides a composition comprising a mixture of a main species HER2 antibody comprising variable light and variable heavy sequences in SEQ ID Nos. 3 and 4, respectively, and an amino acid sequence variant of the main species antibody comprising a VHS-amino-terminal leader extension attached to one or two variable light domains thereof, wherein from about 1% to about 20% of antibody molecules in the composition comprise a VHS-amino-terminal leader extension.

The invention further concerns a polypeptide comprising the amino acid sequence in SEQ ID No. 23, or a deamidated and/or oxidized variant thereof, as well as an antibody comprising (a) a light chain comprising that polypeptide, and (b) a heavy chain comprising an amino acid sequence selected from the group consisting of SEQ ID NO. 16, SEQ ID NO. 24, and a deamidated and/or oxidized variant of SEQ ID NO. 16 or SEQ ID NO. 24.

The invention also concerns a pharmaceutical formulation comprising the composition in a pharmaceutically acceptable carrier, and a method of treating HER2-expressing cancer in a patient comprising administering the pharmaceutical formulation to the patient in an amount effective to treat the cancer.

BRIEF DESCRIPTION OF THE DRAWINGS

FIG. 1 provides a schematic of the HER2 protein structure, and amino acid sequences for Domains I-IV (SEQ ID Nos. 19-22, respectively) of the extracellular domain thereof.

FIGS. 2A and 2B depict alignments of the amino acid sequences of the variable light ($V_L$) (FIG. 2A) and variable heavy ($V_H$) (FIG. 2B) domains of murine monoclonal antibody 2C4 (SEQ ID Nos. 1 and 2, respectively); $V_L$ and $V_H$ domains of humanized 2C4 version 574 (SEQ ID Nos. 3 and 4, respectively), and human $V_L$ and $V_H$ consensus frameworks (hum κ1, light kappa subgroup I; humIII, heavy subgroup III) (SEQ ID Nos. 5 and 6, respectively). Asterisks identify differences between humanized 2C4 version 574 and murine monoclonal antibody 2C4 or between humanized 2C4 version 574 and the human framework. Complementarity Determining Regions (CDRs) are in brackets.

FIGS. 3A and 3B show the amino acid sequences of Pertuzumab light chain (SEQ ID No. 15) and heavy chain (SEQ ID No. 16). CDRs are shown in bold. The carbohydrate moiety is attached to Asn 299 of the heavy chain.

FIGS. 4A and 4B show the amino acid sequences of Pertuzumab light chain (SEQ ID No. 17) and heavy chain, each including an intact amino terminal signal peptide sequence (SEQ ID No. 18).

FIG. 5 depicts, schematically, binding of 2C4 at the heterodimeric binding site of HER2, thereby preventing heterodimerization with activated EGFR or HER3.

FIG. 6 depicts coupling of HER2/HER3 to the MAPK and Akt pathways.

FIG. 7 compares activities of Trastuzumab and Pertuzumab.

FIGS. 8A-1, 8A-2, 8A-3, 8B-1, 8B-2 and 8B-3 show reconstructed mass spectra of reduced Pertuzumab light chain (FIGS. 8A-1, 8A-2 and 8A-3) and heavy chain (FIGS. 8B-1, 8B-2 and 8B-3).

FIGS. 9A and 9B depict cation exchange chromatography analysis of native Pertuzumab (FIG. 9A) and CPB-digested Pertuzumab (FIG. 9B).

FIG. 10 shows size exclusion chromatographic analysis of Pertuzumab.

FIGS. 11A and 11B show CE-SDS-LIF analysis of reduced Pertuzumab (FIG. 11A) and intact Pertuzumab (FIG. 11B).

FIGS. 12A and 12B depict tryptic peptide maps of Pertuzumab (FIG. 12A), and LYS-C peptide maps of Pertuzumab (FIG. 12B).

FIG. 13 shows CE analysis of N-linked oligosaccharides released from Pertuzumab.

FIGS. 14A and 14B show oligosaccharide structures commonly observed in IgG antibodies.

FIG. 15 depicts positive mode MALDI-TOF mass spectra of neutral oligosaccharides released from Pertuzumab.

FIGS. 16A and 16B show the amino acid sequences of Trastuzumab light chain (SEQ ID No. 13) and heavy chain (SEQ ID No. 14).

FIGS. 17A and 17B depict a variant Pertuzumab light chain sequence (SEQ ID No. 23) and a variant Pertuzumab heavy chain sequence (SEQ ID No. 24).

DETAILED DESCRIPTION OF THE PREFERRED EMBODIMENTS

I. Definitions

The term "main species antibody" herein refers to the antibody amino acid sequence structure in a composition which is the quantitatively predominant antibody molecule in the composition. Preferably, the main species antibody is a HER2 antibody, such as an antibody that binds to Domain II of HER2, antibody that inhibits HER dimerization more effectively than Trastuzumab, and/or an antibody which binds to a heterodimeric binding site of HER2. The preferred embodiment herein of the main species antibody is one comprising the variable light and variable heavy amino acid sequences in SEQ ID Nos. 3 and 4, and most preferably comprising the light chain and heavy chain amino acid sequences in SEQ ID Nos. 15 and 16 (Pertuzumab).

An "amino acid sequence variant" antibody herein is an antibody with an amino acid sequence which differs from a main species antibody. Ordinarily, amino acid sequence variants will possess at least about 70% homology with the main species antibody, and preferably, they will be at least about 80%, and more preferably at least about 90% homologous with the main species antibody. The amino acid sequence variants possess substitutions, deletions, and/or additions at certain positions within or adjacent to the amino acid sequence of the main species antibody. Examples of amino acid sequence variants herein include an acidic variant (e.g. a deamidated antibody variant), a basic variant, the antibody with an amino-terminal leader extension (e.g. VHS-) on one or two light chains thereof, antibody with a C-terminal lysine residue on one or two heavy chains thereof, antibody with one or more oxidized methionine residues, etc. and includes combinations of variations to the amino acid sequences of heavy and/or light chains. The antibody variant of particular interest herein is the antibody comprising an amino-terminal leader extension on one or two light chains thereof, optionally further comprising other amino acid sequence and/or glycosylation differences relative to the main species antibody.

A "glycosylation variant" antibody herein is an antibody with one or more carbohydrate moeities attached thereto which differ from one or more carbohydrate moieties attached to a main species antibody. Examples of glycosylation variants herein include antibody with a G1 or G2 oligosaccharide structure, instead a G0 oligosaccharide structure, attached to an Fc region thereof, antibody with one or two carbohydrate moieties attached to one or two light chains thereof, antibody with no carbohydrate attached to one or two heavy chains of the antibody, etc., as well as combinations of such glycosylation alterations.

Where the antibody has an Fc region, an oligosaccharide structure such as that shown in FIG. 14 herein may be attached to one or two heavy chains of the antibody, e.g. at residue 299. For Pertuzumab, G0 was the predominant oligosaccharide structure, with other oligosaccharide structures such as G0-F, G-1, Man5, Man6, G1-1, G1(1-6), G1(1-3) and G2 being found in lesser amounts in the Pertuzumab composition.

Unless indicated otherwise, a "G1 oligosaccharide structure" herein includes G1(1-6) and G1(1-3) structures.

An "amino-terminal leader extension" herein refers to one or more amino acid residues of the amino-terminal leader sequence that are present at the amino-terminus of any one or more heavy or light chains of an antibody. An exemplary amino-terminal leader extension comprises or consists of three amino acid residues, VHS, present on one or both light chains of an antibody variant.

A "deamidated" antibody is one in which one or more asparagine residues thereof has been derivatized, e.g. to an aspartic acid, a succinimide, or an iso-aspartic acid.

"Homology" is defined as the percentage of residues in the amino acid sequence variant that are identical after aligning the sequences and introducing gaps, if necessary, to achieve the maximum percent homology. Methods and computer programs for the alignment are well known in the art. One such computer program is "Align 2", authored by Genentech, Inc., which was filed with user documentation in the United States Copyright Office, Washington, D.C. 20559, on Dec. 10, 1991.

For the purposes herein, "cation exchange analysis" refers to any method by which a composition comprising two or more compounds is separated based on charge differences using a cation exchanger. A cation exchanger generally comprises covalently bound, negatively charged groups. Preferably, the cation exchanger herein is a weak cation-exchanger and/or comprises a carboxylate functional group, such as the PROPAC WCX-10™ cation exchange column sold by Dionex.

A "HER receptor" is a receptor protein tyrosine kinase which belongs to the HER receptor family and includes EGFR, HER2, HER3 and HER4 receptors and other members of this family to be identified in the future. The HER receptor will generally comprise an extracellular domain, which may bind an HER ligand; a lipophilic transmembrane domain; a conserved intracellular tyrosine kinase domain; and a carboxyl-terminal signaling domain harboring several tyrosine residues which can be phosphorylated. Preferably the HER receptor is native sequence human HER receptor.

The extracellular domain of HER2 comprises four domains, Domain I (amino acid residues from about 1-195), Domain II (amino acid residues from about 196-319), Domain III (amino acid residues from about 320-488), and Domain IV (amino acid residues from about 489-630) (residue numbering without signal peptide). See Garrett et al. *Mol. Cell.* 11: 495-505 (2003), Cho et al. *Nature* 421: 756-760 (2003), Franklin et al. *Cancer Cell* 5:317-328 (2004), or Plowman et al. *Proc. Natl. Acad. Sci.* 90:1746-1750 (1993). See, also, FIG. 1 herein.

The terms "ErbB1," "HER1", "epidermal growth factor receptor" and "EGFR" are used interchangeably herein and refer to EGFR as disclosed, for example, in Carpenter et al. *Ann. Rev. Biochem.* 56:881-914 (1987), including naturally occurring mutant forms thereof (e.g. a deletion mutant EGFR as in Humphrey et al. *PNAS (USA)* 87:4207-4211 (1990)). erbB1 refers to the gene encoding the EGFR protein product.

The expressions "ErbB2" and "HER2" are used interchangeably herein and refer to human HER2 protein described, for example, in Semba et al., *PNAS (USA)* 82:6497-6501 (1985) and Yamamoto et al. *Nature* 319:230-234 (1986) (Genebank accession number X03363). The term "erbB2" refers to the gene encoding human ErbB2 and "neu" refers to the gene encoding rat p185$^{neu}$. Preferred HER2 is native sequence human HER2.

"ErbB3" and "HER3" refer to the receptor polypeptide as disclosed, for example, in U.S. Pat. Nos. 5,183,884 and 5,480,968 as well as Kraus et al. *PNAS (USA)* 86:9193-9197 (1989).

The terms "ErbB4" and "HER4" herein refer to the receptor polypeptide as disclosed, for example, in EP Pat Appin No 599,274; Plowman et al., *Proc. Natl. Acad. Sci. USA,* 90:1746-1750 (1993); and Plowman et al., *Nature,* 366:473-475 (1993), including isoforms thereof, e.g., as disclosed in WO99/19488, published Apr. 22, 1999.

By "HER ligand" is meant a polypeptide which binds to and/or activates an HER receptor. The HER ligand of particular interest herein is a native sequence human HER ligand such as epidermal growth factor (EGF) (Savage et al., *J. Biol. Chem.* 247:7612-7621 (1972)); transforming growth factor alpha (TGF-α) (Marquardt et al., *Science* 223:1079-1082 (1984)); amphiregulin also known as schwanoma or keratinocyte autocrine growth factor (Shoyab et al. *Science* 243: 1074-1076 (1989); Kimura et al. *Nature* 348:257-260 (1990); and Cook et al. *Mol. Cell. Biol.* 11:2547-2557 (1991)); betacellulin (Shing et al., *Science* 259:1604-1607 (1993); and Sasada et al. *Biochem. Biophys. Res. Commun.* 190:1173 (1993)); heparin-binding epidermal growth factor (HB-EGF) (Higashiyama et al., *Science* 251:936-939 (1991)); epiregulin (Toyoda et al., *J. Biol. Chem.* 270:7495-7500 (1995); and Komurasaki et al. *Oncogene* 15:2841-2848 (1997)); a heregulin (see below); neuregulin-2 (NRG-2) (Carraway et al., *Nature* 387:512-516 (1997)); neuregulin-3 (NRG-3) (Zhang et al., *Proc. Natl. Acad. Sci.* 94:9562-9567 (1997)); neuregulin-4 (NRG-4) (Harari et al. *Oncogene* 18:2681-89 (1999)) or cripto (CR-1) (Kannan et al. *J. Biol. Chem.* 272(6):3330-3335 (1997)). HER ligands which bind EGFR include EGF, TGF-α, amphiregulin, betacellulin, HB-EGF and epiregulin. HER ligands which bind HER3 include heregulins. HER ligands capable of binding HER4 include betacellulin, epiregulin, HB-EGF, NRG-2, NRG-3, NRG-4 and heregulins.

"Heregulin" (HRG) when used herein refers to a polypeptide encoded by the heregulin gene product as disclosed in U.S. Pat. No. 5,641,869 or Marchionni et al., *Nature,* 362: 312-318 (1993). Examples of heregulins include heregulin-α, heregulin-β1, heregulin-β2 and heregulin-β3 (Holmes et al., *Science,* 256:1205-1210 (1992); and U.S. Pat. No. 5,641, 869); neu differentiation factor (NDF) (Peles et al. *Cell* 69: 205-216 (1992)); acetylcholine receptor-inducing activity (ARIA) (Falls et al. *Cell* 72:801-815 (1993)); glial growth factors (GGFs) (Marchionni et al., *Nature,* 362:312-318 (1993)); sensory and motor neuron derived factor (SMDF) (Ho et al. *J. Biol. Chem.* 270:14523-14532 (1995)); γ-heregulin (Schaefer et al. *Oncogene* 15:1385-1394 (1997)). The term includes biologically active fragments and/or amino acid sequence variants of a native sequence HRG polypeptide, such as an EGF-like domain fragment thereof (e.g. HRGβ1$_{177-244}$).

A "HER dimer" herein is a noncovalently associated dimer comprising at least two different HER receptors. Such complexes may form when a cell expressing two or more HER receptors is exposed to an HER ligand and can be isolated by immunoprecipitation and analyzed by SDS-PAGE as described in Sliwkowski et al., *J. Biol. Chem.,* 269(20): 14661-14665 (1994), for example. Examples of such HER dimers include EGFR-HER2, HER2-HER3 and HER3-HER4 heterodimers. Moreover, the HER dimer may comprise two or more HER2 receptors combined with a different HER receptor, such as HER3, HER4 or EGFR. Other proteins, such as a cytokine receptor subunit (e.g. gp130) may be associated with the dimer.

A "heterodimeric binding site" on HER2, refers to a region in the extracellular domain of HER2 that contacts, or interfaces with, a region in the extracellular domain of EGFR, HER3 or HER4 upon formation of a dimer therewith. The region is found in Domain II of HER2. Franklin et al. *Cancer Cell* 5:317-328 (2004).

"HER activation" or "HER2 activation" refers to activation, or phosphorylation, of any one or more HER receptors, or HER2 receptors. Generally, HER activation results in signal transduction (e.g. that caused by an intracellular kinase domain of a HER receptor phosphorylating tyrosine residues in the HER receptor or a substrate polypeptide). HER activation may be mediated by HER ligand binding to a HER dimer comprising the HER receptor of interest. HER ligand binding to a HER dimer may activate a kinase domain of one or more of the HER receptors in the dimer and thereby results in phosphorylation of tyrosine residues in one or more of the HER receptors and/or phosphorylation of tyrosine residues in additional substrate polypeptides(s), such as Akt or MAPK intracellular kinases.

The term "antibody" herein is used in the broadest sense and specifically covers intact monoclonal antibodies, polyclonal antibodies, multispecific antibodies (e.g. bispecific antibodies) formed from at least two intact antibodies, and antibody fragments, so long as they exhibit the desired biological activity.

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such as those variants described herein. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA*, 81:6851-6855 (1984)). Chimeric antibodies of interest herein include "primatized" antibodies comprising variable domain antigen-binding sequences derived from a non-human primate (e.g. Old World Monkey, Ape etc) and human constant region sequences.

"Antibody fragments" comprise a portion of an intact antibody, preferably comprising the antigen-binding or variable region thereof. Examples of antibody fragments include Fab, Fab', F(ab')$_2$, and Fv fragments; diabodies; linear antibodies; single-chain antibody molecules; and multispecific antibodies formed from antibody fragment(s).

An "intact antibody" is one which comprises an antigen-binding variable region as well as a light chain constant domain ($C_L$) and heavy chain constant domains, $C_H1$, $C_H2$ and $C_H3$. The constant domains may be native sequence constant domains (e.g. human native sequence constant domains) or amino acid sequence variants thereof. Preferably, the intact antibody has one or more effector functions, and comprises an oligosaccharide structure attached to one or two heavy chains thereof.

Antibody "effector functions" refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc.

Depending on the amino acid sequence of the constant domain of their heavy chains, intact antibodies can be assigned to different "classes". There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS* (*USA*) 95:652-656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

The terms "Fc receptor" or "FcR" are used to describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

"Complement dependent cytotoxicity" or "CDC" refers to the ability of a molecule to lyse a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods* 202:163 (1996), may be performed.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheetstructure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994). HER2 antibody scFv fragments are described in WO93/16185; U.S. Pat. No. 5,571,894; and U.S. Pat. No. 5,587,458.

The term "diabodies" refers to small antibody fragments with two antigen-binding sites, which fragments comprise a variable heavy domain ($V_H$) connected to a variable light domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

Humanized HER2 antibodies include huMAb4D5-1, huMAb4D5-2, huMAb4D5-3, huMAb4D5-4, huMAb4D5-5, huMAb4D5-6, huMAb4D5-7 and huMAb4D5-8 or Trastuzumab (HERCEPTIN®) as described in Table 3 of U.S. Pat. No. 5,821,337 expressly incorporated herein by reference; humanized 520C9 (WO93/21319) and humanized 2C4 antibodies as described herein.

For the purposes herein, "Trastuzumab," "HERCEPTIN®," and "huMAb4D5-8" refer to an antibody comprising the light and heavy chain amino acid sequences in SEQ ID NOS. 13 and 14, respectively.

Herein, "Pertuzumab," "OMNITARG™," and "rhuMAb 2C4," refer to an antibody comprising the variable light and variable heavy amino acid sequences in SEQ ID Nos. 3 and 4, respectfully. Where Pertuzumab is an intact antibody, it preferably comprises the light chain and heavy chain amino acid sequences in SEQ ID Nos. 15 and 16, respectively.

A "naked antibody" is an antibody (as herein defined) that is not conjugated to a heterologous molecule, such as a cytotoxic moiety or radiolabel.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

A HER2 antibody which "inhibits HER2 dimerization more effectively than Trastuzumab" is one which reduces or eliminates HER dimers more effectively (for example at least about 2-fold more effectively) than Trastuzumab. Preferably, such an antibody inhibits HER2 dimerization at least about as effectively as an antibody selected from the group consisting of intact murine monoclonal antibody 2C4, a Fab fragment of murine monoclonal antibody 2C4, intact Pertuzumab, and a Fab fragment of Pertuzumab. One can evaluate HER dimerization inhibition by studying HER dimers directly, or by evaluating HER activation, or downstream signaling, which results from HER dimerization, and/or by evaluating the antibody-HER2 binding site, etc. Assays for screening for antibodies with the ability to inhibit HER dimerization more effectively than Trastuzumab are described in Agus et al. *Cancer Cell* 2: 127-137 (2002) and WO01/00245 (Adams et al.). By way of example only, one may assay for inhibition of HER dimerization by assessing, for example, inhibition of HER dimer formation (see, e.g., FIG. 1A-B of Agus et al. *Cancer Cell* 2: 127-137 (2002); and WO01/00245); reduction in HER ligand activation of cells which express HER dimers (WO01/00245 and FIG. 2A-B of Agus et al. *Cancer Cell* 2: 127-137 (2002), for example); blocking of HER ligand binding to cells which express HER dimers (WO01/00245, and FIG. 2E of Agus et al. *Cancer Cell* 2: 127-137 (2002), for example); cell growth inhibition of cancer cells (e.g. MCF7, MDA-MD-134, ZR-75-1, MD-MB-175, T-47D cells) which express HER dimers in the presence (or absence) of HER ligand (WO01/00245 and FIGS. 3A-D of Agus et al. *Cancer Cell* 2: 127-137 (2002), for instance); inhibition of downstream signaling (for instance, inhibition of HRG-dependent AKT phosphorylation or inhibition of HRG- or TGFα-dependent MAPK phosphorylation) (see, WO01/00245, and FIG. 2C-D of Agus et al. *Cancer Cell* 2: 127-137 (2002), for example). One may also assess whether the antibody inhibits HER dimerization by studying the antibody-HER2 binding site, for instance, by evaluating a structure or model, such as a crystal structure, of the antibody bound to HER2 (See, for example, Franklin et al. *Cancer Cell* 5:317-328 (2004)).

The HER2 antibody may "inhibit HRG-dependent AKT phosphorylation" and/or inhibit "HRG- or TGFα-dependent MAPK phosphorylation" more effectively (for instance at least 2-fold more effectively) than Trastuzumab (see Agus et al. *Cancer Cell* 2: 127-137 (2002) and WO01/00245, by way of example).

The HER2 antibody may be one which does "not inhibit HER2 ectodomain cleavage" (Molina et al. *Cancer Res.* 61:4744-4749 (2001)).

A HER2 antibody that "binds to a heterodimeric binding site" of HER2, binds to residues in domain II (and optionally also binds to residues in other of the domains of the HER2 extracellular domain, such as domains I and III), and can steric ally hinder, at least to some extent, formation of a HER2-EGFR, HER2-HER3, or HER2-HER4 heterodimer. Franklin et al. *Cancer Cell* 5:317-328 (2004) characterize the HER2-Pertuzumab crystal structure, deposited with the RCSB Protein Data Bank (ID Code IS78), illustrating an exemplary antibody that binds to the heterodimeric binding site of HER2.

An antibody that "binds to domain II" of HER2 binds to residues in domain II and optionally residues in other domain(s) of HER2, such as domains I and III. Preferably the antibody that binds to domain II binds to the junction between domains I, II and III of HER2.

A "growth inhibitory agent" when used herein refers to a compound or composition which inhibits growth of a cell, especially a HER expressing cancer cell either in vitro or in vivo. Thus, the growth inhibitory agent may be one which significantly reduces the percentage of HER expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13.

Examples of "growth inhibitory" antibodies are those which bind to HER2 and inhibit the growth of cancer cells overexpressing HER2. Preferred growth inhibitory HER2 antibodies inhibit growth of SK-BR-3 breast tumor cells in cell culture by greater than 20%, and preferably greater than 50% (e.g. from about 50% to about 100%) at an antibody concentration of about 0.5 to 30 μg/ml, where the growth inhibition is determined six days after exposure of the SK-BR-3 cells to the antibody (see U.S. Pat. No. 5,677,171 issued Oct. 14, 1997). The SK-BR-3 cell growth inhibition assay is described in more detail in that patent and hereinbelow. The preferred growth inhibitory antibody is a humanized variant of murine monoclonal antibody 4D5, e.g., Trastuzumab.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses the HER2 receptor. Preferably the cell is a tumor cell, e.g. a breast, ovarian, stomach, endometrial, salivary gland, lung, kidney, colon, thyroid, pancreatic or bladder cell. In vitro, the cell may be a SK-BR-3, BT474, Calu 3 cell, MDA-MB-453, MDA-MB-361 or SKOV3 cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold, induction of annexin binding relative to untreated cell in an annexin binding assay using BT474 cells (see below). Examples of HER2 antibodies that induce apoptosis are 7C2 and 7F3.

The "epitope 2C4" is the region in the extracellular domain of HER2 to which the antibody 2C4 binds. In order to screen for antibodies which bind to the 2C4 epitope, a routine cross-blocking assay such as that described in Antibodies, A Laboratory Manual, Cold Spring Harbor Laboratory, Ed Harlow and David Lane (1988), can be performed. Alternatively, epitope mapping can be performed to assess whether the antibody binds to the 2C4 epitope of HER2 using methods known in the art and/or one can study the antibody-HER2 structure (Franklin et al. *Cancer Cell* 5:317-328 (2004)) to see what domain(s) of HER2 is/are bound by the antibody. Epitope 2C4 comprises residues from domain II in the extracellular domain of HER2. 2C4 and Pertuzumab bind to the extracellular domain of HER2 at the junction of domains I, II and III. Franklin et al. *Cancer Cell* 5:317-328 (2004).

The "epitope 4D5" is the region in the extracellular domain of HER2 to which the antibody 4D5 (ATCC CRL 10463) and Trastuzumab bind. This epitope is close to the transmembrane domain of HER2, and within Domain IV of HER2. To screen for antibodies which bind to the 4D5 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to assess whether the antibody binds to the 4D5 epitope of HER2 (e.g. any one or more residues in the region from about residue 529 to about residue 625, inclusive, in FIG. 1).

The "epitope 7C2/7F3" is the region at the N terminus, within Domain I, of the extracellular domain of HER2 to which the 7C2 and/or 7F3 antibodies (each deposited with the ATCC, see below) bind. To screen for antibodies which bind to the 7C2/7F3 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to establish whether the antibody binds to the 7C2/7F3 epitope on HER2 (e.g. any one or more of residues in the region from about residue 22 to about residue 53 of HER2 in FIG. 1).

"Treatment" refers to both therapeutic treatment and prophylactic or preventative measures. Those in need of treatment include those already with the disease as well as those in which the disease is to be prevented. Hence, the patient to be treated herein may have been diagnosed as having the disease or may be predisposed or susceptible to the disease.

The terms "cancer" and "cancerous" refer to or describe the physiological condition in mammals that is typically characterized by unregulated cell growth. Examples of cancer include, but are not limited to, carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, as well as head and neck cancer.

The term "effective amount" refers to an amount of a drug effective to treat disease in the patient. Where the disease is cancer, the effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The effective amount may extend progression free survival, result in an objective response (including a partial response, PR, or complete response, CR), increase overall survival time, and/or improve one or more symptoms of cancer.

A "HER2-expressing cancer" is one comprising cells which have HER2 protein present at their cell surface.

A cancer which "overexpresses" a HER receptor is one which has significantly higher levels of a HER receptor, such as HER2, at the cell surface thereof, compared to a noncancerous cell of the same tissue type. Such overexpression may be caused by gene amplification or by increased transcription or translation. HER receptor overexpression may be determined in a diagnostic or prognostic assay by evaluating increased levels of the HER protein present on the surface of a cell (e.g. via an immunohistochemistry assay; IHC). Alternatively, or additionally, one may measure levels of HER-encoding nucleic acid in the cell, e.g. via fluorescent in situ hybridization (FISH; see WO98/45479 published October, 1998), southern blotting, or polymerase chain reaction (PCR) techniques, such as real time quantitative PCR(RT-PCR). One may also study HER receptor overexpression by measuring shed antigen (e.g., HER extracellular domain) in a biological fluid such as serum (see, e.g., U.S. Pat. No. 4,933, 294 issued Jun. 12, 1990; WO91/05264 published Apr. 18, 1991; U.S. Pat. No. 5,401,638 issued Mar. 28, 1995; and Sias et al. *J. Immunol. Methods* 132: 73-80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

Conversely, a cancer which "does not overexpress HER2 receptor" is one which does not express higher than normal levels of HER2 receptor compared to a noncancerous cell of the same tissue type. A cancer which "overexpresses" a HER ligand is one which produces significantly higher levels of that ligand compared to a noncancerous cell of the same tissue type. Such overexpression may be caused by gene amplification or by increased transcription or translation. Overexpression of the HER ligand may be determined diagnostically by evaluating levels of the ligand (or nucleic acid encoding it) in the patient, e.g. in a tumor biopsy or by various diagnostic assays such as the IHC, FISH, southern blotting, PCR or in vivo assays described above.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $B^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega11 (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®)), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chlorambucil; 6-thioguanine; mercaptopurine; methotrexate; platinum agents such as cisplatin, oxaliplatin, and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovovin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN@ vaccine, and VAXID® vaccine; topoisomerase 1 inhibitor (e.g., LURTOTECAN®); rmRH (e.g., ABARELIX®); BAY439006 (sorafenib; Bayer); SU-11248 (Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN') combined with 5-FU and leucovovin.

Also included in this definition are anti-hormonal agents that act to regulate or inhibit hormone action on tumors such as anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors such as anastrazole (ARIMIDEX®), letrozole (FEMARA®) and aminoglutethimide, and other aromatase inhibitors including vorozole (RIVISOR®), megestrol acetate (MEGASE®), fadrozole, imidazole; lutenizing hormone-releasing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; testolactone; and pharmaceutically acceptable salts, acids or derivatives of any of the above; as well as combinations of two or more of the above.

As used herein, the term "EGFR-targeted drug" refers to a therapeutic agent that binds to EGFR and, optionally, inhibits EGFR activation. Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. Eur. J. Cancer 32A: 636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6, 3 and described in U.S. Pat. No. 6,235,883; MDX-447 (Medarex Inc); and mAb 806 or humanized mAb 806 (Johns et al., J. Biol. Chem. 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA™) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N-8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Sugen); AG1571 (SU 5271; Sugen); dual EGFR/HER2 tyrosine kinase inhibitors such as lapatinib (GW 572016 or N-[3-chloro-4-[(3 fluorophenyl) methoxy]phenyl]6[5[[[2-methylsulfonyl)ethyl]amino]methyl]-2-furanyl]-4-quinazolinamine; Glaxo-SmithKline) or cyanoguanidine quinazoline and cyanoamidine quinazolamine derivatives.

A "tyrosine kinase inhibitor" is a molecule which inhibits tyrosine kinase activity of a tyrosine kinase such as a HER receptor. Examples of such inhibitors include the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GW572016; available from Glaxo-SmithKline) an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibits Raf-1 signaling; non-HER targeted TK inhibitors such as Imatinib mesylate (GLEEVAC™) available from Glaxo; MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo [2,3-d]pyrimidines; curcumin (diferuloyl methane, 4,5-bis(4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); Imatinib mesylate (Gleevac; Novartis); PKI 166 (Novartis); GW2016 (Glaxo SmithKline); CI-1033 (Pfizer); EKB-569 (Wyeth); Semaxinib (Sugen); ZD6474 (AstraZeneca); PTK-787 (Novartis/Schering AG); INC-1C11 (Imclone); cyanoguanidine quinazoline and cyanoamidine quinazolamine derivatives; or as described in any of the following patent publications: U.S. Pat. No. 5,804,396; WO99/09016 (American Cyanamid); WO98/43960 (American Cyanamid); WO97/38983 (Warner Lambert); WO99/06378 (Warner Lambert); WO99/06396

(Warner Lambert); WO96/30347 (Pfizer, Inc); WO96/33978 (Zeneca); WO96/3397 (Zeneca); WO96/33980 (Zeneca); and US2005/0101617.

An "anti-angiogenic agent" refers to a compound which blocks, or interferes with to some degree, the development of blood vessels. The anti-angiogenic factor may, for instance, be a small molecule or antibody that binds to a growth factor or growth factor receptor involved in promoting angiogenesis. The preferred anti-angiogenic factor herein is an antibody that binds to Vascular Endothelial Growth Factor (VEGF), such as Bevacizumab (AVASTIN®).

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-$\alpha$ and -$\beta$; mullerian-inhibiting substance; mouse gonadotropin-associated peptide; inhibin; activin; vascular endothelial growth factor; integrin; thrombopoietin (TPO); nerve growth factors such as NGF-$\beta$; platelet-growth factor; transforming growth factors (TGFs) such as TGF-$\alpha$ and TGF-$\beta$; insulin-like growth factor-I and -II; erythropoietin (EPO); osteoinductive factors; interferons such as interferon-$\alpha$, -$\beta$, and -$\gamma$; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1$\alpha$, IL-2, IL-3, IL-4, IL-5, IL-6, IL-7, IL-8, IL-9, IL-10, IL-11, IL-12; a tumor necrosis factor such as TNF-$\alpha$ or TNF-$\beta$; and other polypeptide factors including LIF and kit ligand (KL). As used herein, the term cytokine includes proteins from natural sources or from recombinant cell culture and biologically active equivalents of the native sequence cytokines.

II. HER2 Antibody Variant Compositions

The present invention concerns, at least in part, certain HER2 antibody compositions. Preferably, the HER2 antibody (either or both of the main species HER2 antibody and antibody variant thereof) is one which binds to Domain II of HER2, inhibits HER dimerization more effectively than Trastuzumab, and/or binds to a heterodimeric binding site of HER2. The preferred embodiment herein of the main species antibody is one comprising the variable light and variable heavy amino acid sequences in SEQ ID Nos. 3 and 4, and most preferably comprising the light chain and heavy chain amino acid sequences in SEQ ID Nos. 15 and 16 (Pertuzumab).

The composition herein comprises a mixture of the main species HER2 antibody and an amino acid sequence variant thereof comprising an amino-terminal leader extension. Preferably, the amino-terminal leader extension is on a light chain of the antibody variant (e.g. on one or two light chains of the antibody variant). The main species HER2 antibody or the antibody variant may be an intact antibody or antibody fragment (e.g. Fab of F(ab')2 fragments), but preferably both are intact antibodies.

The antibody variant herein comprises an amino-terminal leader extension on any one or more of the heavy or light chains thereof. Preferably, the amino-terminal leader extension is on one or two light chains of the antibody. The amino-terminal leader extension preferably comprises or consists of VHS-.

Presence of the amino-terminal leader extension in the composition can be detected by various analytical techniques including, but not limited to, N-terminal sequence analysis, assay for charge heterogeneity (for instance, cation exchange chromatography or capillary zone electrophoresis), mass spectrometry, etc. The amount of the antibody variant in the composition generally ranges from an amount that constitutes the lower detection limit of any assay (preferably cation exchange analysis) used to detect the variant to an amount less than the amount of the main species antibody. Generally, about 20% or less (e.g. from about 1% to about 15%, for instance from 5% to about 15%, and preferably from about 8% to about 12%) of the antibody molecules in the composition comprise an amino-terminal leader extension. Such percentage amounts are preferably determined using cation exchange analysis.

Aside from the amino-terminal leader extension variant, further amino acid sequence alterations of the main species antibody and/or variant are contemplated, including but not limited to an antibody comprising a C-terminal lysine residue on one or both heavy chains thereof (such an antibody variant may be present in an amount from about 1% to about 20%), a deamidated antibody variant (for instance, wherein Asn-386 and/or Asn-391 on one or two heavy chains of Pertuzumab are deamidated), antibody with one or more oxidized methionine residues (for example, Pertuzumab comprising oxidized met-254) etc.

Moreover, the main species antibody or variant may further comprise glycosylation variations, non-limiting examples of which include antibody comprising a G1 or G2 oligosaccharide structure attached to the Fc region thereof, antibody comprising a carbohydrate moiety attached to a light chain thereof (e.g. one or two carbohydrate moieties, such as glucose or galactose, attached to one or two light chains of the antibody, for instance attached to one or more lysine residues), antibody comprising one or two non-glycosylated heavy chains, or antibody comprising a sialidated oligosaccharide attached to one or two heavy chains thereof etc.

The invention also concerns a polypeptide comprising the amino acid sequence in SEQ ID No. 23 or a deamidated and/or oxidized variant thereof. In addition, the invention provides an antibody comprising one or two light chains, wherein either or both of the light chains comprise the amino acid sequence in SEQ ID No. 23. The antibody further comprises one or two heavy chains, wherein either or both of the heavy chains comprise the amino acid sequence in SEQ ID NO. 16 or SEQ ID NO. 24 (or deamidated and/or oxidized variants thereof).

The composition may be recovered from a genetically engineered cell line, e.g. a Chinese Hamster Ovary (CHO) cell line expressing the HER2 antibody, or may be prepared by peptide synthesis.

III. Production of HER2 Antibodies

A description follows as to exemplary techniques for the production of the antibodies used in accordance with the present invention. The HER2 antigen to be used for production of antibodies may be, e.g., a soluble form of the extracellular domain of HER2 or a portion thereof, containing the desired epitope. Alternatively, cells expressing HER2 at their cell surface (e.g. NIH-3T3 cells transformed to overexpress HER2; or a carcinoma cell line such as SK-BR-3 cells, see Stancovski et al. *PNAS (USA)* 88:8691-8695 (1991)) can be used to generate antibodies. Other forms of HER$^2$ useful for generating antibodies will be apparent to those skilled in the art.

(i) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ¹⁄₁₀ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Monoclonal antibodies are obtained from a population of substantially homogeneous antibodies, i.e., the individual antibodies comprising the population are identical and/or bind the same epitope, except for possible variants that may arise during production of the monoclonal antibody, such as those variants described herein. Thus, the modifier "monoclonal" indicates the character of the antibody as not being a mixture of discrete antibodies.

For example, the monoclonal antibodies may be made using the hybridoma method first described by Kohler et al., Nature, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133; 3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., Anal. Biochem., 107:220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Plückthun, Immunol. Revs., 130: 151-188 (1992).

In a further embodiment, monoclonal antibodies or antibody fragments can be isolated from antibody phage libraries generated using the techniques described in McCafferty et al., Nature, 348:552-554 (1990). Clackson et al., Nature, 352: 624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy chain and light chain constant domains in place of the homologous murine sequences (U.S. Pat. No. 4,816,567; and Morrison, et al., *Proc. Natl Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Humanized Antibodies

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences., The human sequence which is closest to that of the rodent is then accepted as the human framework region (FR) for the humanized antibody (Sims et al., *J. Immunol.*, 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

WO01/00245 describes production of exemplary humanized HER2 antibodies which bind HER2 and block ligand activation of a HER receptor. The humanized antibody of particular interest herein blocks EGF, TGF-α and/or HRG mediated activation of MAPK essentially as effectively as intact murine monoclonal antibody 2C4 (or a Fab fragment thereof) and/or binds HER2 essentially as effectively as intact murine monoclonal antibody 2C4 (or a Fab fragment thereof). The humanized antibody herein may, for example, comprise nonhuman hypervariable region residues incorporated into a human variable heavy domain and may further comprise a framework region (FR) substitution at a position selected from the group consisting of 69H, 71H and 73H utilizing the variable domain numbering system set forth in Kabat et al., *Sequences of Proteins of Immunological Interest*, 5th Ed. Public Health Service, National Institutes of Health, Bethesda, Md. (1991). In one embodiment, the humanized antibody comprises FR substitutions at two or all of positions 69H, 71H and 73H.

An exemplary humanized antibody of interest herein comprises variable heavy complementarity determining residues GFTFTDYTMX, where X is preferably D or S (SEQ ID NO:7); DVNPNSGGSIYNQRFKG (SEQ ID NO:8); and/or NLGPSFYFDY (SEQ ID NO:9), optionally comprising amino acid modifications of those CDR residues, e.g. where the modifications essentially maintain or improve affinity of the antibody. For example, the antibody variant of interest may have from about one to about seven or about five amino acid substitutions in the above variable heavy CDR sequences. Such antibody variants may be prepared by affinity maturation, e.g., as described below. The most preferred humanized antibody comprises the variable heavy amino acid sequence in SEQ ID NO:4.

The humanized antibody may comprise variable light complementarity determining residues KASQDVSIGVA (SEQ ID NO:10); SASYX$^1$X$^2$X$^3$, where X$^1$ is preferably R or L, X$^2$ is preferably Y or E, and X$^3$ is preferably T or S (SEQ ID NO:11); and/or QQYYIYPYT (SEQ ID NO:12), e.g. in addition to those variable heavy domain CDR residues in the preceding paragraph. Such humanized antibodies optionally comprise amino acid modifications of the above CDR residues, e.g. where the modifications essentially maintain or improve affinity of the antibody. For example, the antibody variant of interest may have from about one to about seven or about five amino acid substitutions in the above variable light CDR sequences. Such antibody variants may be prepared by affinity maturation, e.g., as described below. The most preferred humanized antibody comprises the variable light amino acid sequence in SEQ ID NO:3.

The present application also contemplates affinity matured antibodies which bind HER2 and block ligand activation of a HER receptor. The parent antibody may be a human antibody or a humanized antibody, e.g., one comprising the variable light and/or variable heavy sequences of SEQ ID Nos. 3 and 4, respectively (i.e. variant 574). The affinity matured antibody preferably binds to HER2 receptor with an affinity superior to that of intact murine 2C4 or intact variant 574 (e.g. from about two or about four fold, to about 100 fold or about 1000 fold improved affinity, e.g. as assessed using a HER2-extracellular domain (ECD) ELISA). Exemplary variable heavy CDR residues for substitution include H28, H30, H34, H35, H64, H96, H99, or combinations of two or more (e.g. two, three, four, five, six, or seven of these residues).

Examples of variable light CDR residues for alteration include L28, L50, L53, L56, L91, L92, L93, L94, L96, L97 or combinations of two or more (e.g. two to three, four, five or up to about ten of these residues).

Various forms of the humanized antibody or affinity matured antibody are contemplated. For example, the humanized antibody or affinity matured antibody may be an antibody fragment, such as a Fab, which is optionally conjugated with one or more cytotoxic agent(s) in order to generate an immunoconjugate. Alternatively, the humanized antibody or affinity matured antibody may be an intact antibody, such as an intact IgG1 antibody.

(iv) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); and U.S. Pat. Nos. 5,591,669, 5,589,369 and 5,545,807.

Alternatively, phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson, Kevin S, and Chiswell, David J., *Current Opinion in Structural Biology* 3:564-571 (1993). Several sources of V-gene segments can be used for phage display. Clackson et al., *Nature*, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

Human antibodies may also be generated by in vitro activated B cells (see U.S. Pat. Nos. 5,567,610 and 5,229,275).

Human HER2 antibodies are described in U.S. Pat. No. 5,772,997 issued Jun. 30, 1998 and WO 97/00271 published Jan. 3, 1997.

(v) Antibody Fragments

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science*, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. The antibody fragment may also be a "linear antibody", e.g., as described in U.S. Pat. No. 5,641,870 for example. Such linear antibody fragments may be monospecific or bispecific.

(vi) Bispecific Antibodies

Bispecific antibodies are antibodies that have binding specificities for at least two different epitopes. Exemplary bispecific antibodies may bind to two different epitopes of the HER2 protein. Other such antibodies may combine a HER2 binding site with binding site(s) for EGFR, HER3 and/or HER4. Alternatively, a HER2 arm may be combined with an arm which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the HER2-expressing cell. Bispecific antibodies may also be used to localize cytotoxic agents to cells which express HER2. These antibodies possess a HER2-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab')$_2$ bispecific antibodies).

WO 96/16673 describes a bispecific HER2/FcγRIII antibody and U.S. Pat. No. 5,837,234 discloses a bispecific HER2/FcγRI antibody IDM1 (Osidem). A bispecific HER2/Fcα antibody is shown in WO98/02463. U.S. Pat. No. 5,821,337 teaches a bispecific HER2/CD3 antibody. MDX-210 is a bispecific HER2-FcγRIII Ab.

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')₂ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')₂ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

(vii) Other Amino Acid Sequence Modifications

Amino acid sequence modification(s) of the HER2 antibodies described herein are contemplated. For example, it may be desirable to improve the binding affinity and/or other biological properties of the antibody. Amino acid sequence variants of the HER2 antibody are prepared by introducing appropriate nucleotide changes into the HER2 antibody nucleic acid, or by peptide synthesis. Such modifications include, for example, deletions from, and/or insertions into and/or substitutions of, residues within the amino acid sequences of the HER2 antibody. Any combination of deletion, insertion, and substitution is made to arrive at the final construct, provided that the final construct possesses the desired characteristics. The amino acid changes also may alter post-translational processes of the HER2 antibody, such as changing the number or position of glycosylation sites.

A useful method for identification of certain residues or regions of the HER2 antibody that are preferred locations for mutagenesis is called "alanine scanning mutagenesis" as described by Cunningham and Wells *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with HER2 antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed HER2 antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include a HER2 antibody with an N-terminal methionyl residue or the antibody fused to a cytotoxic polypeptide. Other insertional variants of the HER2 antibody molecule include the fusion to the N- or C-terminus of the HER2 antibody to an enzyme (e.g. for ADEPT) or a polypeptide which increases the serum half-life of the antibody.

Another type of variant is an amino acid substitution variant. These variants have at least one amino acid residue in the HER2 antibody molecule replaced by a different residue. The sites of greatest interest for substitutional mutagenesis include the hypervariable regions or CDRs, but FR or Fc region alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their, effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in *Biochemistry, second ed., pp. 73-75*, Worth Publishers, New York (1975)):

(1) non-polar: Ala (A), Val (V), Leu (L), Ile (I), Pro (P), Phe (F), Trp (W), Met (M)

(2) uncharged polar: Gly (G), Ser (S), Thr (T), Cys (C), Tyr (Y), Asn (N), Gln (O)

(3) acidic: Asp (D), Glu (E)

(4) basic: Lys (K), Arg (R), His (H)

Alternatively, naturally occurring residues may be divided into groups based on common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: H is, Lys, Arg;

(5) residues that influence chain orientation: Gly, Pro;

(6) aromatic: Trp, Tyr, Phe.

Non-conservative substitutions will entail exchanging a member of one of these classes for another class.

Any cysteine residue not involved in maintaining the proper conformation of the HER2 antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and huma HER2. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, any oligosaccharide structure attached thereto may be altered. For example, antibodies with a mature carbohydrate structure that lacks fucose attached to an Fc region of the antibody are described in US Pat Appl No US 2003/0157108 A1, Presta, L. See also US 2004/0093621 A1 (Kyowa Hakko Kogyo Co., Ltd). Antibodies with a bisecting N-acetylglucosamine (GlcNAc) in the oligosaccharide structure attached to an Fc region of the antibody are referenced in WO03/011878, Jean-Mairet et al. and U.S. Pat. No. 6,602,684, Umana et al. Antibodies with at least one galactose residue in an oligosaccharide structure attached to an Fc region of the antibody are reported in WO97/30087, Patel et al. See, also, WO98/58964 (Raju, S.) and WO99/22764 (Raju, S.) concerning antibodies with altered carbohydrate attached to the Fc region thereof. Antibody compositions comprising main species antibody with such carbohydrate structures attached to one or two heavy chains of the Fc region are contemplated herein.

Nucleic acid molecules encoding amino acid sequence variants of the HER2 antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the HER2 antibody.

(viii) Screening for Antibodies with the Desired Properties

Techniques for generating antibodies have been described above. One may further select antibodies with certain biological characteristics, as desired.

To identify an antibody which blocks ligand activation of a HER receptor, the ability of the antibody to block HER ligand binding to cells expressing the HER receptor (e.g. in conjugation with another HER receptor with which the HER receptor of interest forms a HER hetero-oligomer) may be determined. For example, cells naturally expressing, or transfected to express, HER receptors of the HER hetero-oligomer may be incubated with the antibody and then exposed to labeled HER ligand. The ability of the HER2 antibody to block ligand binding to the HER receptor in the HER hetero-oligomer may then be evaluated.

For example, inhibition of HRG binding to MCF7 breast tumor cell lines by HER2 antibodies may be performed using monolayer MCF7 cultures on ice in a 24-well-plate format essentially as described in WO01/00245. HER2 monoclonal antibodies may be added to each well and incubated for 30 minutes. $^{125}$I-labeled rHRGβ1$_{177-224}$ (25 pm) may then be added, and the incubation may be continued for 4 to 16 hours. Dose response curves may be prepared and an IC$_{50}$ value may be calculated for the antibody of interest. In one embodiment, the antibody which blocks ligand activation of an HER receptor will have an IC$_{50}$ for inhibiting HRG binding to MCF7 cells in this assay of about 50 nM or less, more preferably 10 nM or less. Where the antibody is an antibody fragment such as a Fab fragment, the IC$_{50}$ for inhibiting HRG binding to MCF7 cells in this assay may, for example, be about 100 nM or less, more preferably 50 nM or less.

Alternatively, or additionally, the ability of the HER2 antibody to block HER ligand-stimulated tyrosine phosphorylation of a HER receptor present in a HER hetero-oligomer may be assessed. For example, cells endogenously expressing the HER receptors or transfected to expressed them may be incubated with the antibody and then assayed for HER ligand-dependent tyrosine phosphorylation activity using an anti-phosphotyrosine monoclonal (which is optionally conjugated with a detectable label). The kinase receptor activation assay described in U.S. Pat. No. 5,766,863 is also available for determining HER receptor activation and blocking of that activity by an antibody.

In one embodiment, one may screen for an antibody which inhibits HRG stimulation of p180 tyrosine phosphorylation in MCF7 cells essentially as described in WO01/00245. For example, the MCF7 cells may be plated in 24-well plates and monoclonal antibodies to HER2 may be added to each well and incubated for 30 minutes at room temperature; then rHRGβ1$_{177-244}$ may be added to each well to a final concentration of 0.2 nM, and the incubation may be continued for 8 minutes. Media may be aspirated from each well, and reactions may be stopped by the addition of 100 µl of SDS sample buffer (5% SDS, 25 mM DTT, and 25 mM Tris-HCl, pH 6.8). Each sample (25 µl) may be electrophoresed on a 4-12% gradient gel (Novex) and then electrophoretically transferred to polyvinylidene difluoride membrane. Antiphosphotyrosine (at 1 µg/ml) immunoblots may be developed, and the intensity of the predominant reactive band at M$_r$~180,000 may be quantified by reflectance densitometry. The antibody selected will preferably significantly inhibit HRG stimulation of p180 tyrosine phosphorylation to about 0-35% of control in this assay. A dose-response curve for inhibition of HRG stimulation of p180 tyrosine phosphorylation as determined by reflectance densitometry may be prepared and an IC$_{50}$ for the antibody of interest may be calculated. In one embodiment, the antibody which blocks ligand activation of a HER receptor will have an IC, for inhibiting HRG stimulation of p180 tyrosine phosphorylation in this assay of about 50 nM or less, more preferably 10 nM or less. Where the antibody is an antibody fragment such as a Fab fragment, the IC$_{50}$ for inhibiting HRG stimulation of p180 tyrosine phosphorylation in this assay may, for example, be about 100 nM or less, more preferably 50 nM or less.

One may also assess the growth inhibitory effects of the antibody on MDA-MB-175 cells, e.g, essentially as described in Schaefer et al. *Oncogene* 15:1385-1394 (1997). According to this assay, MDA-MB-175 cells may treated with a HER2 monoclonal antibody (10 µg/mL) for 4 days and stained with crystal violet. Incubation with a HER2 antibody may show a growth inhibitory effect on this cell line similar to that displayed by monoclonal antibody 2C4. In a further embodiment, exogenous HRG will not significantly reverse this inhibition. Preferably, the antibody will be able to inhibit cell proliferation of MDA-MB-175 cells to a greater extent than monoclonal antibody 4D5 (and optionally to a greater extent than monoclonal antibody 7F3), both in the presence and absence of exogenous HRG.

In one embodiment, the HER2 antibody of interest may block heregulin dependent association of HER2 with HER3 in both MCF7 and SK-BR-3 cells as determined in a co-immunoprecipitation experiment such as that described in WO01/00245 substantially more effectively than monoclonal antibody 4D5, and preferably substantially more effectively than monoclonal antibody 7F3.

To identify growth inhibitory HER2 antibodies, one may screen for antibodies which inhibit the growth of cancer cells which overexpress HER2. In one embodiment, the growth inhibitory antibody of choice is able to inhibit growth of SK-BR-3 cells in cell culture by about 20-100% and preferably by about 50-100% at an antibody concentration of about 0.5 to 30 µg/ml. To identify such antibodies, the SK-BR-3 assay described in U.S. Pat. No. 5,677,171 can be performed. According to this assay, SK-BR-3 cells are grown in a 1:1 mixture of F12 and DMEM medium supplemented with 10% fetal bovine serum, glutamine and penicillin streptomycin. The SK-BR-3 cells are plated at 20,000 cells in a 35 mm cell culture dish (2 m-1s/35 mm dish). 0.5 to 30 µg/ml of the HER2 antibody is added per dish. After six days, the number of cells, compared to untreated cells are counted using an electronic COULTER™ cell counter. Those antibodies which inhibit growth of the SK-BR-3 cells by about 20-100% or about 50-100% may be selected as growth inhibitory antibodies. See U.S. Pat. No. 5,677,171 for assays for screening for growth inhibitory antibodies, such as 4D5 and 3E8.

In order to select for antibodies which induce apoptosis, an annexin binding assay using BT474 cells is available. The BT474 cells are cultured and seeded in dishes as discussed in the preceding paragraph. The medium is then removed and replaced with fresh medium alone or medium containing 10 µg/ml of the monoclonal antibody. Following a three day incubation period, monolayers are washed with PBS and detached by trypsinization. Cells are then centrifuged, resuspended in $Ca^{2+}$ binding buffer and aliquoted into tubes as discussed above for the cell death assay. Tubes then receive labeled annexin (e.g. annexin V-FTIC) (1 µg/ml). Samples may be analyzed using a FACSCAN™ flow cytometer and FACSCONVERT™ CellQuest software (Becton Dickinson). Those antibodies which induce statistically significant levels of annexin binding relative to control are selected as apoptosis-inducing antibodies. In addition to the annexin binding assay, a DNA staining assay using BT474 cells is available. In order to perform this assay, BT474 cells which have been treated with the antibody of interest as described in the preceding two paragraphs are incubated with 9 µg/ml HOECHST 33342™ for 2 hr at 37° C., then analyzed on an EPICS ELITE™ flow cytometer (Coulter Corporation) using MODFIT LT™ software (Verity Software House). Antibodies which induce a change in the percentage of apoptotic cells which is 2 fold or greater (and preferably 3 fold or greater) than untreated cells (up to 100% apoptotic cells) may be selected as pro-apoptotic antibodies using this assay. See WO98/17797 for assays for screening for antibodies which induce apoptosis, such as 7C2 and 7F3.

To screen for antibodies which bind to an epitope on HER2 bound by an antibody of interest, a routine cross-blocking assay such as that described in *Antibodies, A Laboratory Manual*, Cold Spring Harbor Laboratory, Ed Harlow and David Lane (1988), can be performed to assess whether the antibody cross-blocks binding of an antibody, such as 2C4 or Pertuzumab, to HER2. Alternatively, or additionally, epitope mapping can be performed by methods known in the art and/or one can study the antibody-HER2 structure (Franklin et al. *Cancer Cell* 5:317-328 (2004)) to see what domain(s) of HER2 is/are bound by the antibody.

(ix) Immunoconjugates

The invention also pertains to immunoconjugates comprising an antibody conjugated to a cytotoxic agent such as a chemotherapeutic agent, toxin (e.g. a small molecule toxin or an enzymatically active toxin of bacterial, fungal, plant or animal origin, including fragments and/or variants thereof), or a radioactive isotope (i.e., a radioconjugate).

Chemotherapeutic agents useful in the generation of such immunoconjugates have been described above. Conjugates of an antibody and one or more small molecule toxins, such as a calicheamicin, a maytansine (U.S. Pat. No. 5,208,020), a trichothene, and CC1065 are also contemplated herein.

In one preferred embodiment of the invention, the antibody is conjugated to one or more maytansine molecules (e.g. about 1 to about 10 maytansine molecules per antibody molecule). Maytansine may, for example, be converted to May-SS-Me which may be reduced to May-SH3 and reacted with modified antibody (Chari et al. *Cancer Research* 52: 127-131 (1992)) to generate a maytansinoid-antibody immunoconjugate.

Another immunoconjugate of interest comprises a HER2 antibody conjugated to one or more calicheamicin molecules. The calicheamicin family of antibiotics are capable of producing double-stranded DNA breaks at sub-picomolar concentrations. Structural analogues of calicheamicin which may be used include, but are not limited to, $\gamma_1 I$, $\alpha_2^I$, $\alpha_3^I$, N-acetyl-$\gamma_1^I$, PSAG and $\theta^I_1$ (Hinman et al. *Cancer Research* 53: 3336-3342 (1993) and Lode et al. *Cancer Research* 58: 2925-2928 (1998)). See, also, U.S. Pat. Nos. 5,714,586; 5,712,374; 5,264,586; and 5,773,001 expressly incorporated herein by reference.

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g. a ribonuclease or a DNA endonuclease such as a deoxyribonuclease; DNase).

A variety of radioactive isotopes are available for the production of radioconjugated HER2 antibodies. Examples include $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu.

Conjugates of the antibody and cytotoxic agent may be made using a variety of bifunctional protein coupling agents such as N-succinimidyl-3-(2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as his (p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, dimethyl linker or disulfide-containing linker (Chari et al. *Cancer Research* 52: 127-131 (1992)) may be used.

Alternatively, a fusion protein comprising the HER2 antibody and cytotoxic agent may be made, e.g. by recombinant techniques or peptide synthesis.

In yet another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

(x) Other Antibody Modifications

Other modifications of the antibody are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example; liposomes, albumin microspheres, microemulsions, nano-particles and nanocapsules), or in macroemulsions. Such techniques are disclosed in *Remington's Pharmaceutical Sciences*, 16th edition, Oslo, A., Ed., (1980).

It may be desirable to modify the antibody of the invention with respect to effector function, e.g. so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989).

WO00/42072 (Presta, L.) describes antibodies with improved ADCC function in the presence of human effector cells, where the antibodies comprise amino acid substitutions in the Fc region thereof. Preferably, the antibody with improved ADCC comprises substitutions at positions 298, 333, and/or 334 of the Fc region. Preferably the altered Fc region is a human IgG1 Fc region comprising or consisting of substitutions at one, two or three of these positions.

Antibodies with altered C1q binding and/or complement dependent cytotoxicity (CDC) are described in WO99/51642, U.S. Pat. No. 6,194,551B1, U.S. Pat. No. 6,242,195B1, U.S. Pat. No. 6,528,624B1 and U.S. Pat. No. 6,538,124 (Idusogie et al.). The antibodies comprise an amino acid substitution at one or more of amino acid positions 270, 322, 326, 327, 329, 313, 333 and/or 334 of the Fc region thereof.

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule. Antibodies with substitutions in an Fc region thereof and increased serum half-lives are also described in WO00/42072 (Presta, L.).

Engineered antibodies with three or more (preferably four) functional antigen binding sites are also contemplated (US Appln No. US2002/0004587 A1, Miller et at).

The HER2 antibodies disclosed herein may also be formulated as immunoliposomes. Liposomes containing the antibody are prepared by methods known in the art, such as described in Epstein et al., *Proc. Natl. Acad. Sci. USA*, 82:3688 (1985); Hwang et al., *Proc. Natl. Acad. Sci. USA*, 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. *J. Biol. Chem.* 257:286-288 (1982) via a disulfide interchange reaction. A chemotherapeutic agent is optionally contained within the liposome. See Gabizon et al. *J. National Cancer Inst.* 81(19)1484 (1989).

IV. Pharmaceutical Formulations

Therapeutic formulations of the compositions of the present invention are prepared for storage by mixing the composition with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Lyophilized HER2 antibody formulations are described in WO 97/04801.

The formulation herein may also contain more than one active compound as necessary for the particular indication being treated, preferably those with complementary activities that do not adversely affect each other. For example, it may be desirable to further provide antibodies which bind to EGFR, HER2 (e.g. an antibody which binds a different epitope on HER2), HER3, HER4, or vascular endothelial factor (VEGF) in the one formulation. Alternatively, or additionally, the composition may further comprise a chemotherapeutic agent, cytotoxic agent, cytokine, growth inhibitory agent, anti-hormonal agent, EGFR-targeted drug, anti-angiogenic agent, tyrosine kinase inhibitor, and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

V. Screening Patients for Therapy

According to a preferred embodiment of the invention herein, the patient selected for therapy has a tumor, or other cell or tissue, displaying HER (and preferably HER2) activation. In one embodiment, the extent of HER (or HER2) activation in cancer cells or other cells tested significantly exceeds the level of activation of that receptor in non-cancerous or normal cells of the same tissue type. Such excessive activation may result from overexpression of the HER receptor and/or greater than normal levels of a HER ligand available for activating the HER receptor in the cancer cells. Such excessive activation may cause and/or be caused by the malignant state of a cancer cell. In some embodiments, the cancer will be subjected to a diagnostic or prognostic assay to determine whether amplification and/or overexpression of a HER receptor is occurring which results in such excessive activation of the HER receptor. Alternatively, or additionally, the cancer may be subjected to a diagnostic or prognostic assay to determine whether amplification and/or overexpression a HER ligand is occurring in the cancer which contributes to excessive activation of the receptor. In a subset of such cancers, excessive activation of the receptor may result from an autocrine stimulatory pathway. Various exemplary assays for determining HER activation will be described in more detail below.

(i) HER Dimers

Samples can be assessed for the presence of HER dimers, as indicating HER or HER2 activation. Any method known in the art may be used to detect HER2 dimers, such as EGFR-HER2, HER2-HER3. Several preferred methods are described below. These methods detect noncovalent protein-protein interactions or otherwise indicate proximity between proteins of interest.

Immunoaffinity-based methods, such as immunoprecipitation or ELISA, may be used to detect HER dimers. In one embodiment, HER2 antibodies are used to immunoprecipitate complexes comprising HER2 from tumor cells, and the resulting immunoprecipitant is then probed for the presence of EGFR or HER3 by immunoblotting. In another embodiment, EGFR or HER3 antibodies may be used for the immunoprecipitation step and the immunoprecipitant then probed with HER2 antibodies. In a further embodiment, HER ligands specific to EGFR, HER3, EGFR-HER2 complexes or HER2-HER3 complexes may be used to precipitate complexes, which are then probed for the presence of HER2. For example, ligands may be conjugated to avidin and complexes purified on a biotin column.

In other embodiments, such as ELISA or antibody "sandwich"-type assays, antibodies to HER2 are immobilized on a solid support, contacted with tumor cells or tumor cell lysate, washed, and then exposed to antibody against EGFR or HER3. Binding of the latter antibody, which may be detected directly or by a secondary antibody conjugated to a detectable label, indicates the presence of heterodimers. In certain embodiments, EGFR or HER3 antibody is immobilized, and HER2 antibody is used for the detection step. In other embodiments HER ligands may be used in place of, or in combination with HER antibodies.

Chemical or UV cross-linking may also be used to covalently join dimers on the surface of living cells. Hunter et al., *Biochem. J.,* 320:847-53. Examples of chemical cross-linkers include dithiobis(succinimidyl) propionate (DSP) and 3,3' dithiobis(sulphosuccinimidyl) propionate (DTSSP). In one embodiment, cell extracts from chemically cross-linked tumor cells are analyzed by SDS-PAGE and immunoblotted with antibodies to EGFR and/or HER3. A supershifted band of the appropriate molecular weight most likely represents EGFR-HER2 or HER2-HER3 dimers, as HER2 is the preferred dimerization partner for EGFR and HER3. This result may be confirmed by subsequent immunoblotting with HER2 antibodies.

Fluorescence resonance energy transfer (FRET) may also be used to detect EGFR-HER2 or HER2-HER3 dimers. FRET detects protein conformational changes and protein-protein interactions in vivo and in vitro based on the transfer of energy from a donor fluorophore to an acceptor fluorophore. Selvin, *Nat. Struct. Biol.,* 7:730-34 (2000). Energy transfer takes place only if the donor fluorophore is in sufficient proximity to the acceptor fluorophore. In a typical FRET experiment, two proteins or two sites on a single protein are labeled with different fluorescent probes. One of the probes, the donor probe, is excited to a higher energy state by incident light of a specified wavelength. The donor probe then transmits its energy to the second probe, the acceptor probe, resulting in a reduction in the donor's fluorescence intensity and an increase in the acceptor's fluorescence emission. To measure the extent of energy transfer, the donor's intensity in a sample labeled with donor and acceptor probes is compared with its intensity in a sample labeled with donor probe only. Optionally, acceptor intensity is compared in donor/acceptor and acceptor only samples. Suitable probes are known in the art and include, for example, membrane permeant dyes, such as fluorescein and rhodamine, organic dyes, such as the cyanine dyes, and lanthanide atoms. Selvin, supra. Methods and instrumentation for detecting and measuring energy transfer are also known in the art. Selvin, supra.

FRET-based techniques suitable for detecting and measuring protein-protein interactions in individual cells are also known in the art. For example, donor photobleaching fluorescence resonance energy transfer (pbFRET) microscopy and fluorescence lifetime imaging microscopy (FLIM) may be used to detect the dimerization of cell surface receptors. Selvin, supra; Gadella & Jovin, *J. Cell Biol.,* 129:1543-58 (1995). In one embodiment, pbFRET is used on cells either "in suspension" or "in situ" to detect and measure the formation of EGFR-HER2 or HER2-HER3 dimers, as described in Nagy et al., *Cytometry,* 32:120-131 (1998). These techniques measure the reduction in a donor's fluorescence lifetime due to energy transfer. In a particular embodiment, a flow cytometric Foerster-type FRET technique (FCET) may be used to investigate EGFR-HER2 and HER2-HER3 dimerization, as described in Nagy et al., supra, and Brockhoff et al., *Cytometry*, 44:338-48 (2001).

FRET is preferably used in conjunction with standard immunohistochemical labeling techniques. Kenworthy, *Methods*, 24:289-96 (2001). For example, antibodies conjugated to suitable fluorescent dyes can be used as probes for labeling two different proteins. If the proteins are within proximity of one another, the fluorescent dyes act as donors and acceptors for FRET. Energy transfer is detected by standard means. Energy transfer may be detected by flow cytometric means or by digital microscopy systems, such as confocal microscopy or wide-field fluorescence microscopy coupled to a charge-coupled device (CCD) camera.

In one embodiment of the present invention, HER2 antibodies and either EGFR or HER3 antibodies are directly labeled with two different fluorophores, for example as described in Nagy et al, supra. Tumor cells or tumor cell lysates are contacted with the differentially labeled antibodies, which act as donors and acceptors for FRET in the presence of EGFR-HER2 or HER2-HER3 dimers. Alternatively, unlabeled antibodies against HER2 and either EGFR or HER3 are used along with differentially labeled secondary antibodies that serve as donors and acceptors. See, for example, Brockhoff et al., supra. Energy transfer is detected and the presence of dimers is determined if the labels are found to be in close proximity.

In other embodiments HER receptor ligands that are specific for HER2 and either EGFR or HER3 are fluorescently labeled and used for FRET studies.

In still other embodiments of the present invention, the presence of dimers on the surface of tumor cells is demonstrated by co-localization of HER2 with either EGFR or HER3 using standard direct or indirect immunofluorescence techniques and confocal laser scanning microscopy. Alternatively, laser scanning imaging (LSI) is used to detect antibody binding and co-localization of HER2 with either EGFR or HER3 in a high-throughput format, such as a microwell plate, as described in Zuck et al, *Proc. Natl. Acad. Sci. USA*, 96:11122-27 (1999).

In further embodiments, the presence of EGFR-HER2 and/or HER2-HER3 dimers is determined by identifying enzymatic activity that is dependent upon the proximity of the dimer components. A HER2 antibody is conjugated with one enzyme and an EGFR or HER3 antibody is conjugated with a second enzyme. A first substrate for the first enzyme is added and the reaction produces a second substrate for the second enzyme. This leads to a reaction with another molecule to produce a detectable compound, such as a dye. The presence of another chemical breaks down the second substrate, so that reaction with the second enzyme is prevented unless the first and second enzymes, and thus the two antibodies, are in close proximity. In a particular embodiment tumor cells or cell lysates are contacted with a HER2 antibody that is conjugated with glucose oxidase and a HER3 or HER1 antibody that is conjugated with horse radish peroxidase. Glucose is added to the reaction, along with a dye precursor, such as DAB, and catalase. The presence of dimers is determined by the development of color upon staining for DAB.

Dimers may also be detected using methods based on the eTag™ assay system (Aclara Bio Sciences, Mountain View, Calif.), as described, for example, in U.S. Patent Application 2001/0049105, published Dec. 6, 2001, both of which are expressly incorporated by reference in their entirety. An eTag™, or "electrophoretic tag," comprises a detectable reporter moiety, such as a fluorescent group. It may also comprise a "mobility modifier," which consists essentially of a moiety having a unique electrophoretic mobility. These moieties allow for separation and detection of the eTag™ from a complex mixture under defined electrophoretic conditions, such as capillary electrophoresis (CE). The portion of the eTag™ containing the reporter moiety and, optionally, the mobility modifier is linked to a first target binding moiety by a cleavable linking group to produce a first binding compound. The first target binding moiety specifically recognizes a particular first target, such as a nucleic acid or protein. The first target binding moiety is not limited in any way, and may be for example, a polynucleotide or a polypeptide. Preferably, the first target binding moiety is an antibody or antibody fragment. Alternatively, the first target binding moiety may be a HER receptor ligand or binding-competent fragment thereof.

The linking group preferably comprises a cleavable moiety, such as an enzyme substrate, or any chemical bond that may be cleaved under defined conditions. When the first target binding moiety binds to its target, the cleaving agent is introduced and/or activated, and the linking group is cleaved, thus releasing the portion of the eTag™ containing the reporter moiety and mobility modifier. Thus, the presence of a "free" eTag™ indicates the binding of the target binding moiety to its target.

Preferably, a second binding compound comprises the cleaving agent and a second target binding moiety that specifically recognizes a second target. The second target binding moiety is also not limited in any way and may be, for example, an antibody or antibody fragment or a HER receptor ligand or binding competent ligand fragment. The cleaving agent is such that it will only cleave the linking group in the first binding compound If the first binding compound and the second binding compound are in close proximity.

In an embodiment of the present invention, a first binding compound comprises an eTag™ in which an antibody to HER2 serves as the first target binding moiety. A second binding compound comprises an antibody to EGFR or HER3 joined to a cleaving agent capable of cleaving the linking group of the eTag™. Preferably the cleaving agent must be activated in order to be able to cleave the linking group. Tumor cells or tumor cell lysates are contacted with the eTag™, which binds to HER2, and with the modified EGFR or HER3 antibody, which binds to EGFR or HER3 on the cell surface. Unbound binding compound is preferable removed, and the cleaving agent is activated, if necessary. If EGFR-HER2 or HER2-HER3 dimers are present, the cleaving agent will cleave the linking group and release the eTag™ due to the proximity of the cleaving agent to the linking group. Free eTag™ may then be detected by any method known in the art, such as capillary electrophoresis.

In one embodiment, the cleaving agent is an activatable chemical species that acts on the linking group. For example, the cleaving agent may be activated by exposing the sample to light.

In another embodiment, the eTag™ is constructed using an antibody to EGFR or HER3 as the first target binding moiety, and the second binding compound is constructed from an antibody to HER2.

In yet another embodiment, the HER dimer is detected using an antibody or other reagent which specifically or preferentially binds to the dimer as compared to binding thereof to either HER receptor in the dimer.

(ii) HER2 Phosphorylation

Immunoprecipitation with EGFR, HER2, or HER3 antibody as discussed in the previous section may optionally be followed by a functional assay for dimers, as an alternative or supplement to immunoblotting. In one embodiment, immunoprecipitation with HER3 antibody is followed by an assay for receptor tyrosine kinase activity in the immunoprecipitant. Because HER3 does not have intrinsic tyrosine kinase activity, the presence of tyrosine kinase activity in the immunoprecipitant indicates that HER3 is most likely associated with HER2. Graus-Porta et al., *EMBO J.,* 16:1647-55 (1997); Klapper et al., *Proc. Natl. Acad. Sci. USA,* 96:4995-5000 (1999). This result may be confirmed by immunoblotting with HER2 antibodies. In another embodiment, immunoprecipitation with HER2 antibody is followed by an assay for EGFR receptor tyrosine kinase activity. In this assay, the immunoprecipitant is contacted with radioactive ATP and a peptide substrate that mimics the in vivo site of transphosphorylation of HER2 by EGFR. Phosphorylation of the peptide indicates co-immunoprecipitation and thus dimerization of EGFR with HER2. Receptor tyrosine kinase activity assays are well known in the art and include assays that detect phosphorylation of target substrates, for example, by phosphotyrosine antibody, and activation of cognate signal transduction pathways, such as the MAPK pathway.

Phosphorylation of HER receptor may be assessed by immunoprecipitation of one or more HER receptors, such as HER2 (HER2) receptor, and Western blot analysis. For example, positivity is determined by the presence of a phospho-HER2 band on the gel, using an anti-phosphotyrosine antibody to detect phosphorylated tyrosine residue(s) in the immunoprecipitated HER receptor(s). Anti-phosphotyrosine antibodies are commercially available from PanVera (Madison, Wis.), a subsidiary of Invitrogen, Chemicon International Inc. (Temecula, Calif.), or Upstate Biotechnology (Lake Placid, N.Y.). Negativity is determined by the absence of the band.

In another embodiment, phosphorylation of HER2 (HER2) receptor is assessed by immunohistochemistry using a phospho-specific HER2 antibody (clone PN2A; Thor et al., *J. Clin. Oncol.,* 18(18):3230-3239 (2000)).

Other methods for detecting phosphorylation of HER receptor(s) include, but are not limited to, KIRA ELISA (U.S. Pat. Nos. 5,766,863; 5,891,650; 5,914,237; 6,025,145; and 6,287,784), mass spectrometry (comparing size of phosphorylated and non-phosphorylated HER2), and e-tag proximity assay with both a HER (e.g. HER2) antibody and phospho-specific or phospho-tyrosine specific antibody (e.g., using the eTag™ assay kit available from Aclara BioSciences (Mountain View, Calif.). Details of the eTag assay are described hereinabove.

One may also use phospho-specific antibodies in cellular array to detect phosphorylation status in a cellular sample of signal transduction protein (US 2003/0190689).

(iii) HER2 Ligands

Levels of a HER ligand, such as TGF-α, in or associated with the tumor may be determined according to known procedures. Such assays may detect protein and/or nucleic acid encoding it in the sample to be tested. In one embodiment, HER ligand levels in the tumor may be determined using immunohistochemistry (1HC); see, for example, Scher et al. *Clin. Cancer Research* 1:545-550 (1995). Alternatively, or additionally, one may evaluate levels of HER ligand-encoding nucleic acid in the sample to be tested; e.g. via FISH, southern blotting, or PCR techniques.

(iv) Non-HER2 Overexpressing Cancer

While the cancer may be characterized by overexpression of the HER2 receptor, the present application further provides a method for treating cancer which is not considered to be a HER2-overexpressing.

To determine HER2 expression in the cancer, various diagnostic/prognostic assays are available. In one embodiment, HER2 overexpression may be analyzed by IHC, e.g. using the HERCEPTEST® (Dako). Parrafin embedded tissue sections from a tumor biopsy may be subjected to the IHC assay and accorded a HER2 protein staining intensity criteria as follows:

Score 0 no staining is observed or membrane staining is observed in less than 10% of tumor cells.

Score 1+ a faint/barely perceptible membrane staining is detected in more than 10% of the tumor cells. The cells are only stained in part of their membrane.

Score 2+ a weak to moderate complete membrane staining is observed in more than 10% of the tumor cells.

Score 3+ a moderate to strong complete membrane staining is observed in more than 10% of the tumor cells.

Those tumors with 0 or 1+ scores for HER2 overexpression assessment may be characterized as not overexpressing HER2, whereas those tumors with 2+ or 3+ scores may be characterized as overexpressing HER2.

Tumors overexpressing HER2 may be rated by immunohistochemical scores corresponding to the number of copies of HER2 molecules expressed per cell, and can been determined biochemically:

0=0-10,000 copies/cell,
1+=at least about 200,000 copies/cell,
2+=at least about 500,000 copies/cell,
3+=at least about 2,000,000 copies/cell.

Overexpression of HER2 at the 3+ level, which leads to ligand-independent activation of the tyrosine kinase (Hudziak et al., *Proc. Natl. Acad. Sci. USA,* 84:7159-7163 (1987)), occurs in approximately 30% of breast cancers, and in these patients, relapse-free survival and overall survival are diminished (Slamon et al., *Science,* 244:707-712 (1989); Slamon et al., *Science,* 235:177-182 (1987)). Alternatively, or additionally, FISH assays such as the INFORM™ (sold by Ventana, Arizona) or PATHVISION™ (Vysis, Illinois) may be carried out on formalin-fixed, paraffin-embedded tumor tissue to determine the extent (if any) of HER2 overexpression in the tumor.

In one embodiment, the cancer will be one which expresses (and may overexpress) EGFR, such expression may be evaluated as for the methods for evaluating HER2 expression as noted above.

HER receptor or HER ligand overexpression or amplification may also be evaluated using an in vivo diagnostic assay, e.g. by administering a molecule (such as an antibody) which binds the molecule to be detected and is tagged with a detectable label (e.g. a radioactive isotope) and externally scanning the patient for localization of the label.

VI. Treatment with the HER2 Antibody Composition

It is contemplated that, according to the present invention, the HER2 antibody may be used to treat cancer. The cancer will generally comprise HER2-expressing cells, such that the HER2 antibody herein is able to bind to the cancer cells. Various cancers that can be treated with the composition are listed in the definitions section above.

It is also contemplated that the HER2 antibody may be used to treat various non-malignant diseases or disorders, such as autoimmune disease (e.g. psoriasis); endometriosis; scleroderma; restenosis; polyps such as colon polyps, nasal polyps or gastrointestinal polyps; fibroadenoma; respiratory disease; cholecystitis; neurofibromatosis; polycystic kidney disease; inflammatory diseases; skin disorders including psoriasis and dermatitis; vascular disease; conditions involving abnormal proliferation of vascular epithelial cells; gastrointestinal ulcers; Menetrier's disease, secreting adenomas or protein loss syndrome; renal disorders; angiogenic disorders; ocular disease such as age related macular degeneration, presumed ocular histoplasmosis syndrome, retinal neovascularization from proliferative diabetic retinopathy, retinal vascularization, diabetic retinopathy, or age related macular degeneration; bone associated pathologies such as osteoarthritis, rickets and osteoporosis; damage following a cerebral ischemic event; fibrotic or edemia diseases such as hepatic cirrhosis, lung fibrosis, carcoidosis, throiditis, hyperviscosity syndrome systemic, Osler Weber-Rendu disease, chronic occlusive pulmonary disease, or edema following burns, trauma, radiation, stroke, hypoxia or ischemia; hypersensitivity reaction of the skin; diabetic retinopathy and diabetic nephropathy; Guillain-Barre syndrome; graft versus host disease or transplant rejection; Paget's disease; bone or joint inflammation; photoaging (e.g. caused by UV radiation of human skin); benign prostatic hypertrophy; certain microbial infections including microbial pathogens selected from adenovirus, hantaviruses, *Borrelia burgdorferi, Yersinia* spp. and *Bordetella pertussis*; thrombus caused by platelet aggregation; reproductive conditions such as endometriosis, ovarian hyperstimulation syndrome, preeclampsia, dysfunctional uterine bleeding, or menometrorrhagia; synovitis; atheroma; acute and chronic nephropathies (including proliferative glomerulonephritis and diabetes-induced renal disease); eczema; hypertrophic scar formation; endotoxic shock and fungal infection; familial adenomatosis polyposis; neurodedenerative diseases (e.g. Alzheimer's disease, AIDS-related dementia, Parkinson's disease, amyotrophic lateral sclerosis, retinitis pigmentosa, spinal muscular atrophy and cerebellar degeneration); myelodysplastic syndromes; aplastic anemia; ischemic injury; fibrosis of the lung, kidney or liver; T-cell mediated hypersensitivity disease; infantile hypertrophic pyloric stenosis; urinary obstructive syndrome; psoriatic arthritis; and Hasimoto's thyroiditis. Preferred non-malignant indications for therapy herein include psoriasis, endometriosis, scleroderma, vascular disease (e.g. restenosis, artherosclerosis, coronary artery disease, or hypertension), colon polyps, fibroadenoma or respiratory disease (e.g. asthma, chronic bronchitis, bronchieactasis or cystic fibrosis).

Treatment with the HER2 antibody will result in an improvement in the signs or symptoms of disease. For instance, where the disease being treated is cancer, such therapy may result in an improvement in survival (overall survival and/or progression free survival) and/or may result in an objective clinical response (partial or complete).

Preferably, the HER2 antibody in the composition administered is a naked antibody. However, the HER2 antibody administered may be conjugated with a cytotoxic agent. Preferably, the immunoconjugate and/or HER2 protein to which it is bound is/are internalized by the cell, resulting in increased therapeutic efficacy of the immunoconjugate in killing the cancer cell to which it binds. In a preferred embodiment, the cytotoxic agent targets or interferes with nucleic acid in the cancer cell. Examples of such cytotoxic agents include maytansinoids, calicheamicins, ribonucleases and DNA endonucleases.

The HER2 antibody is administered to a human patient in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous administration of antibody composition is preferred.

For the prevention or treatment of disease, the appropriate dosage of HER2 antibody will depend on the type of disease to be treated, as defined above, the severity and course of the disease, whether the HER2 antibody is administered for preventive or therapeutic purposes, previous therapy, the patient's clinical history and response to the HER2 antibody, and the discretion of the attending physician. The HER2 antibody is suitably administered to the patient at one time or over a series of treatments. Depending on the type and severity of the disease, about 1 µg/kg to 50 mg/kg (e.g. 0.1-20 mg/kg) of HER2 antibody is an initial candidate dosage for administration to the patient, whether, for example, by one or more separate administrations, or by continuous infusion. In one embodiment, the initial infusion time for the HER2 antibody may be longer than subsequent infusion times, for instance approximately 90 minutes for the initial infusion, and approximately 30 minutes for subsequent infusions (if the initial infusion is well tolerated). The preferred dosage of the HER2 antibody will be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, e.g. about six doses of the HER2 antibody). An initial higher loading dose, followed by one or more lower doses may be administered. In one embodiment, the HER2 antibody is administered as a loading dose of approximately 840 mg followed by approximately 420 mg approximately every 3 weeks. In another embodiment, the HER2 antibody is administered as a dose of approximately 1050 mg administered approximately every 3 weeks.

Other therapeutic agents may be combined with the HER2 antibody. Such combined administration includes coadministration or concurrent administration, using separate formulations or a single pharmaceutical formulation, and consecutive administration in either order, wherein preferably there is a time period while both (or all) active agents simultaneously exert their biological activities. Thus, the other therapeutic agent may be administered prior to, or following, administration of the HER2 antibody. In this embodiment, the timing between at least one administration of the other therapeutic agent and at least one administration of the HER2 antibody is preferably approximately 1 month or less, and most preferably approximately 2 weeks or less. Alternatively, the other therapeutic agent and the HER2 antibody are administered concurrently to the patient, in a single' formulation or separate formulations.

Examples of other therapeutic agents that can be combined with the HER2 antibody include any one or more of: a chemotherapeutic agent, such as an anti-metabolite, e.g. gemcitabine; a second, different HER2 antibody (for example, a growth inhibitory HER2 antibody such as Trastuzumab, or a HER2 antibody which induces apoptosis of a HER2-overexpressing cell, such as 7C2, 7F3 or humanized variants thereof); a second antibody directed against another tumor associated antigen, such as EGFR, HER3, HER4; anti-hormonal compound, e.g., an anti-estrogen compound such as tamoxifen, or an aromatase inhibitor; a cardioprotectant (to prevent or reduce any myocardial dysfunction associated with the therapy); a cytokine; an EGFR-targeted drug (such as TARCEVA®, IRESSA® or Cetuximab); an anti-angiogenic agent (especially Bevacizumab sold by Genentech under the trademark AVASTIN™); a tyrosine kinase inhibitor; a COX inhibitor (for instance a COX-1 or COX-2 inhibitor); non-steroidal anti-inflammatory drug, Celecoxib (CELEBREX®); farnesyl transferase inhibitor (for example, Tipifarnib/ZARNESTRA® R115777 available from Johnson and Johnson or Lonafarnib SCH66336 available from Schering- Plough); antibody that binds oncofetal protein CA 125 such as Oregovomab (MoAb B43.13); HER2 vaccine (such as HER2 AutoVac vaccine from Pharmexia, or APC8024 protein vaccine from Dendreon, or HER2 peptide vaccine from GSK/Corixa); another HER targeting therapy (e.g. trastuzumab, cetuximab, gefitinib, erlotinib, CI1033, GW2016 etc); Raf and/or ras inhibitor (see, for example, WO 2003/86467); Doxil; Topetecan; taxane; GW572016; TLK286; EMD-7200; a medicament that treats nausea such as a serotonin antagonist, steroid, or benzodiazepine; a medicament that prevents or treats skin rash or standard acne therapies, including topical or oral antibiotic; a body temperature-reducing medicament such as acetaminophen, diphenhydramine, or meperidine; hematopoietic growth factor, etc.

Suitable dosages for any of the above coadministered agents are those presently used and may be lowered due to the combined action (synergy) of the agent and HER2 antibody. Treatment with the combination of the HER2 antibody composition and other therapeutic agent may result in a synergistic, or greater than additive, therapeutic benefit to the patient.

If a chemotherapeutic agent is administered, it is usually administered at dosages known therefor, or optionally lowered due to combined action of the drugs or negative side effects attributable to administration of the chemotherapeutic agent. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

In addition to the above therapeutic regimes, the patient may be subjected to surgical removal of cancer cells and/or radiation therapy.

VII. Deposit of Materials

The following hybridoma cell lines have been deposited with the American Type Culture Collection, University Boulevard, Manassas, Va. 20110-2209, USA (ATCC):

| Antibody Designation | ATCC No. | Deposit Date |
|---|---|---|
| 7C2 | ATCC HB-12215 | Oct. 17, 1996 |
| 7F3 | ATCC HB-12216 | Oct. 17, 1996 |
| 4D5 | ATCC CRL 10463 | May 24, 1990 |
| 2C4 | ATCC HB-12697 | Apr. 8, 1999 |

Further details of the invention are illustrated by the following non-limiting Example. The disclosures of all citations in the specification are expressly incorporated herein by reference.

Example

Characterization of Pertuzumab Compositions

Pertuzumab is a recombinant humanized monoclonal antibody, generated based on human IgG1(κ) framework. It comprises two heavy chains (448 residues) and two light chains (214 residues). The two heavy chains are linked by two interchain disulfides and each light chain is attached to a heavy chain through one interchain disulfide. There is an N-linked glycosylation site in the Fc region of pertuzumab at Asn-299 of the two heavy chains. Pertuzumab differs from HERCEPTIN® (Trastuzumab) in the epitope binding regions of the light chain (12 amino acid differences) and the heavy chain (30 amino acid differences). As a result of these differences, pertuzumab binds to a completely different epitope on the HER2 receptor. Binding of pertuzumab to the HER2 receptor on human epithelial cells prevents it from forming complexes with other members of the HER receptor family (Agus et al., *Cancer Cell* 2:127-137 (2002)). By blocking complex formation, pertuzumab prevents the growth-stimulatory effects of ligands for the complexes (e.g., EGF and heregulin). In vitro experiments demonstrated that both pertuzumab and pertuzumab-Fab inhibit the binding of heregulin (HRG) to MCF7 cells, and that the HRG-stimulated phosphorylation of the HER2-HER3 complex can be inhibited by both pertuzumab and pertuzumab-Fab (Agus et al., *Cancer Cell* 2:127-137 (2002)). Furthermore, in vivo inhibition of tumor growth by pertuzumab and a polyethylene glycol derivatized Fab of pertuzumab were found to be comparable in a murine prostate cancer xenograft model (Agus et al., *Cancer Cell* 2:127-137 (2002)). These data suggest that the Fc region of the antibody is not necessary for the inhibition of tumor growth, and moreover, bivalency and Fc-mediated effector functions are not required for in vivo or in vitro biological activity.

The following samples expressed by recombinantly engineered Chinese Hamster Ovary (CHO) cells were analyzed:

| Sample | Manufacturing Process | Scale |
|---|---|---|
| Reference Material | Phase I | 400 L |
| Lot S9802A | Phase II | 2000 L |
| Process Development Materials (Runs 1, 2, 3, 5, and 6) | Clinical development program including Phase III | 400 L |

Note:
400 L Run 4 not available because of contamination at the 100 L inoculum culture at Day 2.

N-Terminal Sequence Analysis

N-terminal sequence analysis was performed using standard Edman degradation methods, and the results are shown in Table 2A, Table 2B, and Table 2C for the Reference Material, Lot S9802A, and the 400 L scale Run 1 process development material, respectively. The expected N-terminal sequences (FIG. 3A and FIG. 3B) of the light and heavy chains were observed in all samples. An additional minor sequence corresponding to the light chain with three additional amino acids Val-His-Ser (VHS) preceding the expected N-terminal sequence was also detected in the five samples. The VHS sequence is a portion of the signal peptide that is removed from protein as it is secreted. An alternate cleavage of the signal peptide results in the VHS extension at the N-terminus of pertuzumab. In the materials previously produced for Phase I/II clinical studies, about 2%-4% of the pertuzumab molecules have one of the two light chains containing the N-terminal VHS sequence. However, the level of light chains with N-terminal VHS sequence in these materials (1%-2% of each light chain) was too low to be detected in the N-terminal sequence analysis. In the five process development samples, the level of this light chain species is slightly above the detection limit of the N-terminal analysis at about 4%-5%. The N-terminal sequencing data for the five process development samples are consistent with the cation exchange chromatographic results, which show that the five process development samples have approximately 9% of the pertuzumab molecules with one light chain containing the VHS extension (see Cation Exchange Chromatography (CEC) below).

No other sequences were detected (limit of detection estimated at 3%), indicating the absence of internal cleavage sites.

Mass Spectrometric Analysis

The Pertuzumab samples were reduced with dithiothreitol and analyzed by electrospray-ionization mass spectrometry (ESI-MS) using a PE SCIEX API 3000™ mass spectrometer to confirm that the masses of the heavy and light chains are consistent with their expected sequences. The reconstructed mass spectra for the Reference Material, Lot S9802A, and the 400 L scale Run 1 process development material are compared in FIG. 8A and FIG. 8B. The observed light chain mass (23,524 Da) is consistent with the value predicted from its sequence for all three materials. Two additional minor peaks at 23,685 Da and 23,847 Da (161 and 323 Da higher than the light chain mass, respectively) were observed. The first peak (23,685 Da) is likely to arise from glycation in the light chain. The second peak (23,847 Da) is observed more clearly in the 400 L scale process development materials. This peak is presumably from the light chain with the Val-His-Ser extension (see the N-Terminal Sequence Analysis above and the Cation Exchange Chromatographic Analysis) or the light chain with two glycation sites.

Several masses corresponding to different forms of the heavy chain were observed. The predominant species of the heavy chain has a mass of 50,532 Da, arising from the heavy chain consisting of residues 1-448 with a G0 oligosaccharide structure. Other observed forms include the heavy chain containing residues 1-448 with a G1 or G2 oligosaccharide structure (FIG. 8B).

Charge Heterogeneity by Cation Exchange Chromatography and Capillary Zone Electrophoresis Cation exchange chromatography (CEC) was used to assess the charge heterogeneity in Pertuzumab. Samples, before and after treatment with carboxypeptidase B (CPB), were analyzed with a DIONEX™ cation exchange column (PROPAC WCX-10™, 4 mm×250 mm) using a pH 6.0, 20 mM MES buffer, and shallow NaCl gradient. The comparison of chromatograms are shown in FIG. 9A (before CPB treatment) and FIG. 9B (after CPB treatment). Multiple peaks were observed in all three lots. For characterization purposes, the chromatograms are divided into six regions (labeled A through F in FIGS. 9A and 9B). Relative peak areas for the six regions are listed in Table 3A and Table 3B. The amount of acidic variant (in region A) is higher in Lot S9802A and the 400 L scale process development materials than in the Reference Material. The basic variants in region C and D, which have been shown to contain Pertuzumab with a C-terminal lysine residue on one (region C) or both (region D) of the heavy chains, are reduced in Lot S9802A and the 400 L scale process development materials when compared to the Reference Material. After CPB treatment, the Pertuzumab molecules with one or two heavy chain C-terminal lysine were converted to main species in region B and no longer detected in region C and D. Only a small peak, whose identity has not yet been determined, remained in region C after CPB treatment. The basic variant in region E, shown to arise from the Pertuzumab molecules with one light chain containing the VHS extension, is higher in the 400 L scale process development materials (9%-10%) than in the Reference Material and Lot S9802A (4%). The basic variant in region F was shown to be Pertuzumab containing N-terminal VHS extension on one light chain and a C-terminal lysine on one heavy chain. As a result of higher levels of acidic and basic variants, the main species in region B is lower in the 400 L scale process development materials than in the Reference Material or Lot S9802A.

In addition to cation exchange chromatography, capillary zone electrophoresis (CZE) was employed to examine the charge heterogeneity in Pertuzumab. The CZE peaks was identified and correlated to those peaks observed in CEC analysis by analyzing individually collected CEC fractions with CZE. The relative amounts of charge variants determined by CZE and CEC are comparable for all the materials analyzed.

The biological activities of Pertuzumab charge variants in different CEC fractions appear to be the same based on a cell-based anti-proliferation assay. Thus, the charge heterogeneity in Pertuzumab is not expected to affect its potency. The biological activities of the 400 L process development materials are comparable to those of the Reference Material and Lot S9802A (see Biological Activity and Table 4).

Size-Exclusion Chromatography

Size-exclusion chromatography (SEC) was used to determine the extent of aggregation in Pertuzumab. Samples were analyzed on a TOSOHAAS TSK G3000SWXL™ column (7.8 mm×300 mm). Isocratic elution was used (100 mM potassium phosphate, pH 6.8, 0.5 mL/minutes) with ultraviolet (UV) absorbance monitored at 280 nm. SEC data for the Reference Material, Lot 59802A, and the 400 L scale Run 1 process development material are displayed in FIG. 10. The monomer is consistently at greater than 99.6% by peak area, and the aggregate is below 0.3% in all materials analyzed.

CE-SDS-LIF Analysis

Capillary electrophoresis-sodium dodecyl sulfate analysis with laser-induced fluorescence (CE-SDS-LIF) was also used to assess the purity of Pertuzumab samples. Similar electropherograms were observed for the Reference Material, Lot S9802A, and the 400 L scale Run 1 process development material with and without reduction (FIGS. 11A and 11B). The levels of non-glycosylated heavy chain determined from the electropherograms of reduced materials are between 2.6% and 4.3% (with respect to total heavy chain). The amounts of aggregates in these samples (non-reduced) determined by CE-SDS-LIF analysis are consistent with the SEC results. No evidence of significant product fragments or other impurities were found in the CE-SDS-LIF analysis of these samples. The CE-SDS-LIF data suggest that the impurity profile of the 400 L scale process development materials are similar to those of the Reference Material and Lot 59802A.

SDS-PAGE Analysis

The SDS-polyacrylamide gel electrophoresis (SDS-PAGE) analysis (4%-20% T gel (Daiichi Pure Chemicals Co., Tokyo, Japan) with SYPRORUBY™ staining) was performed to compare the reduced and intact samples of the Reference Material, Lot S9802A, and the 400 L scale process development materials. No new bands were observed in the 400 L scale process development materials, indicating again that the overall impurity profile in the 400 L scale process development materials are similar to the Reference Material and Lot S9802A.

Tryptic and LYS-C Peptide Map Analyses

Tryptic and Lys-C peptide map analyses were performed to examine and compare the primary structure of Pertuzumab in the Reference Material, Lot S9802A, and the 400 L scale process development materials. Aliquots of reduced and S-carboxymethylated Pertuzumab were digested with trypsin, and aliquots of reduced and sulfitolyzed Pertuzumab were digested with endoproteinase Lys-C. The trypsin digest was separated by reversed-phase chromatography using a VYDAC C-18™ column (4.6 mm×250 mm) with a 0%-60% acetonitrile gradient. Absorbance was monitored at 214 nm, and peptide masses were determined by ESI-MS using a THERMO FINNIGAN LCQ™. The Lys-C digest was separated by reversed-phase chromatography using a ZORBAX C-8™ column (4.6 mm×150 mm) with a 0%-100% isopropyl alcohol (IPA) gradient. Absorbance was monitored at 214 nm, and peptide masses were determined by ESI-MS using a THERMO FINNIGAN LCQ™.

The tryptic and Lys-C peptide maps for the Reference Material, Lot S9802A, and the 400 L scale Run 1 process development material are compared in FIG. 12A and FIG. 12B, respectively. Both tryptic and Lys-C maps for all three materials are essentially identical. The majority of the peptides were identified by LC-MS and matched to an expected peptide mass. The observed tryptic peptides identified 97.1% (436/449) of the heavy chain residues and 95.8% (205/214) of the light chain residues. The sequence coverage is 98.4% (442/449) and 70.6% (151/214) for the heavy and light chain, respectively, in the Lys-C map. The N-terminal peptide containing the VHS extension was found to co-elute with the N-terminal peptide without the VHS extension in the tryptic peptide map by LC-MS. No significant amounts of deamidated or oxidized peptides were detected in the peptide maps.

Biological Activity

The biological activity of Pertuzumab was determined by measuring its ability to inhibit proliferation of the human breast cancer cell line MDA-MB-175-VII. The percent specific activities obtained for five 400 L scale process development samples (Table 4) are in the range of 90%-96% and similar to the activities for the Reference Material (100% by definition) and Lot 59802A (98% reported in Certificate of Analysis). As expected, the charge heterogeneity does not affect the potency of Pertuzumab. All materials have comparable anti-proliferation activities.

N-Linked Oligosaccharide Analysis

Part of the mass heterogeneity in the heavy chain arises from the glycosylation at Asn-299. To assess the heterogeneity of the oligosaccharides, Pertuzumab samples were digested overnight with PNGase F to release the N-linked glycans. The released oligosaccharides were then derivatized with the fluorophore 9-amino-1,4,6-trisulfonate (APTS). Individual glycan forms were separated by capillary electrophoresis (CE) (Beckman P/ACE 5500 CE equipped with Beckman coated capillary) and quantified with fluorescence detection.

The electropherograms from CE analysis of the released neutral oligosaccharides from the Reference Material, Lot S9802A, and the 400 L scale Run 1 process development material are shown in FIG. 13. For reference, the oligosaccharide structures commonly found in human IgG1 antibodies, and a summary of the nomenclature used are included in FIG. 14. Relative amounts of oligosaccharides in all materials are summarized in Table 5.

The oligosaccharides with G0 and G1 structures are the predominant glycans. Peaks arising from other oligosaccharide structures were also observed in the electropherograms. These structures include G2, G0-F, G-1, Man5, and G1-1 (or Man6) glycoforms. In addition, the isoforms are resolved. The distributions of observed glycans are similar in all materials (Table 5). However, compared to the Reference Materials and 400 L scale process development materials, the Phase II material (Lot S9802A) has a smaller amount of glycans with a G0 structure and more glycans with G1 structure. Despite the differences in glycan distribution, all materials have similar biological activities. In addition, the change in glycan heterogeneity did not have a significant impact on the binding affinity of Pertuzumab for FcRn (Table 6) or Fc gamma receptors (Table 7) (see FcRn Receptor and Fc Gamma Receptor Binding Assays).

The released neutral oligosaccharides were also analyzed by MALDI-TOF mass spectrometry (MALDI-TOF/MS). The MALDI-TOF spectra for the released neutral oligosaccharides from the Reference Material, Lot S9802A, and 400 L scale Run 1 process development material are compared in FIG. 15. The glycan structure and distribution obtained from MALDI-TOF/MS analysis are consistent with the CE results.

Capillary Isoelectric Focusing Analysis

Capillary isoelectric focusing (cIEF) was used to determine the pI of Pertuzumab in the Reference Material, Lot S9802A, and the 400 L scale Run 1 process development material. Although the relative amounts of the different charged species in these materials were somewhat different as observed in the CEC analysis, the pI of the main species was found to be 8.7 in all samples.

Free Sulfhydryl Analysis

The Reference Material, Lot S9802A, and the 400 L scale process development materials were tested for free thiol (unpaired cysteine residue) using the Ellman's analysis. Free thiol level was below the limit of detection (approximately 0.05 mole free thiol per mole protein) in all materials tested.

FcRn Receptor Binding Assay

The FcRn receptor binding affinities of Pertuzumab from the Reference Material, Lot S9802A, and the 400 L scale process development materials were compared using an ELISA assay similar to the one described in Shields et al., *J. Biol. Chem.* 276:6591-6604 (2001). The Reference Material was used as a standard in this assay.

MAXISORP™ 96-well microwell plates (Nunc, Roskilde, Denmark) were first coated with NEUTRAVADIN™ (Pierce, Rockford, Ill.) at 4° C. overnight. Biotinylated human FcRn was then added to the plates at 2 µg/mL and incubated for one hour. Eleven two-fold serial dilutions of Pertuzumab samples (3.1-3200 ng/mL) were added to the plates and incubated for two hours. Bound Pertuzumab was detected by adding peroxidase labeled goat F(ab')$_2$ anti-human IgG F(ab')$_2$ (Jackson ImmunoResearch, West Grove, Pa.) and using 3,3',5,5'-tetramethyl benzidine (TMB) (Kirkegaard & Perry Laboratories, Gaithersburg, Md.) as the substrate. Absorbance was read at 450 nm on a TITERTEK MULTISKAN™ (MCC/340) reader (ICN, Costa Mesa, Calif.). The FcRn binding affinity of Pertuzumab was also evaluated in a second ELISA format in which HER2-ECD was coated on plates. Serially diluted Pertuzumab samples were added to the plates and incubated for two hours. Plates were washed and 2 mg/mL of biotinylated human FcRn were added. Bound FcRn was detected using streptavidin-HRP with TMB as the substrate.

The absorbance at the midpoint of the titration curve (mid-OD) of standard (i.e., Reference Material) and the corresponding concentrations of standard and samples at this mid-OD were determined. The relative binding affinity was calculated by dividing the mid-OD concentration of standard by that of the sample.

The relative FcRn binding affinities obtained from both ELISA formats are listed in Table 6. Data from the two different ELISA formats are comparable. Although the glycan distributions in different Pertuzumab materials are not identical, the FcRn binding affinities of these materials are comparable, indicating that the glycan heterogeneity in Pertuzumab has no apparent effect on its FcRn binding affinity.

Fc Gamma Receptor Binding Assay

Binding of Pertuzumab to the human Fc gamma receptors (FcγR) was assessed by an ELISA assay according to Shields et al., *J. Biol. Chem.* 276:6591-6604 (2001) with modifications.

Monomeric IgG can bind to the high-affinity FcγRIa (CD64); however, the low-affinity receptors (FcγRIIa (CD32A), FcγRIIb (CD32B), and FcγRIIIa (CD16)) require multimeric IgG for significant binding. Therefore, for the low-affinity receptor binding assays, multimers of Pertuzumab were formed before assay by mixing each sample (200 mg/mL) with goat anti-human kappa chain (400 mg/mL; ICN Biomedical, Irvine, Calif.). The human FcγR were expressed as recombinant fusion proteins of the extracellular domain of the receptor alpha chains with Gly/His6/GST (glycine/6 histidines/glutathione-s-transferase) Anti-GST-coated, bovine serum albumin (BSA)-blocked assay plates were used to capture the FcγR. The receptors (100 mL at 0.25 mg/mL) were added to the plates and incubated for 1 hour. Serial dilutions of Pertuzumab samples (100 mL) were added as monomers for FcγRIa and as multimers for the low-affinity FcγR, and the plates were incubated for two hours. The bound Pertuzumab was detected by adding horseradish peroxidase-conjugated goat anti-human F(ab')$_2$ (Jackson ImmunoResearch Laboratories, West Grove, Pa.) and using TMB as substrate. $EC_{50}$ values for binding of Pertuzumab to the FcγR were determined by nonlinear regression analysis with a four-parameter model (KaleidaGraph, Synergy Software, Reading, Pa.). RITUXAN® (Lot C2B81298-2) was used as the control antibody.

The $EC_{50}$ values for binding of Pertuzumab to FcγR are summarized in Table 7. The results show that the Reference Material, Lot S9802A, and the 400 L scale process development materials have comparable binding affinities for FcγR. These results suggest that the glycan heterogeneity in Pertuzumab has no significant effect on its FcγR-binding affinities.

TABLE 2A

N-Terminal Sequence Analysis of Pertuzumab Reference Material (nmol of residue observed in each cycle)

| Residue | Cycle | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| ALA | 0.01 | 0.01 | 0.02 | 0.04 | 0.04 | 0.05 | 0.06 | 0.07 | 0.09 | 0.09 | 0.10 | 0.11 |
| ARG | 0.01 | 0.01 | 0.01 | 0.01 | 0.03 | 0.03 | 0.04 | 0.04 | 0.05 | 0.06 | 0.05 | 0.06 |
| ASN | 0.00 | 0.00 | 0.01 | 0.01 | 0.01 | 0.02 | 0.03 | 0.04 | 0.05 | 0.06 | 0.06 | 0.07 |
| ASP | 0.48 | 0.08 | 0.03 | 0.04 | 0.04 | 0.04 | 0.05 | 0.07 | 0.07 | 0.08 | 0.09 | 0.10 |
| CYS | NA | NA | NA | NA | NA | NA | NA | NA | NA | NA | NA | NA |
| GLN | 0.00 | 0.01 | 0.92 | 0.13 | 0.04 | 0.46 | 0.13 | 0.07 | 0.08 | 0.08 | 0.08 | 0.09 |
| GLU | 0.49 | 0.05 | 0.13 | 0.03 | 0.03 | 0.51 | 0.12 | 0.07 | 0.07 | 0.07 | 0.07 | 0.08 |
| GLY | 0.01 | 0.01 | 0.03 | 0.03 | 0.05 | 0.05 | 0.05 | 0.30 | 0.35 | 0.36 | 0.13 | 0.09 |
| HIS | 0.00 | 0.00 | 0.00 | 0.00 | 0.01 | 0.01 | 0.01 | 0.01 | 0.01 | 0.01 | 0.01 | 0.02 |
| ILE | 0.00 | 0.48 | 0.06 | 0.02 | 0.03 | 0.03 | 0.03 | 0.03 | 0.03 | 0.04 | 0.04 | 0.04 |
| LEU | 0.00 | 0.03 | 0.04 | 0.43 | 0.11 | 0.08 | 0.09 | 0.11 | 0.12 | 0.13 | 0.62 | 0.26 |
| LYS | 0.00 | 0.00 | 0.03 | 0.00 | 0.05 | 0.06 | 0.07 | 0.08 | 0.08 | 0.09 | 0.00 | 0.12 |
| MET | 0.00 | 0.00 | 0.00 | 0.53 | 0.07 | 0.02 | 0.02 | 0.02 | 0.02 | 0.02 | 0.02 | 0.02 |
| PHE | 0.00 | 0.01 | 0.02 | 0.02 | 0.03 | 0.04 | 0.05 | 0.05 | 0.06 | 0.07 | 0.07 | 0.08 |
| PRO | 0.00 | 0.01 | 0.02 | 0.03 | 0.04 | 0.04 | 0.05 | 0.32 | 0.13 | 0.09 | 0.09 | 0.10 |
| SER | 0.01 | 0.01 | 0.03 | 0.04 | 0.05 | 0.07 | 0.56 | 0.16 | 0.30 | 0.33 | 0.18 | 0.28 |
| THR | 0.00 | 0.01 | 0.00 | 0.04 | 0.33 | 0.12 | 0.07 | 0.07 | 0.08 | 0.09 | 0.10 | 0.10 |
| TRP | 0.00 | 0.00 | 0.00 | 0.00 | 0.00 | 0.01 | 0.01 | 0.01 | 0.01 | 0.02 | 0.02 | 0.02 |
| TYR | 0.01 | 0.01 | 0.03 | 0.04 | 0.05 | 0.06 | 0.08 | 0.08 | 0.09 | 0.10 | 0.11 | 0.13 |
| VAL | 0.01 | 0.51 | 0.08 | 0.10 | 0.53 | 0.15 | 0.11 | 0.12 | 0.14 | 0.15 | 0.16 | 0.51 |
| Light Chain | ASP | ILE | GLN | MET | THR | GLN | SER | PRO | SER | SER | LEU | SER |
| Heavy Chain | GLU | VAL | GLN | LEU | VAL | GLU | SER | GLY | GLY | GLY | LEU | VAL |

Note:
The nanomoles of phenylthiohydantoin amino acid residues observed in each cycle is given. Residues from the heavy chain are given in bold type, and residues from the light chain are underlined. Approximately 0.5 nmol of protein was loaded, equivalent to 1.0 nmol of each of the light and heavy chains. Cysteine (CYS) is not observed in the sequence analysis.

TABLE 2B

N-Terminal Sequence Analysis of Pertuzumab Lot S9802A (nmol of residue observed in each cycle)

| Residue | Cycle | | | | | | | | | | | |
|---|---|---|---|---|---|---|---|---|---|---|---|---|
| | 1 | 2 | 3 | 4 | 5 | 6. | 7 | 8 | 9 | 10 | 11 | 12 |
| ALA | 0.01 | 0.01 | 0.03 | 0.04 | 0.06 | 0.06 | 0.08 | 0.09 | 0.11 | 0.12 | 0.14 | 0.14 |
| ARG | 0.01 | 0.01 | 0.02 | 0.02 | 0.03 | 0.03 | 0.05 | 0.05 | 0.06 | 0.07 | 0.07 | 0.08 |
| ASN | 0.00 | 0.00 | 0.01 | 0.02 | 0.02 | 0.02 | 0.04 | 0.05 | 0.06 | 0.07 | 0.08 | 0.09 |
| ASP | 0.61 | 0.12 | 0.04 | 0.05 | 0.05 | 0.06 | 0.07 | 0.09 | 0.09 | 0.10 | 0.11 | 0.13 |
| CYS | NA | NA | NA | NA | NA | NA | NA | NA | NA | NA | NA | NA |
| GLN | 0.00 | 0.01 | 1.11 | 0.22 | 0.06 | 0.55 | 0.19 | 0.10 | 0.11 | 0.11 | 0.11 | 0.12 |
| GLU | 0.61 | 0.09 | 0.15 | 0.05 | 0.04 | 0.61 | 0.19 | 0.10 | 0.09 | 0.10 | 0.10 | 0.11 |
| GLY | 0.01 | 0.01 | 0.04 | 0.04 | 0.06 | 0.06 | 0.07 | 0.37 | 0.44 | 0.46 | 0.19 | 0.13 |
| HIS | 0.00 | 0.01 | 0.01 | 0.01 | 0.01 | 0.01 | 0.01 | 0.01 | 0.01 | 0.02 | 0.02 | 0.02 |
| ILE | 0.00 | 0.56 | 0.10 | 0.02 | 0.04 | 0.04 | 0.03 | 0.04 | 0.05 | 0.05 | 0.05 | 0.06 |
| LEU | 0.00 | 0.04 | 0.05 | 0.51 | 0.17 | 0.11 | 0.12 | 0.14 | 0.15 | 0.17 | 0.76 | 0.37 |
| LYS | 0.00 | 0.00 | 0.04 | 0.00 | 0.06 | 0.08 | 0.09 | 0.10 | 0.11 | 0.12 | 0.00 | 0.16 |
| MET | 0.00 | 0.00 | 0.01 | 0.61 | 0.12 | 0.03 | 0.03 | 0.03 | 0.02 | 0.02 | 0.02 | 0.03 |
| PHE | 0.00 | 0.01 | 0.03 | 0.03 | 0.04 | 0.05 | 0.06 | 0.07 | 0.08 | 0.09 | 0.09 | 0.10 |
| PRO | 0.00 | 0.01 | 0.02 | 0.03 | 0.05 | 0.06 | 0.06 | 0.37 | 0.18 | 0.12 | 0.12 | 0.13 |
| SER | 0.01 | 0.02 | 0.04 | 0.05 | 0.06 | 0.08 | 0.63 | 0.24 | 0.36 | 0.41 | 0.24 | 0.35 |

TABLE 2B-continued

N-Terminal Sequence Analysis of Pertuzumab Lot S9802A (nmol of residue observed in each cycle)

| Residue | 1 | 2 | 3 | 4 | 5 | 6. | 7 | 8 | 9 | 10 | 11 | 12 |
|---|---|---|---|---|---|---|---|---|---|---|---|---|
| THR | 0.00 | 0.01 | 0.00 | 0.05 | 0.39 | 0.17 | 0.10 | 0.10 | 0.11 | 0.12 | 0.13 | 0.14 |
| TRP | 0.00 | 0.00 | 0.00 | 0.00 | 0.01 | 0.01 | 0.01 | 0.02 | 0.02 | 0.02 | 0.02 | 0.02 |
| TYR | 0.16 | 0.07 | 0.05 | 0.06 | 0.07 | 0.08 | 0.10 | 0.10 | 0.12 | 0.13 | 0.14 | 0.16 |
| VAL | 0.02 | 0.58 | 0.13 | 0.12 | 0.62 | 0.22 | 0.15 | 0.16 | 0.18 | 0.20 | 0.21 | 0.62 |
| Light Chain | ASP | ILE | GLN | MET | THR | GLN | SER | PRO | SER | SER | LEU | SER |
| Heavy Chain | GLU | VAL | GLN | LEU | VAL | GLU | SER | GLY | GLY | GLY | LEU | VAL |

Note:
The nanomoles of phenylthiohydantoin amino acid residues observed in each cycle is given. Residues from the heavy chain are given in bold type, and residues from the light chain are underlined. Approximately 0.5 nmol of protein was loaded, equivalent to 1.0 nmol of each of the light and heavy chains. Cysteine (CYS) is not observed in the sequence analysis.

TABLE 2C

N-Terminal Sequence Analysis of Pertuzumab 400 L Scale Run 1 (nmol of residue observed in each cycle)

| Residue | 1 | 2 | 3 | 4 | 5 | 6 | 7 | 8 | 9 | 10 | 11 | 12 |
|---|---|---|---|---|---|---|---|---|---|---|---|---|
| ALA | 0.01 | 0.02 | 0.03 | 0.05 | 0.06 | 0.06 | 0.08 | 0.10 | 0.11 | 0.13 | 0.14 | 0.14 |
| ARG | 0.03 | 0.05 | 0.07 | 0.09 | 0.17 | 0.15 | 0.20 | 0.23 | 0.24 | 0.29 | 0.30 | 0.33 |
| ASN | 0.00 | 0.00 | 0.01 | 0.02 | 0.02 | 0.03 | 0.04 | 0.06 | 0.07 | 0.08 | 0.09 | 0.09 |
| ASP | 0.89 | 0.08 | 0.05 | *0.11* | 0.08 | 0.09 | 0.11 | 0.15 | 0.14 | 0.16 | 0.18 | 0.19 |
| CYS | NA | NA | NA | NA | NA | NA | NA | NA | NA | NA | NA | NA |
| GLN | 0.00 | 0.01 | 1.17 | 0.11 | 0.05 | 0.60 | 0.12 | 0.09 | *0.14* | 0.12 | 0.11 | 0.12 |
| GLU | 0.68 | 0.05 | 0.19 | 0.04 | 0.04 | 0.62 | 0.15 | 0.10 | 0.10 | 0.11 | 0.11 | 0.12 |
| GLY | 0.01 | 0.01 | 0.01 | 0.05 | 0.04 | 0.08 | 0.07 | 0.37 | 0.42 | 0.44 | 0.16 | 0.13 |
| HIS | 0.00 | *0.02* | 0.01 | 0.01 | 0.01 | 0.01 | 0.02 | 0.02 | 0.02 | 0.03 | 0.03 | 0.03 |
| ILE | 0.00 | 0.56 | 0.03 | 0.02 | *0.07* | 0.04 | 0.03 | 0.04 | 0.05 | 0.06 | 0.05 | 0.06 |
| LEU | 0.00 | 0.04 | 0.05 | 0.51 | 0.15 | 0.12 | 0.13 | 0.15 | 0.16 | 0.18 | 0.79 | 0.31 |
| LYS | 0.00 | 0.00 | 0.04 | 0.05 | 0.08 | 0.09 | 0.10 | 0.12 | 0.14 | 0.15 | 0.17 | 0.19 |
| MET | 0.00 | 0.00 | 0.01 | 0.65 | 0.04 | 0.02 | *0.05* | 0.03 | 0.02 | 0.02 | 0.03 | 0.03 |
| PHE | 0.00 | 0.01 | 0.03 | 0.03 | 0.05 | 0.05 | 0.07 | 0.08 | 0.08 | 0.09 | 0.10 | 0.11 |
| PRO | 0.00 | 0.01 | 0.02 | 0.04 | 0.05 | 0.06 | 0.07 | 0.41 | 0.14 | 0.11 | *0.13* | 0.14 |
| SER | 0.01 | 0.02 | *0.07* | 0.06 | 0.08 | 0.10 | 0.76 | 0.21 | 0.43 | *0.48* | 0.23 | 0.42 |
| THR | 0.00 | 0.01 | 0.00 | 0.06 | 0.57 | 0.18 | 0.12 | *0.16* | 0.16 | 0.17 | 0.18 | 0.19 |
| TRP | 0.00 | 0.00 | 0.00 | 0.00 | 0.01 | 0.01 | 0.01 | 0.02 | 0.02 | 0.02 | 0.03 | 0.03 |
| TYR | 0.00 | 0.02 | 0.04 | 0.06 | 0.07 | 0.08 | 0.10 | 0.11 | 0.13 | 0.14 | 0.15 | 0.17 |
| VAL | *0.04* | 0.56 | 0.10 | 0.13 | 0.62 | 0.19 | 0.15 | 0.17 | 0.19 | 0.21 | 0.22 | 0.62 |
| Light Chain | ASP | ILE | GLN | MET | THR | GLN | SER | PRO | SER | SER | LEU | SER |
| Heavy Chain | GLU | VAL | GLN | LEU | VAL | GLU | SER | GLY | GLY | GLY | LEU | VAL |
| VHS-Light Chain | *VAL* | *HIS* | *SER* | *ASP* | *ILE* | *GLN* | *MET* | *THR* | *GLN* | *SER* | *PRO* | *SER* |

Note:
The nanomoles of phenylthiohydantoin amino acid residues observed in each cycle is given. Residues from the heavy chain are given in bold type, and residues from the light chain are underlined. Residues from the additional VHS-light chain sequence are shown in italics. Approximately 0.5 nmol of protein was loaded, equivalent to 1.0 nmol of each of the light and heavy chains. Cysteine (CYS) is not observed in the sequence analysis. 0

TABLE 3A

Cation Exchange Chromatographic Analysis of Native Pertuzumab (% peak area)

| Sample | A | B | C | D | E | F |
|---|---|---|---|---|---|---|
| Reference Material | 10 | 73 | 10 | 3 | 3 | 0.4 |
| S9802A | 20 | 68 | 5 | 2 | 4 | 0.2 |
| 400 L Scale Run 1 | 16 | 65 | 5 | 2 | 10 | 0.9 |
| 400 L Scale Run 2 | 15 | 67 | 5 | 2 | 9 | 0.6 |
| 400 L Scale Run 3 | 15 | 67 | 6 | 2 | 10 | 0.6 |
| 400 L Scale Run 5 | 15 | 67 | 5 | 2 | 9 | 0.5 |
| 400 L Scale Run 6 | 13 | 63 | 9 | 3 | 9 | 0.6 |

Note:
400 L Run 4 not available because of contamination of the 100 L inoculum culture at Day 2.

TABLE 3B

Cation Exchange Chromatographic Analysis of CPB-Digested Pertuzumab (% peak area)

| Sample | A | B | C | D | E | F |
|---|---|---|---|---|---|---|
| Reference Material | 11 | 78 | 4 | ND | 4 | ND |
| S9802A | 20 | 71 | 3 | ND | 4 | ND |
| 400 L Scale Run 1 | 17 | 68 | 3 | ND | 10 | ND |
| 400 L Scale Run 2 | 15 | 71 | 3 | ND | 9 | ND |
| 400 L Scale Run 3 | 15 | 71 | 3 | ND | 10 | ND |
| 400 L Scale Run 5 | 17 | 70 | 3 | ND | 9 | ND |
| 400 L Scale Run 6 | 16 | 71 | 3 | ND | 9 | ND |

Note:
Fractions A through F are defined in FIG. 9B. All values are rounded to two significant figures. Totals in any row may not add to 100% because of rounding.
400 L Run 4 not available because of contamination of the 100 L inoculum culture at Day 2.
ND = Not detected or cannot be integrated.

TABLE 4

Specific Activities of Pertuzumab by a Cell-Based Anti-Proliferation Assay

| Material | Specific Activity (%) | % CV |
|---|---|---|
| Reference Material | 100[a] | — |
| S9802A | 98[b] | 10 |
| 400 L Scale Run 1 | 96[c] | 18 |
| 400 L Scale Run 2 | 90[c] | 11 |
| 400 L Scale Run 3 | 96[c] | 17 |
| 400 L Scale Run 5 | 96[c] | 3 |
| 400 L Scale Run 6 | 95[c] | 3 |

Note:
400 L Run 4 not available because of contamination of the 100 L inoculum culture at Day 2.
[a]By definition, specific activity of Reference Material is 100%.
[b]Value reported for Lot S9802A.
[c]Value represents mean of three assays.

TABLE 5

Distribution of Oligosaccharide Structures in Pertuzumab Determined by CE

| Sample | % G0-F | % G-1 | % Man5 | % G0 | % Man6 + % G1-1 | % G1[a] | % G2 |
|---|---|---|---|---|---|---|---|
| Reference Material | 1 | 4 | 1 | 71 | 2 | 19 | 2 |
| S9802A | 1 | 4 | 1 | 62 | 2 | 27 | 3 |
| 400 L Scale Run 1 | 2 | 6 | 1 | 73 | 3 | 15 | 2 |
| 400 L Scale Run 2 | 1 | 6 | 1 | 77 | 2 | 13 | 1 |
| 400 L Scale Run 3 | 2 | 6 | 1 | 74 | 4 | 14 | 1 |
| 400 L Scale Run 5 | 1 | 5 | 1 | 71 | 2 | 18 | 1 |
| 400 L Scale Run 6 | 1 | 5 | 1 | 71 | 3 | 18 | 1 |

Note:
400 L Run 4 not available because of contamination of the 100 L inoculum culture at Day 2.
[a]Sum of the two G1 isomers.

TABLE 6

Relative Binding Affinities of Pertuzumab for FcRn

| | Relative Binding Affinity[a] | |
|---|---|---|
| Sample | NeutrAvidin Coat Format | Her2ECD Coat Format |
| Reference Material (Standard) | 1.00 | 1.00 |
| S9802A | 1.34 | 1.30 |
| 400 L Scale Run 1 | 1.04 | 1.22 |
| 400 L Scale Run 2 | 1.09 | 1.31 |
| 400 L Scale Run 3 | 1.14 | 1.42 |
| 400 L Scale Run 5 | 1.22 | 1.36 |
| 400 L Scale Run 6 | 1.06 | 1.29 |

Note:
400 L Run 4 not available because of contamination of the 100 L inoculum culture at Day 2.
[a]The absorbance at the midpoint of the titration curve (mid-OD) of standard (i.e., Reference Material) and the corresponding concentrations of standard and samples at this mid-OD were determined. The relative binding affinity was obtained by dividing the mid-OD concentration of standard by that of the sample.

TABLE 7

$EC_{50}$ Values for Binding of Pertuzumab to Fc Gamma Receptors

| | $EC_{50}$ (µg/mL) | | | | | | | | | |
|---|---|---|---|---|---|---|---|---|---|---|
| | FcγR Ia | | FcγRIIa | | FcγRIIb | | FcγRIIIa (F158) | | FcγRIIIa (V158) | |
| Sample | Mean | SD | Mean | SD | Mean | SD | Mean | SD | Mean | SD |
| Reference Material | 0.0081 | 0.0014 | 5.8 | 1.8 | 57 | 17 | 14.0 | 1.4 | 1.8 | 0.1 |
| S9802A | 0.0078 | 0.0020 | 5.4 | 1.9 | 45 | 17 | 7.8 | 0.3 | 1.1 | 0.1 |
| 400 L Scale Run 1 | 0.0079 | 0.0013 | 5.4 | 1.5 | 70 | 25 | 8.4 | 0.9 | 1.2 | 0.1 |
| 400 L Scale Run 2 | 0.0074 | 0.0016 | 5.8 | 1.6 | 54 | 18 | 10.4 | 0.7 | 1.4 | 0.2 |

TABLE 7-continued

EC$_{50}$ Values for Binding of Pertuzumab to Fc Gamma Receptors

| | EC$_{50}$ (µg/mL) | | | | | | | | | |
|---|---|---|---|---|---|---|---|---|---|---|
| | FcγR Ia | | FcγRIIa | | FcγRIIb | | FcγRIIIa (F158) | | FcγRIIIa (V158) | |
| Sample | Mean | SD | Mean | SD | Mean | SD | Mean | SD | Mean | SD |
| 400 L Scale Run 3 | 0.0075 | 0.0015 | 5.5 | 1.1 | 54 | 10 | 8.2 | 0.9 | 1.2 | 0.1 |
| 400 L Scale Run 5 | 0.0076 | 0.0011 | 6.1 | 2.7 | 50 | 12 | 10.9 | 1.5 | 1.4 | 0.2 |
| 400 L Scale Run 6 | 0.0080 | 0.0005 | 6.2 | 1.9 | 44 | 1 | 10.3 | 0.9 | 1.4 | 0.2 |

Note:
The means and standard deviations (SD) were obtained from multiple runs of the assay (N = 4).
FcγRIIIa receptor has two versions: F158 and V158.
400 L Run 4 not available because of contamination of the 100 L inoculum culture at Day 2.

What is claimed is:

1. A method of treating HER2-expressing cancer in a patient comprising administering a pharmaceutical formulation to the patient in an amount effective to treat the cancer, wherein the formulation comprises a composition comprising: (a) a main species HER2 antibody that binds to domain II of HER2 and comprises the variable light amino acid sequence in SEQ ID No. 3 and the variable heavy amino acid sequence in SEQ ID No. 4, and (b) the main species HER2 antibody comprising an amino-terminal leader extension, wherein the amino-terminal leader extension comprises VHS-, wherein from 5% to about 15% of the antibody molecules in the composition comprise the amino-terminal leader extension, as quantified by cation exchange analysis in a pharmaceutically acceptable carrier.

2. A method of treating HER2-expressing cancer in a patient comprising administering a pharmaceutical formulation to the patient in an amount effective to treat the cancer, wherein the formulation comprises a composition comprising: (a) a main species HER2 antibody comprising the variable light sequence in SEQ ID No. 3 and the variable heavy sequence in SEQ ID No. 4, and (b) the main species antibody comprising a VHS-amino-terminal leader extension attached to one or two variable light domains thereof, wherein from 5% to about 20% of antibody molecules in the composition comprise the VHS-amino-terminal leader extension in a pharmaceutically acceptable carrier.

* * * * *

SEQUENCE LISTING

<160> NUMBER OF SEQ ID NOS: 24

<210> SEQ ID NO 1
<211> LENGTH: 107
<212> TYPE: PRT
<213> ORGANISM: Mus musculus

<400> SEQUENCE: 1

Asp Thr Val Met Thr Gln Ser His Lys Ile Met Ser Thr Ser Val
 1               5                  10                  15

Gly Asp Arg Val Ser Ile Thr Cys Lys Ala Ser Gln Asp Val Ser
                20                  25                  30

Ile Gly Val Ala Trp Tyr Gln Gln Arg Pro Gly Gln Ser Pro Lys
                35                  40                  45

Leu Leu Ile Tyr Ser Ala Ser Tyr Arg Tyr Thr Gly Val Pro Asp
                50                  55                  60

Arg Phe Thr Gly Ser Gly Ser Gly Thr Asp Phe Thr Phe Thr Ile
                65                  70                  75

Ser Ser Val Gln Ala Glu Asp Leu Ala Val Tyr Tyr Cys Gln Gln
                80                  85                  90

Tyr Tyr Ile Tyr Pro Tyr Thr Phe Gly Gly Gly Thr Lys Leu Glu
                95                  100                 105

Ile Lys

<210> SEQ ID NO 2
<211> LENGTH: 119
<212> TYPE: PRT
<213> ORGANISM: Mus musculus

<400> SEQUENCE: 2

Glu Val Gln Leu Gln Gln Ser Gly Pro Glu Leu Val Lys Pro Gly
 1               5                  10                  15

Thr Ser Val Lys Ile Ser Cys Lys Ala Ser Gly Phe Thr Phe Thr
                20                  25                  30

Asp Tyr Thr Met Asp Trp Val Lys Gln Ser His Gly Lys Ser Leu
                35                  40                  45

Glu Trp Ile Gly Asp Val Asn Pro Asn Ser Gly Gly Ser Ile Tyr
                50                  55                  60

Asn Gln Arg Phe Lys Gly Lys Ala Ser Leu Thr Val Asp Arg Ser
                65                  70                  75

Ser Arg Ile Val Tyr Met Glu Leu Arg Ser Leu Thr Phe Glu Asp
            80                  85                  90

Thr Ala Val Tyr Tyr Cys Ala Arg Asn Leu Gly Pro Ser Phe Tyr
            95                  100                 105

Phe Asp Tyr Trp Gly Gln Gly Thr Thr Leu Thr Val Ser Ser
            110                 115

<210> SEQ ID NO 3
<211> LENGTH: 107
<212> TYPE: PRT
<213> ORGANISM: Artificial Sequence
<220> FEATURE:
<223> OTHER INFORMATION: sequence is synthesized

<400> SEQUENCE: 3

Asp Ile Gln Met Thr Gln Ser Pro Ser Ser Leu Ser Ala Ser Val
 1               5                  10                  15

Gly Asp Arg Val Thr Ile Thr Cys Lys Ala Ser Gln Asp Val Ser
                20                  25                  30

Ile Gly Val Ala Trp Tyr Gln Gln Lys Pro Gly Lys Ala Pro Lys
                35                  40                  45

Leu Leu Ile Tyr Ser Ala Ser Tyr Arg Tyr Thr Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Tyr Ile Tyr Pro Tyr Thr Phe Gly Gln Gly Thr Lys Val Glu
                95                  100                 105

Ile Lys

<210> SEQ ID NO 4
<211> LENGTH: 119
<212> TYPE: PRT
<213> ORGANISM: Artificial Sequence
<220> FEATURE:
<223> OTHER INFORMATION: sequence is synthesized

<400> SEQUENCE: 4

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Thr
                20                  25                  30

Asp Tyr Thr Met Asp Trp Val Arg Gln Ala Pro Gly Lys Gly Leu
                35                  40                  45

Glu Trp Val Ala Asp Val Asn Pro Asn Ser Gly Gly Ser Ile Tyr
                50                  55                  60

Asn Gln Arg Phe Lys Gly Arg Phe Thr Leu Ser Val Asp Arg Ser
                65                  70                  75

Lys Asn Thr Leu Tyr Leu Gln Met Asn Ser Leu Arg Ala Glu Asp
                80                  85                  90

Thr Ala Val Tyr Tyr Cys Ala Arg Asn Leu Gly Pro Ser Phe Tyr
                95                  100                 105

Phe Asp Tyr Trp Gly Gln Gly Thr Leu Val Thr Val Ser Ser
                110                 115

<210> SEQ ID NO 5
<211> LENGTH: 107
<212> TYPE: PRT

<213> ORGANISM: Artificial Sequence
<220> FEATURE:
<223> OTHER INFORMATION: sequence is synthesized

<400> SEQUENCE: 5

Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser
                20                  25                  30

Asn Tyr Leu Ala Trp Tyr Gln Gln Lys Pro Gly Lys Ala Pro Lys
            35                  40                  45

Leu Leu Ile Tyr Ala Ala Ser Ser Leu Glu Ser Gly Val Pro Ser
        50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
                80                  85                  90

Tyr Asn Ser Leu Pro Trp Thr Phe Gly Gln Gly Thr Lys Val Glu
                    95                  100                 105

Ile Lys

<210> SEQ ID NO 6
<211> LENGTH: 119
<212> TYPE: PRT
<213> ORGANISM: Artificial Sequence
<220> FEATURE:
<223> OTHER INFORMATION: sequence is synthesized

<400> SEQUENCE: 6

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser
                20                  25                  30

Ser Tyr Ala Met Ser Trp Val Arg Gln Ala Pro Gly Lys Gly Leu
            35                  40                  45

Glu Trp Val Ala Val Ile Ser Gly Asp Gly Gly Ser Thr Tyr Tyr
        50                  55                  60

Ala Asp Ser Val Lys Gly Arg Phe Thr Ile Ser Arg Asp Asn Ser
65                  70                  75

Lys Asn Thr Leu Tyr Leu Gln Met Asn Ser Leu Arg Ala Glu Asp
                80                  85                  90

Thr Ala Val Tyr Tyr Cys Ala Arg Gly Arg Val Gly Tyr Ser Leu
                    95                  100                 105

Tyr Asp Tyr Trp Gly Gln Gly Thr Leu Val Thr Val Ser Ser
            110                 115

<210> SEQ ID NO 7
<211> LENGTH: 10
<212> TYPE: PRT
<213> ORGANISM: Artificial sequence
<220> FEATURE:
<223> OTHER INFORMATION: Sequence is synthesized.
<220> FEATURE:
<221> NAME/KEY: Xaa
<222> LOCATION: 10
<223> OTHER INFORMATION: Xaa is preferrably D or S

<400> SEQUENCE: 7

Gly Phe Thr Phe Thr Asp Tyr Thr Met Xaa
1               5                   10

```
<210> SEQ ID NO 8
<211> LENGTH: 17
<212> TYPE: PRT
<213> ORGANISM: Artificial sequence
<220> FEATURE:
<223> OTHER INFORMATION: Sequence is synthesized.

<400> SEQUENCE: 8

Asp Val Asn Pro Asn Ser Gly Gly Ser Ile Tyr Asn Gln Arg Phe
 1               5                  10                  15

Lys Gly

<210> SEQ ID NO 9
<211> LENGTH: 10
<212> TYPE: PRT
<213> ORGANISM: Artificial sequence
<220> FEATURE:
<223> OTHER INFORMATION: Sequence is synthesized.

<400> SEQUENCE: 9

Asn Leu Gly Pro Ser Phe Tyr Phe Asp Tyr
 1               5                  10

<210> SEQ ID NO 10
<211> LENGTH: 11
<212> TYPE: PRT
<213> ORGANISM: Artificial sequence
<220> FEATURE:
<223> OTHER INFORMATION: Sequence is synthesized.

<400> SEQUENCE: 10

Lys Ala Ser Gln Asp Val Ser Ile Gly Val Ala
 1               5                  10

<210> SEQ ID NO 11
<211> LENGTH: 7
<212> TYPE: PRT
<213> ORGANISM: Artificial sequence
<220> FEATURE:
<223> OTHER INFORMATION: sequence is synthesized
<220> FEATURE:
<221> NAME/KEY: Xaa
<222> LOCATION: 5
<223> OTHER INFORMATION: Xaa  is preferably R or L
<220> FEATURE:
<221> NAME/KEY: Xaa
<222> LOCATION: 6
<223> OTHER INFORMATION: Xaa is  preferably Y or E
<220> FEATURE:
<221> NAME/KEY: Xaa
<222> LOCATION: 7
<223> OTHER INFORMATION: Xaa is preferably T or S

<400> SEQUENCE: 11

Ser Ala Ser Tyr Xaa Xaa Xaa
 1               5

<210> SEQ ID NO 12
<211> LENGTH: 9
<212> TYPE: PRT
<213> ORGANISM: Artificial sequence
<220> FEATURE:
<223> OTHER INFORMATION: Sequence is synthesized.

<400> SEQUENCE: 12

Gln Gln Tyr Tyr Ile Tyr Pro Tyr Thr
 1               5
```

-continued

```
<210> SEQ ID NO 13
<211> LENGTH: 214
<212> TYPE: PRT
<213> ORGANISM: Artificial sequence
<220> FEATURE:
<223> OTHER INFORMATION: Sequence is synthesized.

<400> SEQUENCE: 13

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Asn
                20                  25                  30

Thr Ala Val Ala Trp Tyr Gln Gln Lys Pro Gly Lys Ala Pro Lys
            35                  40                  45

Leu Leu Ile Tyr Ser Ala Ser Phe Leu Tyr Ser Gly Val Pro Ser
        50                  55                  60

Arg Phe Ser Gly Ser Arg Ser Gly Thr Asp Phe Thr Leu Thr Ile
    65                  70                  75

Ser Ser Leu Gln Pro Glu Asp Phe Ala Thr Tyr Tyr Cys Gln Gln
                80                  85                  90

His Tyr Thr Thr Pro Pro Thr Phe Gly Gln Gly Thr Lys Val Glu
                95                 100                 105

Ile Lys Arg Thr Val Ala Ala Pro Ser Val Phe Ile Phe Pro Pro
            110                 115                 120

Ser Asp Glu Gln Leu Lys Ser Gly Thr Ala Ser Val Val Cys Leu
        125                 130                 135

Leu Asn Asn Phe Tyr Pro Arg Glu Ala Lys Val Gln Trp Lys Val
    140                 145                 150

Asp Asn Ala Leu Gln Ser Gly Asn Ser Gln Glu Ser Val Thr Glu
                155                 160                 165

Gln Asp Ser Lys Asp Ser Thr Tyr Ser Leu Ser Ser Thr Leu Thr
                170                 175                 180

Leu Ser Lys Ala Asp Tyr Glu Lys His Lys Val Tyr Ala Cys Glu
            185                 190                 195

Val Thr His Gln Gly Leu Ser Ser Pro Val Thr Lys Ser Phe Asn
        200                 205                 210

Arg Gly Glu Cys

<210> SEQ ID NO 14
<211> LENGTH: 449
<212> TYPE: PRT
<213> ORGANISM: Artificial sequence
<220> FEATURE:
<223> OTHER INFORMATION: sequence is synthesized

<400> SEQUENCE: 14

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Asn Ile Lys
                20                  25                  30

Asp Thr Tyr Ile His Trp Val Arg Gln Ala Pro Gly Lys Gly Leu
            35                  40                  45

Glu Trp Val Ala Arg Ile Tyr Pro Thr Asn Gly Tyr Thr Arg Tyr
        50                  55                  60

Ala Asp Ser Val Lys Gly Arg Phe Thr Ile Ser Ala Asp Thr Ser
    65                  70                  75

Lys Asn Thr Ala Tyr Leu Gln Met Asn Ser Leu Arg Ala Glu Asp
                80                  85                  90
```

```
Thr Ala Val Tyr Tyr Cys Ser Arg Trp Gly Gly Asp Gly Phe Tyr
                95                 100                 105
Ala Met Asp Tyr Trp Gly Gln Gly Thr Leu Val Thr Val Ser Ser
            110                 115                 120
Ala Ser Thr Lys Gly Pro Ser Val Phe Pro Leu Ala Pro Ser Ser
            125                 130                 135
Lys Ser Thr Ser Gly Gly Thr Ala Ala Leu Gly Cys Leu Val Lys
            140                 145                 150
Asp Tyr Phe Pro Glu Pro Val Thr Val Ser Trp Asn Ser Gly Ala
            155                 160                 165
Leu Thr Ser Gly Val His Thr Phe Pro Ala Val Leu Gln Ser Ser
            170                 175                 180
Gly Leu Tyr Ser Leu Ser Ser Val Val Thr Val Pro Ser Ser Ser
            185                 190                 195
Leu Gly Thr Gln Thr Tyr Ile Cys Asn Val Asn His Lys Pro Ser
            200                 205                 210
Asn Thr Lys Val Asp Lys Lys Val Glu Pro Lys Ser Cys Asp Lys
            215                 220                 225
Thr His Thr Cys Pro Pro Cys Pro Ala Pro Glu Leu Leu Gly Gly
            230                 235                 240
Pro Ser Val Phe Leu Phe Pro Pro Lys Pro Lys Asp Thr Leu Met
            245                 250                 255
Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val
            275                 280                 285
Glu Val His Asn Ala Lys Thr Lys Pro Arg Glu Glu Gln Tyr Asn
            290                 295                 300
Ser Thr Tyr Arg Val Val Ser Val Leu Thr Val Leu His Gln Asp
            305                 310                 315
Trp Leu Asn Gly Lys Glu Tyr Lys Cys Lys Val Ser Asn Lys Ala
            320                 325                 330
Leu Pro Ala Pro Ile Glu Lys Thr Ile Ser Lys Ala Lys Gly Gln
            335                 340                 345
Pro Arg Glu Pro Gln Val Tyr Thr Leu Pro Pro Ser Arg Glu Glu
            350                 355                 360
Met Thr Lys Asn Gln Val Ser Leu Thr Cys Leu Val Lys Gly Phe
            365                 370                 375
Tyr Pro Ser Asp Ile Ala Val Glu Trp Glu Ser Asn Gly Gln Pro
            380                 385                 390
Glu Asn Asn Tyr Lys Thr Thr Pro Pro Val Leu Asp Ser Asp Gly
            395                 400                 405
Ser Phe Phe Leu Tyr Ser Lys Leu Thr Val Asp Lys Ser Arg Trp
            410                 415                 420
Gln Gln Gly Asn Val Phe Ser Cys Ser Val Met His Glu Ala Leu
            425                 430                 435
His Asn His Tyr Thr Gln Lys Ser Leu Ser Leu Ser Pro Gly
            440                 445

<210> SEQ ID NO 15
<211> LENGTH: 214
<212> TYPE: PRT
<213> ORGANISM: Artificial sequence
<220> FEATURE:
<223> OTHER INFORMATION: Sequence is synthesized.
```

<400> SEQUENCE: 15

Asp Ile Gln Met Thr Gln Ser Pro Ser Ser Leu Ser Ala Ser Val
1               5                   10                  15

Gly Asp Arg Val Thr Ile Thr Cys Lys Ala Ser Gln Asp Val Ser
            20                  25                  30

Ile Gly Val Ala Trp Tyr Gln Gln Lys Pro Gly Lys Ala Pro Lys
        35                  40                  45

Leu Leu Ile Tyr Ser Ala Ser Tyr Arg Tyr Thr Gly Val Pro Ser
    50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
            80                  85                  90

Tyr Tyr Ile Tyr Pro Tyr Thr Phe Gly Gln Gly Thr Lys Val Glu
        95                  100                 105

Ile Lys Arg Thr Val Ala Ala Pro Ser Val Phe Ile Phe Pro Pro
    110                 115                 120

Ser Asp Glu Gln Leu Lys Ser Gly Thr Ala Ser Val Val Cys Leu
125                 130                 135

Leu Asn Asn Phe Tyr Pro Arg Glu Ala Lys Val Gln Trp Lys Val
            140                 145                 150

Asp Asn Ala Leu Gln Ser Gly Asn Ser Gln Glu Ser Val Thr Glu
        155                 160                 165

Gln Asp Ser Lys Asp Ser Thr Tyr Ser Leu Ser Ser Thr Leu Thr
    170                 175                 180

Leu Ser Lys Ala Asp Tyr Glu Lys His Lys Val Tyr Ala Cys Glu
185                 190                 195

Val Thr His Gln Gly Leu Ser Ser Pro Val Thr Lys Ser Phe Asn
            200                 205                 210

Arg Gly Glu Cys

<210> SEQ ID NO 16
<211> LENGTH: 448
<212> TYPE: PRT
<213> ORGANISM: Artificial sequence
<220> FEATURE:
<223> OTHER INFORMATION: Sequence is synthesized.

<400> SEQUENCE: 16

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Thr
            20                  25                  30

Asp Tyr Thr Met Asp Trp Val Arg Gln Ala Pro Gly Lys Gly Leu
        35                  40                  45

Glu Trp Val Ala Asp Val Asn Pro Asn Ser Gly Gly Ser Ile Tyr
    50                  55                  60

Asn Gln Arg Phe Lys Gly Arg Phe Thr Leu Ser Val Asp Arg Ser
65                  70                  75

Lys Asn Thr Leu Tyr Leu Gln Met Asn Ser Leu Arg Ala Glu Asp
            80                  85                  90

Thr Ala Val Tyr Tyr Cys Ala Arg Asn Leu Gly Pro Ser Phe Tyr
        95                  100                 105

Phe Asp Tyr Trp Gly Gln Gly Thr Leu Val Thr Val Ser Ser Ala
    110                 115                 120

Ser Thr Lys Gly Pro Ser Val Phe Pro Leu Ala Pro Ser Ser Lys
            125                 130                 135

Ser Thr Ser Gly Gly Thr Ala Ala Leu Gly Cys Leu Val Lys Asp
            140                 145                 150

Tyr Phe Pro Glu Pro Val Thr Val Ser Trp Asn Ser Gly Ala Leu
            155                 160                 165

Thr Ser Gly Val His Thr Phe Pro Ala Val Leu Gln Ser Ser Gly
            170                 175                 180

Leu Tyr Ser Leu Ser Ser Val Val Thr Val Pro Ser Ser Ser Leu
            185                 190                 195

Gly Thr Gln Thr Tyr Ile Cys Asn Val Asn His Lys Pro Ser Asn
            200                 205                 210

Thr Lys Val Asp Lys Lys Val Glu Pro Lys Ser Cys Asp Lys Thr
            215                 220                 225

His Thr Cys Pro Pro Cys Pro Ala Pro Glu Leu Leu Gly Gly Pro
            230                 235                 240

Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp
            305                 310                 315

Leu Asn Gly Lys Glu Tyr Lys Cys Lys Val Ser Asn Lys Ala Leu
            320                 325                 330

Pro Ala Pro Ile Glu Lys Thr Ile Ser Lys Ala Lys Gly Gln Pro
            335                 340                 345

Arg Glu Pro Gln Val Tyr Thr Leu Pro Pro Ser Arg Glu Glu Met
            350                 355                 360

Thr Lys Asn Gln Val Ser Leu Thr Cys Leu Val Lys Gly Phe Tyr
            365                 370                 375

Pro Ser Asp Ile Ala Val Glu Trp Glu Ser Asn Gly Gln Pro Glu
            380                 385                 390

Asn Asn Tyr Lys Thr Thr Pro Pro Val Leu Asp Ser Asp Gly Ser
            395                 400                 405

Phe Phe Leu Tyr Ser Lys Leu Thr Val Asp Lys Ser Arg Trp Gln
            410                 415                 420

Gln Gly Asn Val Phe Ser Cys Ser Val Met His Glu Ala Leu His
            425                 430                 435

Asn His Tyr Thr Gln Lys Ser Leu Ser Leu Ser Pro Gly
            440                 445

<210> SEQ ID NO 17
<211> LENGTH: 233
<212> TYPE: PRT
<213> ORGANISM: Artificial sequence
<220> FEATURE:
<223> OTHER INFORMATION: Sequence is synthesized.

<400> SEQUENCE: 17

Met Gly Trp Ser Cys Ile Ile Leu Phe Leu Val Ala Thr Ala Thr
 1               5                  10                  15

```
Gly Val His Ser Asp Ile Gln Met Thr Gln Ser Pro Ser Ser Leu
             20                  25                  30

Ser Ala Ser Val Gly Asp Arg Val Thr Ile Thr Cys Lys Ala Ser
             35                  40                  45

Gln Asp Val Ser Ile Gly Val Ala Trp Tyr Gln Gln Lys Pro Gly
             50                  55                  60

Lys Ala Pro Lys Leu Leu Ile Tyr Ser Ala Ser Tyr Arg Tyr Thr
             65                  70                  75

Gly Val Pro Ser Arg Phe Ser Gly Ser Gly Ser Gly Thr Asp Phe
             80                  85                  90

Thr Leu Thr Ile Ser Ser Leu Gln Pro Glu Asp Phe Ala Thr Tyr
             95                 100                 105

Tyr Cys Gln Gln Tyr Tyr Ile Tyr Pro Tyr Thr Phe Gly Gln Gly
            110                 115                 120

Thr Lys Val Glu Ile Lys Arg Thr Val Ala Ala Pro Ser Val Phe
            125                 130                 135

Ile Phe Pro Pro Ser Asp Glu Gln Leu Lys Ser Gly Thr Ala Ser
            140                 145                 150

Val Val Cys Leu Leu Asn Asn Phe Tyr Pro Arg Glu Ala Lys Val
            155                 160                 165

Gln Trp Lys Val Asp Asn Ala Leu Gln Ser Gly Asn Ser Gln Glu
            170                 175                 180

Ser Val Thr Glu Gln Asp Ser Lys Asp Ser Thr Tyr Ser Leu Ser
            185                 190                 195

Ser Thr Leu Thr Leu Ser Lys Ala Asp Tyr Glu Lys His Lys Val
            200                 205                 210

Tyr Ala Cys Glu Val Thr His Gln Gly Leu Ser Ser Pro Val Thr
            215                 220                 225

Lys Ser Phe Asn Arg Gly Glu Cys
            230

<210> SEQ ID NO 18
<211> LENGTH: 467
<212> TYPE: PRT
<213> ORGANISM: Artificial sequence
<220> FEATURE:
<223> OTHER INFORMATION: Sequence is synthesized.

<400> SEQUENCE: 18

Met Gly Trp Ser Cys Ile Ile Leu Phe Leu Val Ala Thr Ala Thr
  1               5                  10                  15

Gly Val His Ser Glu Val Gln Leu Val Glu Ser Gly Gly Gly Leu
             20                  25                  30

Val Gln Pro Gly Gly Ser Leu Arg Leu Ser Cys Ala Ala Ser Gly
             35                  40                  45

Phe Thr Phe Thr Asp Tyr Thr Met Asp Trp Val Arg Gln Ala Pro
             50                  55                  60

Gly Lys Gly Leu Glu Trp Val Ala Asp Val Asn Pro Asn Ser Gly
             65                  70                  75

Gly Ser Ile Tyr Asn Gln Arg Phe Lys Gly Arg Phe Thr Leu Ser
             80                  85                  90

Val Asp Arg Ser Lys Asn Thr Leu Tyr Leu Gln Met Asn Ser Leu
             95                 100                 105

Arg Ala Glu Asp Thr Ala Val Tyr Tyr Cys Ala Arg Asn Leu Gly
            110                 115                 120

Pro Ser Phe Tyr Phe Asp Tyr Trp Gly Gln Gly Thr Leu Val Thr
```

125                 130                 135

Val Ser Ser Ala Ser Thr Lys Gly Pro Ser Val Phe Pro Leu Ala
                140                 145                 150

Pro Ser Ser Lys Ser Thr Ser Gly Gly Thr Ala Ala Leu Gly Cys
                155                 160                 165

Leu Val Lys Asp Tyr Phe Pro Glu Pro Val Thr Val Ser Trp Asn
                170                 175                 180

Ser Gly Ala Leu Thr Ser Gly Val His Thr Phe Pro Ala Val Leu
                185                 190                 195

Gln Ser Ser Gly Leu Tyr Ser Leu Ser Ser Val Val Thr Val Pro
                200                 205                 210

Ser Ser Ser Leu Gly Thr Gln Thr Tyr Ile Cys Asn Val Asn His
                215                 220                 225

Lys Pro Ser Asn Thr Lys Val Asp Lys Lys Val Glu Pro Lys Ser
                230                 235                 240

Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val
                275                 280                 285

Asp Val Ser His Glu Asp Pro Glu Val Lys Phe Asn Trp Tyr Val
                290                 295                 300

Asp Gly Val Glu Val His Asn Ala Lys Thr Lys Pro Arg Glu Glu
                305                 310                 315

Gln Tyr Asn Ser Thr Tyr Arg Val Val Ser Val Leu Thr Val Leu
                320                 325                 330

His Gln Asp Trp Leu Asn Gly Lys Glu Tyr Lys Cys Lys Val Ser
                335                 340                 345

Asn Lys Ala Leu Pro Ala Pro Ile Glu Lys Thr Ile Ser Lys Ala
                350                 355                 360

Lys Gly Gln Pro Arg Glu Pro Gln Val Tyr Thr Leu Pro Pro Ser
                365                 370                 375

Arg Glu Glu Met Thr Lys Asn Gln Val Ser Leu Thr Cys Leu Val
                380                 385                 390

Lys Gly Phe Tyr Pro Ser Asp Ile Ala Val Glu Trp Glu Ser Asn
                395                 400                 405

Gly Gln Pro Glu Asn Asn Tyr Lys Thr Thr Pro Pro Val Leu Asp
                410                 415                 420

Ser Asp Gly Ser Phe Phe Leu Tyr Ser Lys Leu Thr Val Asp Lys
                425                 430                 435

Ser Arg Trp Gln Gln Gly Asn Val Phe Ser Cys Ser Val Met His
                440                 445                 450

Glu Ala Leu His Asn His Tyr Thr Gln Lys Ser Leu Ser Leu Ser
                455                 460                 465

Pro Gly

<210> SEQ ID NO 19
<211> LENGTH: 195
<212> TYPE: PRT
<213> ORGANISM: Homo sapiens

<400> SEQUENCE: 19

Thr Gln Val Cys Thr Gly Thr Asp Met Lys Leu Arg Leu Pro Ala
 1               5                  10                  15

Ser Pro Glu Thr His Leu Asp Met Leu Arg His Leu Tyr Gln Gly
              20                  25                  30

Cys Gln Val Val Gln Gly Asn Leu Glu Leu Thr Tyr Leu Pro Thr
          35                  40                  45

Asn Ala Ser Leu Ser Phe Leu Gln Asp Ile Gln Glu Val Gln Gly
      50                  55                  60

Tyr Val Leu Ile Ala His Asn Gln Val Arg Gln Val Pro Leu Gln
  65                  70                  75

Arg Leu Arg Ile Val Arg Gly Thr Gln Leu Phe Glu Asp Asn Tyr
              80                  85                  90

Ala Leu Ala Val Leu Asp Asn Gly Asp Pro Leu Asn Asn Thr Thr
          95                 100                 105

Pro Val Thr Gly Ala Ser Pro Gly Gly Leu Arg Glu Leu Gln Leu
     110                 115                 120

Arg Ser Leu Thr Glu Ile Leu Lys Gly Gly Val Leu Ile Gln Arg
 125                 130                 135

Asn Pro Gln Leu Cys Tyr Gln Asp Thr Ile Leu Trp Lys Asp Ile
             140                 145                 150

Phe His Lys Asn Asn Gln Leu Ala Leu Thr Leu Ile Asp Thr Asn
         155                 160                 165

Arg Ser Arg Ala Cys His Pro Cys Ser Pro Met Cys Lys Gly Ser
     170                 175                 180

Arg Cys Trp Gly Glu Ser Ser Glu Asp Cys Gln Ser Leu Thr Arg
 185                 190                 195

<210> SEQ ID NO 20
<211> LENGTH: 124
<212> TYPE: PRT
<213> ORGANISM: Homo sapiens

<400> SEQUENCE: 20

Thr Val Cys Ala Gly Gly Cys Ala Arg Cys Lys Gly Pro Leu Pro
1               5                   10                  15

Thr Asp Cys Cys His Glu Gln Cys Ala Ala Gly Cys Thr Gly Pro
             20                  25                  30

Lys His Ser Asp Cys Leu Ala Cys Leu His Phe Asn His Ser Gly
         35                  40                  45

Ile Cys Glu Leu His Cys Pro Ala Leu Val Thr Tyr Asn Thr Asp
     50                  55                  60

Thr Phe Glu Ser Met Pro Asn Pro Glu Gly Arg Tyr Thr Phe Gly
 65                  70                  75

Ala Ser Cys Val Thr Ala Cys Pro Tyr Asn Tyr Leu Ser Thr Asp
             80                  85                  90

Val Gly Ser Cys Thr Leu Val Cys Pro Leu His Asn Gln Glu Val
         95                 100                 105

Thr Ala Glu Asp Gly Thr Gln Arg Cys Glu Lys Cys Ser Lys Pro
     110                 115                 120

Cys Ala Arg Val

<210> SEQ ID NO 21
<211> LENGTH: 169
<212> TYPE: PRT
<213> ORGANISM: Homo sapiens

<400> SEQUENCE: 21

Cys Tyr Gly Leu Gly Met Glu His Leu Arg Glu Val Arg Ala Val

```
                1               5              10              15
        Thr Ser Ala Asn Ile Gln Glu Phe Ala Gly Cys Lys Lys Ile Phe
                         20                  25                  30

Gly Ser Leu Ala Phe Leu Pro Glu Ser Phe Asp Gly Asp Pro Ala
                         35                  40                  45

Ser Asn Thr Ala Pro Leu Gln Pro Glu Gln Leu Gln Val Phe Glu
                         50                  55                  60

Thr Leu Glu Glu Ile Thr Gly Tyr Leu Tyr Ile Ser Ala Trp Pro
                         65                  70                  75

Asp Ser Leu Pro Asp Leu Ser Val Phe Gln Asn Leu Gln Val Ile
                         80                  85                  90

Arg Gly Arg Ile Leu His Asn Gly Ala Tyr Ser Leu Thr Leu Gln
                         95                 100                 105

Gly Leu Gly Ile Ser Trp Leu Gly Leu Arg Ser Leu Arg Glu Leu
                        110                 115                 120

Gly Ser Gly Leu Ala Leu Ile His His Asn Thr His Leu Cys Phe
                        125                 130                 135

Val His Thr Val Pro Trp Asp Gln Leu Phe Arg Asn Pro His Gln
                        140                 145                 150

Ala Leu Leu His Thr Ala Asn Arg Pro Glu Asp Glu Cys Val Gly
                        155                 160                 165

Glu Gly Leu Ala

<210> SEQ ID NO 22
<211> LENGTH: 142
<212> TYPE: PRT
<213> ORGANISM: Homo sapiens

<400> SEQUENCE: 22

Cys His Gln Leu Cys Ala Arg Gly His Cys Trp Gly Pro Gly Pro
         1               5                  10                  15

Thr Gln Cys Val Asn Cys Ser Gln Phe Leu Arg Gly Gln Glu Cys
                         20                  25                  30

Val Glu Glu Cys Arg Val Leu Gln Gly Leu Pro Arg Glu Tyr Val
                         35                  40                  45

Asn Ala Arg His Cys Leu Pro Cys His Pro Glu Cys Gln Pro Gln
                         50                  55                  60

Asn Gly Ser Val Thr Cys Phe Gly Pro Glu Ala Asp Gln Cys Val
                         65                  70                  75

Ala Cys Ala His Tyr Lys Asp Pro Pro Phe Cys Val Ala Arg Cys
                         80                  85                  90

Pro Ser Gly Val Lys Pro Asp Leu Ser Tyr Met Pro Ile Trp Lys
                         95                 100                 105

Phe Pro Asp Glu Glu Gly Ala Cys Gln Pro Cys Pro Ile Asn Cys
                        110                 115                 120

Thr His Ser Cys Val Asp Leu Asp Asp Lys Gly Cys Pro Ala Glu
                        125                 130                 135

Gln Arg Ala Ser Pro Leu Thr
                        140

<210> SEQ ID NO 23
<211> LENGTH: 217
<212> TYPE: PRT
<213> ORGANISM: Artificial sequence
<220> FEATURE:
<223> OTHER INFORMATION: Sequence is synthesized.
```

<400> SEQUENCE: 23

```
Val His Ser Asp Ile Gln Met Thr Gln Ser Pro Ser Ser Leu Ser
  1               5                  10                  15

Ala Ser Val Gly Asp Arg Val Thr Ile Thr Cys Lys Ala Ser Gln
                 20                  25                  30

Asp Val Ser Ile Gly Val Ala Trp Tyr Gln Gln Lys Pro Gly Lys
                 35                  40                  45

Ala Pro Lys Leu Leu Ile Tyr Ser Ala Ser Tyr Arg Tyr Thr Gly
                 50                  55                  60

Val Pro Ser Arg Phe Ser Gly Ser Gly Ser Gly Thr Asp Phe Thr
                 65                  70                  75

Leu Thr Ile Ser Ser Leu Gln Pro Glu Asp Phe Ala Thr Tyr Tyr
                 80                  85                  90

Cys Gln Gln Tyr Tyr Ile Tyr Pro Tyr Thr Phe Gly Gln Gly Thr
                 95                 100                 105

Lys Val Glu Ile Lys Arg Thr Val Ala Ala Pro Ser Val Phe Ile
                110                 115                 120

Phe Pro Pro Ser Asp Glu Gln Leu Lys Ser Gly Thr Ala Ser Val
                125                 130                 135

Val Cys Leu Leu Asn Asn Phe Tyr Pro Arg Glu Ala Lys Val Gln
                140                 145                 150

Trp Lys Val Asp Asn Ala Leu Gln Ser Gly Asn Ser Gln Glu Ser
                155                 160                 165

Val Thr Glu Gln Asp Ser Lys Asp Ser Thr Tyr Ser Leu Ser Ser
                170                 175                 180

Thr Leu Thr Leu Ser Lys Ala Asp Tyr Glu Lys His Lys Val Tyr
                185                 190                 195

Ala Cys Glu Val Thr His Gln Gly Leu Ser Ser Pro Val Thr Lys
                200                 205                 210

Ser Phe Asn Arg Gly Glu Cys
                215
```

<210> SEQ ID NO 24
<211> LENGTH: 449
<212> TYPE: PRT
<213> ORGANISM: Artificial sequence
<220> FEATURE:
<223> OTHER INFORMATION: Sequence is synthesized.

<400> SEQUENCE: 24

```
Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Thr Phe Thr
                 20                  25                  30

Asp Tyr Thr Met Asp Trp Val Arg Gln Ala Pro Gly Lys Gly Leu
                 35                  40                  45

Glu Trp Val Ala Asp Val Asn Pro Asn Ser Gly Gly Ser Ile Tyr
                 50                  55                  60

Asn Gln Arg Phe Lys Gly Arg Phe Thr Leu Ser Val Asp Arg Ser
                 65                  70                  75

Lys Asn Thr Leu Tyr Leu Gln Met Asn Ser Leu Arg Ala Glu Asp
                 80                  85                  90

Thr Ala Val Tyr Tyr Cys Ala Arg Asn Leu Gly Pro Ser Phe Tyr
                 95                 100                 105

Phe Asp Tyr Trp Gly Gln Gly Thr Leu Val Thr Val Ser Ser Ala
                110                 115                 120
```

-continued

```
Ser Thr Lys Gly Pro Ser Val Phe Pro Leu Ala Pro Ser Ser Lys
                125                 130                 135

Ser Thr Ser Gly Gly Thr Ala Ala Leu Gly Cys Leu Val Lys Asp
                140                 145                 150

Tyr Phe Pro Glu Pro Val Thr Val Ser Trp Asn Ser Gly Ala Leu
                155                 160                 165

Thr Ser Gly Val His Thr Phe Pro Ala Val Leu Gln Ser Ser Gly
                170                 175                 180

Leu Tyr Ser Leu Ser Ser Val Val Thr Val Pro Ser Ser Ser Leu
                185                 190                 195

Gly Thr Gln Thr Tyr Ile Cys Asn Val Asn His Lys Pro Ser Asn
                200                 205                 210

Thr Lys Val Asp Lys Lys Val Glu Pro Lys Ser Cys Asp Lys Thr
                215                 220                 225

His Thr Cys Pro Pro Cys Pro Ala Pro Glu Leu Leu Gly Gly Pro
                230                 235                 240

Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser
                290                 295                 300

Thr Tyr Arg Val Val Ser Val Leu Thr Val Leu His Gln Asp Trp
                305                 310                 315

Leu Asn Gly Lys Glu Tyr Lys Cys Lys Val Ser Asn Lys Ala Leu
                320                 325                 330

Pro Ala Pro Ile Glu Lys Thr Ile Ser Lys Ala Lys Gly Gln Pro
                335                 340                 345

Arg Glu Pro Gln Val Tyr Thr Leu Pro Pro Ser Arg Glu Glu Met
                350                 355                 360

Thr Lys Asn Gln Val Ser Leu Thr Cys Leu Val Lys Gly Phe Tyr
                365                 370                 375

Pro Ser Asp Ile Ala Val Glu Trp Glu Ser Asn Gly Gln Pro Glu
                380                 385                 390

Asn Asn Tyr Lys Thr Thr Pro Pro Val Leu Asp Ser Asp Gly Ser
                395                 400                 405

Phe Phe Leu Tyr Ser Lys Leu Thr Val Asp Lys Ser Arg Trp Gln
                410                 415                 420

Gln Gly Asn Val Phe Ser Cys Ser Val Met His Glu Ala Leu His
                425                 430                 435

Asn His Tyr Thr Gln Lys Ser Leu Ser Leu Ser Pro Gly Lys
                440                 445
```